(12) United States Patent
Szymkiewicz et al.

(10) Patent No.: US 12,359,160 B1
(45) Date of Patent: Jul. 15, 2025

(54) APPARATUS FOR FACILITATING AUTOMATED LOADING AND UNLOADING CONSUMABLE KIT TO CELL PROCESSING INSTRUMENT

(71) Applicant: Multiply Labs Inc., San Francisco, CA (US)

(72) Inventors: Dorothy Szymkiewicz, San Francisco, CA (US); Sebastien Wah, San Francisco, CA (US)

(73) Assignee: MULTIPLY LABS INC., San Francisco, CA (US)

( * ) Notice: Subject to any disclaimer, the term of this patent is extended or adjusted under 35 U.S.C. 154(b) by 0 days.

(21) Appl. No.: 19/011,561

(22) Filed: Jan. 6, 2025

Related U.S. Application Data

(60) Provisional application No. 63/698,008, filed on Sep. 23, 2024, provisional application No. 63/618,280, filed on Jan. 5, 2024.

(51) Int. Cl.
| | |
|---|---|
| *C12M 1/00* | (2006.01) |
| *C12M 1/36* | (2006.01) |
| *C12M 3/00* | (2006.01) |
| *G01N 35/00* | (2006.01) |

(52) U.S. Cl.
CPC ............ *C12M 41/48* (2013.01); *C12M 23/40* (2013.01); *C12M 23/42* (2013.01); *C12M 23/48* (2013.01); *C12M 29/06* (2013.01); *G01N 35/0099* (2013.01)

(58) Field of Classification Search
CPC ...... C12M 41/48; C12M 23/40; C12M 23/42; C12M 23/48; C12M 29/06; G01N 35/0099
See application file for complete search history.

(56) References Cited

U.S. PATENT DOCUMENTS

| | | | |
|---|---|---|---|
| 2009/0215022 A1* | 8/2009 | Page | C12M 23/44 435/286.5 |
| 2011/0207209 A1* | 8/2011 | Hammons | C12M 23/42 435/303.1 |

* cited by examiner

*Primary Examiner* — Michael L Hobbs
(74) *Attorney, Agent, or Firm* — Morgan, Lewis & Bockius LLP

(57) ABSTRACT

An apparatus includes a cartridge for holding a consumable kit and a dock for holding an instrument. The cartridge includes first docking members and first locking members, and the dock includes second docking members and second locking members. The first and second docking members are removably coupled to each other, establishing a single degree of freedom motion for moving the cartridge relative to the dock. The first and second locking members are selectively coupled to each other, selectively locking the cartridge with the dock in the single degree of freedom motion. The apparatus facilities automated loading of the consumable kit to the instrument.

30 Claims, 32 Drawing Sheets

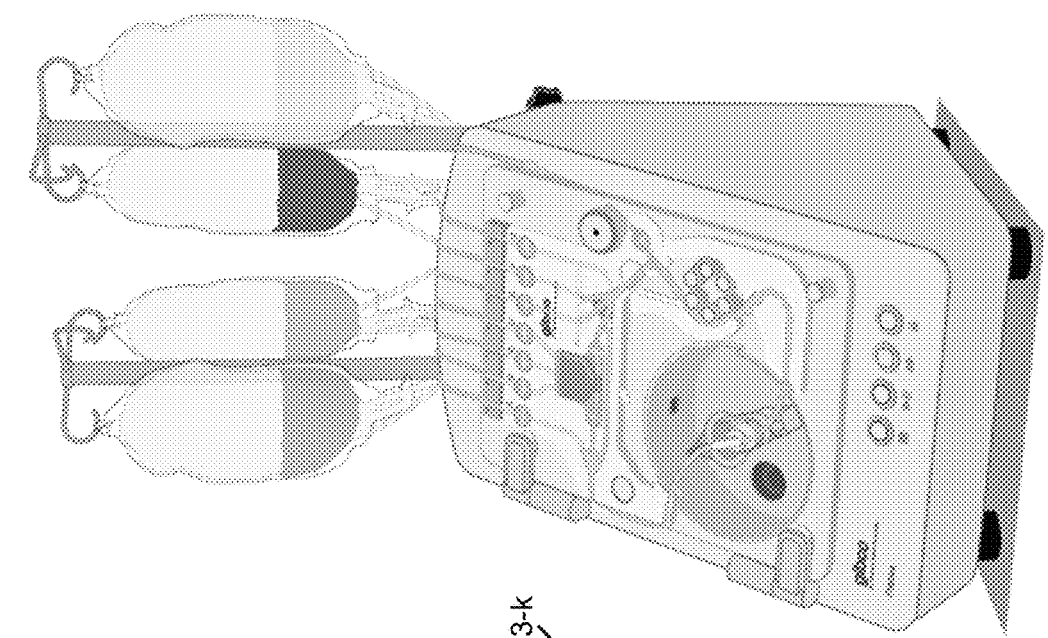
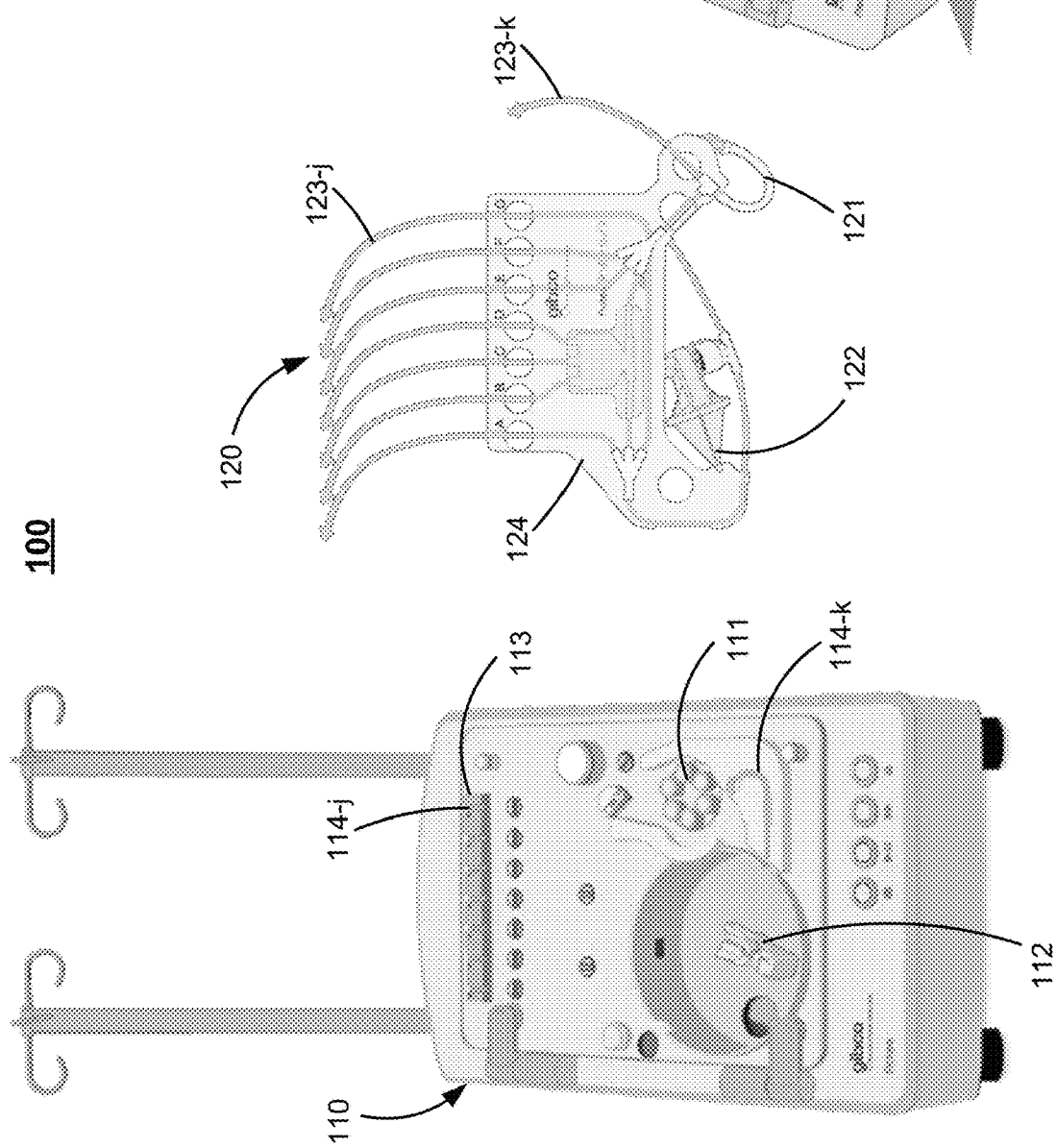
Figure 1A  Figure 1B  Figure 1C

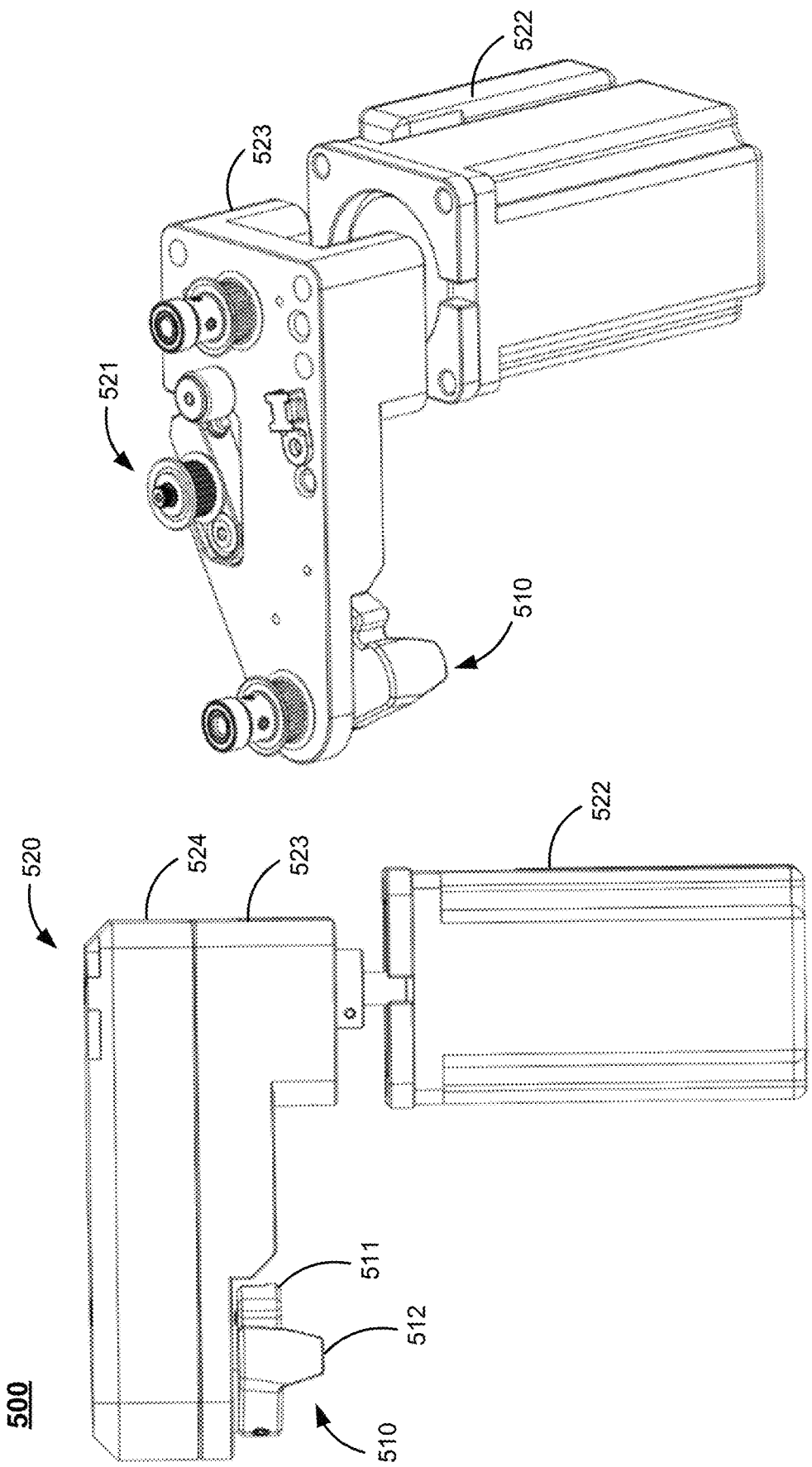

700

APPARATUS FOR FACILITATING AUTOMATED LOADING AND UNLOADING CONSUMABLE KIT TO CELL PROCESSING INSTRUMENT

CROSS-REFERENCE TO RELATED APPLICATION

The present application claims priority to U.S. Provisional Patent Application No. 63/618,280 filed Jan. 5, 2024, and U.S. Provisional Patent Application No. 63/698,008 filed Sep. 23, 2024, each of which is hereby incorporated by reference in its entirety for all purposes.

TECHNICAL FIELD

The present disclosure generally relates to devices, systems and methods for facilitating automated manufacturing at a biological foundry, and in particular to apparatuses for facilitating automated loading and unloading of consumable kits to cell processing instruments.

BACKGROUND

Cell therapies are next-generation drugs where live cells are used to treat a subject. This is in contrast with traditional small-molecule and biologic drugs, where small or large molecules—but not whole living cells—are used to treat patients. Many of the most recent and promising innovations in medicine are represented by cell therapies in which the cells of a subject (either the patient or a donor) are extracted, genetically engineered in a lab, grown in an incubator, and finally infused in the patient in order to achieve a therapeutic effect. However, despite the life-saving effects of many cell therapies, there are significant bottlenecks to their widespread adoption. For instance, one obstacle is represented by the current limits in manufacturing capacity for cell therapies. Conventional cell therapy production processes are still largely labor-based and inefficient.

Traditionally, cell therapies are produced with labor-intensive processes. These conventional processes require not only a large number of manufacturing operators, but also the employment of highly skilled (and expensive) technicians. These constraints make it particularly difficult to manufacture cell therapies at an industrial scale. Cell therapy manufacturing processes are low-scale and labor-intensive because they were originally developed in the context of academic research. The original lab processes—which were developed to demonstrate the feasibility of cell therapies—were then hastily modified and retrofitted in order to fulfill regulatory requirements and achieve good manufacturing practices.

This conventional approach allowed drug manufacturers to bring to the market the first approved cell therapies. However, this labor-intensive, lab-oriented approach is unsuitable to achieve industrial scale. At their core, current cell manufacturing processes were designed to be manually completed by highly trained personnel—such as the researchers that conduct scientific experiments in an academic environment. Requiring this type of skillset becomes a disadvantage in an industrial setting. Cell manufacturing processes depend on highly trained, highly educated manual labor, and this makes them incompatible with the efficiency of mass-manufacturing industrial processes.

The dominant conventional approach to cell manufacturing is based on a set of separate individual pieces of manufacturing equipment placed on a clean room bench. This manufacturing process still looks exactly like a research laboratory, where all the machinery is manually operated and directly supervised by highly skilled operators. In order to execute the cell manufacturing processes, these skilled operators gown up, enter a clean room, and manually activate the machines. The operators also transfer the batch material from machine to machine, manually sample the batches to perform quality control testing, ensure that reagents are delivered to the cells, and ensure that waste material is removed. This labor-based conventional approach is very different from the organization of industrial-scale processes, where most tasks are autonomously executed by specialized machinery, which is supervised by ordinary manufacturing technicians (not engineers, nor scientists).

As such, the conventional labor-based approach to cell therapy manufacturing has at least three fundamental limits. First, the conventional approach is not scalable and not robust to operator variability. Because the conventional approach is extremely labor-intensive, cell therapy manufacturing is limited to small-scale applications. Increasing throughput beyond a few hundred products per year has proven extremely difficult, because such an effort would require hiring, training, retaining, and managing a large number of highly skilled, expensive operators. Moreover, labor-based processes are typically unable to reach industrial scale, and cell manufacturing is not an exception. This pronounced reliance of labor presents additional disadvantages, including the fact that—because of operator variability—the yield and the features of the finished cell therapy product are hard to predict and to control. This operator variability makes scaling the process of manufacturing cell therapy products even harder—particularly in terms of margins, in which a higher number of rejected batches increases the cost per batch.

Additionally, the conventional approach to manufacturing cell therapy products is inefficient. Since individual machines for the cell therapy manufacturing process are utilized in series (e.g., the machines are used one at a time, with a single batch manually moved from a piece of machinery to the next), when a machine is active all the others are idle. This results in a low utilization rate for all machines, since most of the machines are waiting for the batch to arrive, while a single machine is being used. The problem of a very low utilization rate is particularly evident for cell manufacturing processes, which are characterized by machines with markedly different cycle times. More specifically, systems like bioreactors process a single batch for weeks, while machines like thawing and freezing systems are only used for a few hours on a single batch. This results in utilization rates that are even lower for the faster machines—because the slower machines are the bottleneck and limit the rate of the rest of the serial process.

Finally, the conventional approach to manufacturing cell therapy products has low throughput. Because the process is managed and executed by human operators, only one batch can be produced at any given time on a serial production line. For instance, if two batches were manufactured at the same time on the same production line, in fact, there would be high risk of cross-contamination or of mix-up errors by the operators. Since all the serial machines are used for just one product at a time, the resulting throughput of the production line is extremely low. As a reference, typically a cell therapy product takes two to three weeks to be manufactured. This means that, in order to avoid mix-ups, a whole production line must be reserved for a single product for about half of a month—a rate that is incompatible with industrial scale. Because of this temporal constraint, a whole manufacturing suite (typically consisting of about 1,000 square feet of clean room space) must be reserved for a single serial production line. Therefore, the only way to increase throughput via this conventional approach is by creating facilities with multiple independent suites that replicate the same process. However, each suite can only handle one product at a time, occupies significant clean room space, and is entirely operated by skilled labor. As such, this conventional approach is not scalable, and not suitable to manufacture more than a few hundreds of cell therapies per year—with very high production costs.

One solution to this conventional approach are closed system cell therapy machines that have been developed to attempt to address the shortcomings of the traditional approach. However, even this solution is still labor-intensive and inadequate to reach industrial scale. For instance, this solution can be described as an end-to-end serial system that is contained into a single machine. Different parts of the same machine perform the different steps of the production process. In other words, a single piece of equipment contains all the sub-systems that are needed to perform the cell manufacturing process. An intricate set of tubes connects all of these systems, so that the cell therapy product (which is typically in liquid form) can be transferred from one subsystem to the next without being exposed to the external environment, which provides the closed system.

However, these end-to-end, closed systems are sold as a unique piece of machinery. As such, the machinery cannot be modified by the buyer: once a system is bought, the buyer is constrained to run the exact process for which that machine was designed. Additionally, the machinery still needs to be operated by a highly skilled technician, who needs to perform a complicated set of actions to set up, monitor, and manage the manufacturing process. More specifically, highly trained operators set up the intricate network of tubes that is required by each batch. These operators are also tasked with opening and closing the valves that regulate the flow of material from one part of the system to the next. Furthermore, technicians also manually sample the batch, whenever testing is needed for quality control.

As such, this prior closed system solution suffers disadvantages, in that the closed system solution is overcomplicated. Setting up dozens of tubes, liquid reservoir bags, and reagents requires highly trained labor. This setting up process also takes a long time—even for a skilled technician—to set up, operate, and supervise the machinery. This results in the need for a number of operators that increases proportionally to the number of production system—making it impossible to achieve industrial scale and contain manufacturing costs.

Furthermore, the prior closed system solution is inefficient. Since the architecture of the closed system is still serial, this approach suffers of the same efficiency constraints as the dominant (bench-based) approach. At any given time, most of the subsystems inside of the end-to-end machine are unused. This happens because only one system can be used at a time—this is a serial production line with the hard limit of a single product per production run. Moreover, since some parts of the process are particularly slow (for example, the expansion of the cells into a bioreactor), the subsystems are characterized by an even lower utilization rate than the slower subsystems of the machinery.

Additionally, this closed system lacks design flexibility. This inflexibility drawback is typical of closed systems that are built specifically to execute a particular process. Once the machinery is bought, it is not possible to replace an outdated subsystem with a better one (for example, a subsystem that performs a task better, or with a higher throughput). Any modification to the original closed system machinery requires massive engineering and retooling costs, comparable to building a whole new end-to-end system from scratch. This lack of flexibility is particularly disadvantageous in the case of cell therapy manufacturing—where processes are often tuned and improvement at all stages of clinical development.

Moreover, since each closed system is end-to-end and can only manufacture a single product at a time, the only way to increase throughput is to buy more of these closed systems. This in turn worsens the above-mentioned complexity and underutilization problems. In other words, deploying more complex systems increases the need for skilled operators, which in turn increases the cost of manufacturing. Since each machine is largely underutilized (only one subsystem is active at any given time), chronic underutilization also characterizes a facility that is equipped with multiple end-to-end systems.

Additionally, a major problem of labor-based cell manufacturing processes is that human operators need to sample each batch manually. In cell manufacturing processes, sterility must be always ensured. This is particularly important, because cell therapies cannot be sterilized at the end of the manufacturing process (that would kill the cells). At the same time, guaranteeing the quality of cell manufacturing processes requires a large number of quality control steps. And, in order to perform quality control tests, the cell therapy products must be frequently sampled (e.g., a part of the product must be removed from the batch, while ensuring the sterility of both the sample and the product). In conventional cell manufacturing processes, sampling tasks are executed by human operators.

One disadvantage of this conventional approach to sampling is that human operators are a significant potential source of contamination for cell therapy products. Every time a batch is sampled manually, there is a high risk of contamination because the operator must manually remove a part of the liquid containing the cell product. Even semi-automated sampling procedures, where an operator activates a system that performs the sampling task, present significant risk of contamination due to requiring the presence of a human technicians in close proximity to the process.

Another critical issue is that sampling procedures are performed extremely frequently in cell manufacturing processes. Cell therapy products are sometimes sampled multiple times during a single day. Since cell manufacturing processes have a long completion time (most require more than a week, and many can take up to fifteen to twenty days), manual sampling is repeated dozens of times for every single batch. Repeating risky sampling procedures with this extreme frequency greatly increases the risk of contamination.

Given the above background, there is a need in the art for improved systems, methods, and apparatuses for facilitating an improved manufacture of cell therapies that addresses these dilemmas.

The information disclosed in this background section is only for enhancement of understanding of the general background of the invention and should not be taken as an acknowledgement or any form of suggestion that this information forms the prior art already known to a person skilled in the art.

SUMMARY

To address the shortcomings discussed above and/or other issues, the present disclosure provides apparatuses that facilitate automated loading and/or unloading a consumable kit to an instrument. An apparatus generally includes a dock for securing an instrument and a cartridge for holding a consumable kit. In various embodiments, the cartridge can be gripped by a robot (e.g., a robotic end of arm tool) and moved to or away from the dock by the robot on demand. Moreover, the cartridge can be aligned and locked with the dock to ensure the consumable kit installed properly or precisely on the instrument without any human involvement. As such, the apparatuses of the present disclosure advantageously leverage advanced robotic features and technologies while retaining the benefits of conventional closed-system processes (e.g., providing a sterile clean room environment). This enables the transformation of cellular engineering target manufacturing from labor-based and low-throughput processes to fully industrialized, high-throughput processes with high scale, efficiency and repeatability.

In various embodiments, the present disclosure provides an apparatus for facilitating automated loading of a consumable kit to an instrument. The apparatus includes a cartridge and a dock. The cartridge includes a mounting member, a plurality of first docking members, and a plurality of first locking members. The mounting member is configured for holding the consumable kit at a rear side of the mounting member. The plurality of first docking members is coupled to or formed with the mounting member, and the plurality of first locking members is coupled to or formed with the mounting member. The dock is configured for securing the instrument. The dock includes a frame, a plurality of second docking members, and a plurality of second locking members. The frame is configured for surrounding at least a portion of a perimeter of the instrument at or adjacent to a front surface of the instrument. The plurality of second docking members is coupled to or formed with the frame. In some such embodiments, each respective second docking member in the plurality of second docking members is configured to removably couple with a corresponding first docking member in the plurality of first docking members. Coupling of each respective second docking member in the plurality of second docking members with the corresponding first docking member in the plurality of first docking members (a) restricts the mounting member of the cartridge from moving relative to the frame in a plane parallel or substantially parallel to the front surface of the instrument, and (b) allows the mounting member of the cartridge to move relative to the frame in a first direction perpendicular or substantially perpendicular to the front surface of the instrument. The plurality of second locking members is coupled to the frame. In some such embodiments, each respective second locking member in the plurality of second locking members is operably movable relative to the frame between a corresponding first position and a corresponding second position to selectively engage with or disengage from a corresponding first locking member in the plurality of first locking members. Engagement of each respective second locking member in the plurality of second locking members with the corresponding first locking member in the plurality of first locking members pushes the mounting member of the cartridge toward the front surface of the instrument and locks the mounting member of the cartridge with the frame of the dock.

In some embodiments, the instrument is a counterflow centrifugation system or the consumable kit is a closed system kit.

In some embodiments, the cartridge further includes a plurality of tube retaining sets. In such embodiments, each respective tube retaining set in the plurality of tube retaining sets includes one or more corresponding tube retaining members disposed at the rear side of the mounting member and configured to retain a corresponding tube in a plurality of input or output tubes of the consumable kit.

In some embodiments, the one or more corresponding tube retaining members of each respective tube retaining set are disposed respectively at one or more corresponding locations on the rear side of the mounting member such that engagement of each respective second locking member in the plurality of second locking members with the corresponding first locking member in the plurality of first locking members pushes the corresponding tube in the plurality of input and output tubes of the consumable kit into a corresponding tubing track in a plurality of tubing tracks formed at the front surface of the instrument.

In an exemplary embodiment, each of the one or more corresponding tube retaining members of a respective tube retaining set is a mechanical fastener.

In some embodiments, the mounting member of the cartridge includes a plurality of holes or windows for visualizing flow in the plurality of input or output tubes of the consumable kit.

In some embodiments, the cartridge further includes a first interface member connected to or formed with the mounting member. The first interface member is configured for facilitating moving of the mounting member to or from the dock.

In an exemplary embodiment, the first interface member includes a first interface surface, a second interface surface, an elongated slot, and a recess. The first interface surface is accessible from a front side of the mounting member and is substantially planar. The second interface surface is opposite to the first interface surface. The elongated slot is formed through the first interface surface to allow an elongated cam bar of a robotic end of arm tool (EOAT) to insert into the first interface member. The recess is recessed from the second interface surface toward the first interface surface, wherein the recess has a dimension larger than a width of the elongated slot and a length of the elongated cam bar, thereby allowing the elongated cam bar of the EOAT to rotate and engage with the first interface member.

In some embodiments, the cartridge further includes a plurality of port units connected to the mounting member. In some such embodiments, each respective port unit in at least a subset of the plurality of port units is fluidly connected to a corresponding tube in a plurality of input and output tubes of the consumable kit.

In an exemplary embodiment, each of the plurality of first docking members includes a bushing, and each of the plurality of second docking members includes a post to removably couple with the bushing.

In some embodiments, each of the plurality of first locking members includes a ramp having a sloping surface with respect to the front surface of the instrument, and each of the plurality of second locking members includes a ramp follower operably movable on the sloping surface.

In some embodiments, the dock further includes a set of rails and a set of slides. Each rail in the set of rails is fixed on or formed with the frame. Each respective slide in the set of slides is coupled to a corresponding rail in the set of rails and operably movable along the corresponding rail. In some such embodiments, one or more second locking members in the plurality of second locking members are connected to or formed with each of the set of slides.

In some embodiments, the dock further includes a set of cam assemblies connected to the frame. In some such embodiments, an end portion of each respective slide in the set of slides is coupled to a corresponding cam assembly in the set of cam assemblies and the corresponding cam assembly converts a rotary motion to a linear motion of the respective slide.

In an exemplary embodiment, the plurality of first locking members includes four first locking members with two first locking members on each of a left side and a right side of the mounting member. The set of rails includes a left rail on a left side of the frame and a right rail on a right side of the frame. The set of slides includes a left slide coupled to the left rail and a right slide coupled to the right rail. The plurality of second locking members includes four second locking members with two second locking members on each of the left rail and the right rail.

In some embodiments, the dock further includes a plurality of face reference members disposed at a front surface of the frame. In some such embodiments, each of the plurality of face reference members includes a suspension beyond an inner edge of the frame to abut the front surface of the instrument, thereby aligning the front surface of the frame with the front surface of the instrument.

In an exemplary embodiment, each of the plurality of face reference members includes a pin fastened to the frame, wherein the pin is elongated in a direction parallel or substantially parallel to the front surface of the frame.

In some embodiments, the dock further includes a base for holding the instrument; and a plurality of upright members fixed on the base to support the frame such that the frame is disposed at a first angle with respect to the base.

In an exemplary embodiment, the dock further includes a plurality of stoppers fixed on the base, each adjustable and configured for abutting a wall of the instrument.

In some embodiments, the dock further includes a pump tube loading assembly connected to the frame and configured for placing at least a portion of a pump tube of the consumable kit into a peristaltic pump head of the instrument. The pump tube loading assembly includes a loading member and a driving unit. The loading member includes (i) a platform having a sector-shape or a substantial sector-shape and (ii) a finger disposed at or adjacent to a circumferential edge of the platform and extended toward the instrument beyond the platform. The driving unit is configured to rotate the loading member, thereby causing the finger to press at least the portion of the pump tube of the consumable kit into a peristaltic pump head to get it seated on rollers of the peristaltic pump head of the instrument and using the platform to prevent at least the portion of the pump tube of the consumable kit from popping out of the peristaltic pump head.

In an exemplary embodiment, the driving unit rotates the loading member around a rotational axis of the platform that is aligned with an axis of the peristaltic pump head of the instrument.

In some embodiments, the driving unit includes a plurality of shafts coupled to each other by a timing belt.

In some embodiments, the apparatus further includes a capsule releasing member and a second interface member. The capsule releasing member is configured for unlocking a centrifuge capsule of the consumable kit from a centrifuge chamber carrier of the instrument. The second interface member is connected to or formed with the capsule releasing member. The second interface member is robot-operable, thereby facilitating moving of the capsule releasing member relative to the instrument.

In an exemplary embodiment, the capsule releasing member includes a first jaw and a second jaw. The first jaw is insertable through a first hole formed on the mounting member and configured to grip the centrifuge capsule of the consumable kit. The second jaw is insertable through a second hole formed on the mounting member and configured to lift a lever in the centrifuge chamber carrier of the instrument, thereby unlocking the centrifuge capsule of the consumable kit from a centrifuge chamber carrier of the instrument.

In various embodiments, the present disclosure provides an apparatus for facilitating automated loading of a consumable kit to an instrument. The apparatus includes a cartridge and a dock. The cartridge is configured for holding the consumable kit and is movable by a robot. The dock is configured for securing the instrument. The dock includes a base, a frame, a plurality of upright members, and a plurality of face reference members. The base is configured for holding the instrument. The frame is configured for surrounding at least a portion of a perimeter of the instrument at or adjacent to a front surface of the instrument. The plurality of upright members is fixed on the base to support the frame such that the frame is disposed at a first angle with respect to the base. The plurality of face reference members is disposed at a front surface of the frame. In some such embodiments, each of the plurality of face reference members includes a suspension beyond an inner edge of the frame to abut the front surface of the instrument, thereby aligning the front surface of the frame with the front surface of the instrument.

In some embodiments, each of the plurality of face reference members includes a pin that is parallel or substantially parallel to the front surface of the frame and fastened to the frame.

In an exemplary embodiment, the dock further includes a plurality of stoppers fixed on the base, each adjustable and configured for abutting a wall of the instrument.

In various embodiments, the present disclosure provides an apparatus for facilitating automated loading of a consumable kit to an instrument. The apparatus includes a cartridge and a dock. The cartridge is configured for holding the consumable kit and is movable by a robot. The dock is configured for securing the instrument. The dock includes a frame and a pump tube loading assembly. The frame is configured for surrounding at least a portion of a perimeter of the instrument at or adjacent to a front surface of the instrument. The pump tube loading assembly is connected to the frame and configured for placing at least a portion of a pump tube of the consumable kit into a peristaltic pump head of the instrument. The pump tube loading assembly includes a loading member and a driving unit. The loading member includes (i) a platform having a sector-shape or a substantial sector-shape and including a retaining surface that faces the instrument, wherein the retaining surface is parallel or substantially parallel to the front surface of the instrument, and (ii) a finger disposed at or adjacent to a circumferential edge of the platform and extended toward the instrument beyond the retaining surface of the platform. The driving unit is configured to rotate the loading member, thereby causing the finger to press at least the portion of the pump tube of the consumable kit into a peristaltic pump head to seat on rollers of the peristaltic pump head of the instrument and causing the platform to confine at least the portion of the pump tube of the consumable kit to prevent the pump tube of the consumable kit from popping out of the peristaltic pump head.

In some embodiments, the driving unit rotates the loading member around a rotational axis of the platform that is aligned with an axis of the peristaltic pump head of the instrument.

In various embodiments, the present disclosure provides an apparatus for facilitating automated loading of a consumable kit to an instrument. The apparatus includes a cartridge and a dock. The cartridge is movable by a robot and includes a mounting member, a plurality of first locking members, and a plurality of tube retaining sets. The mounting member is configured for holding the consumable kit at a back side of the mounting member. The plurality of first locking members is coupled to or formed with the mounting member. Each respective tube retaining set in the plurality of tube retaining sets includes one or more corresponding tube retaining members disposed at the back side of the mounting member and configured to retain a corresponding tube in a plurality of input and output tubes of the consumable kit. The dock is configured for securing the instrument and includes a frame and a plurality of second locking members. The frame is configured for surrounding at least a portion of a perimeter of the instrument at or adjacent to a front surface of the instrument. The plurality of second locking members is coupled to the frame. In some such embodiments, each respective second locking member in the plurality of second locking members is configured to selectively engage with or disengage from a corresponding first locking member in the plurality of first locking members. The one or more corresponding tube retaining members of each respective tube retaining set are disposed respectively at one or more corresponding locations on the back side of the mounting member such that engagement of each respective second locking member in the plurality of second locking members with the corresponding first locking member in the plurality of first locking members pushes the corresponding tube in the plurality of input and output tubes of the consumable kit into a corresponding tubing track in a plurality of tubing tracks formed at the front surface of the instrument.

In some embodiments, the dock further includes a pump tube loading assembly connected to the frame and configured for placing at least a portion of a pump tube of the consumable kit around a peristaltic pump head of the instrument. The pump tube loading assembly includes a loading member and a driving unit. The loading member includes (i) a platform having a sector-shape or a substantial sector-shape and (ii) a finger disposed at or adjacent to a circumferential edge of the platform and extended toward the instrument beyond the platform. The driving unit is configured to rotate the loading member, thereby causing the finger to press at least the portion of the pump tube of the consumable kit into a peristaltic pump head to get it seated on rollers of the peristaltic pump head of the instrument and using the platform to prevent at least the portion of the pump tube of the consumable kit from popping out of the peristaltic pump head.

The methods and apparatuses of the present disclosure have other features and advantages which will be apparent from or are set forth in more detail in the accompanying drawings, which are incorporated herein, and the following Detailed Description, which together serve to explain certain principles of the present invention.

BRIEF DESCRIPTION OF THE DRAWINGS

FIG. 1A shows a commercially available instrument.
FIG. 1B shows a commercially available single-use kit.
FIG. 1C shows the single-use kit of FIG. 1B installed on the instrument of FIG. 1A.
FIG. 5A is a side view illustrating an exemplary pump tube loading assembly in accordance with some exemplary embodiments of the present disclosure.
FIG. 5B is a perspective view illustrating the exemplary pump tube loading assembly of FIG. 5A, in which a cover is removed to show some interior components of exemplary pump tube loading assembly in accordance with some exemplary embodiments of the present disclosure.

Figure 2A:
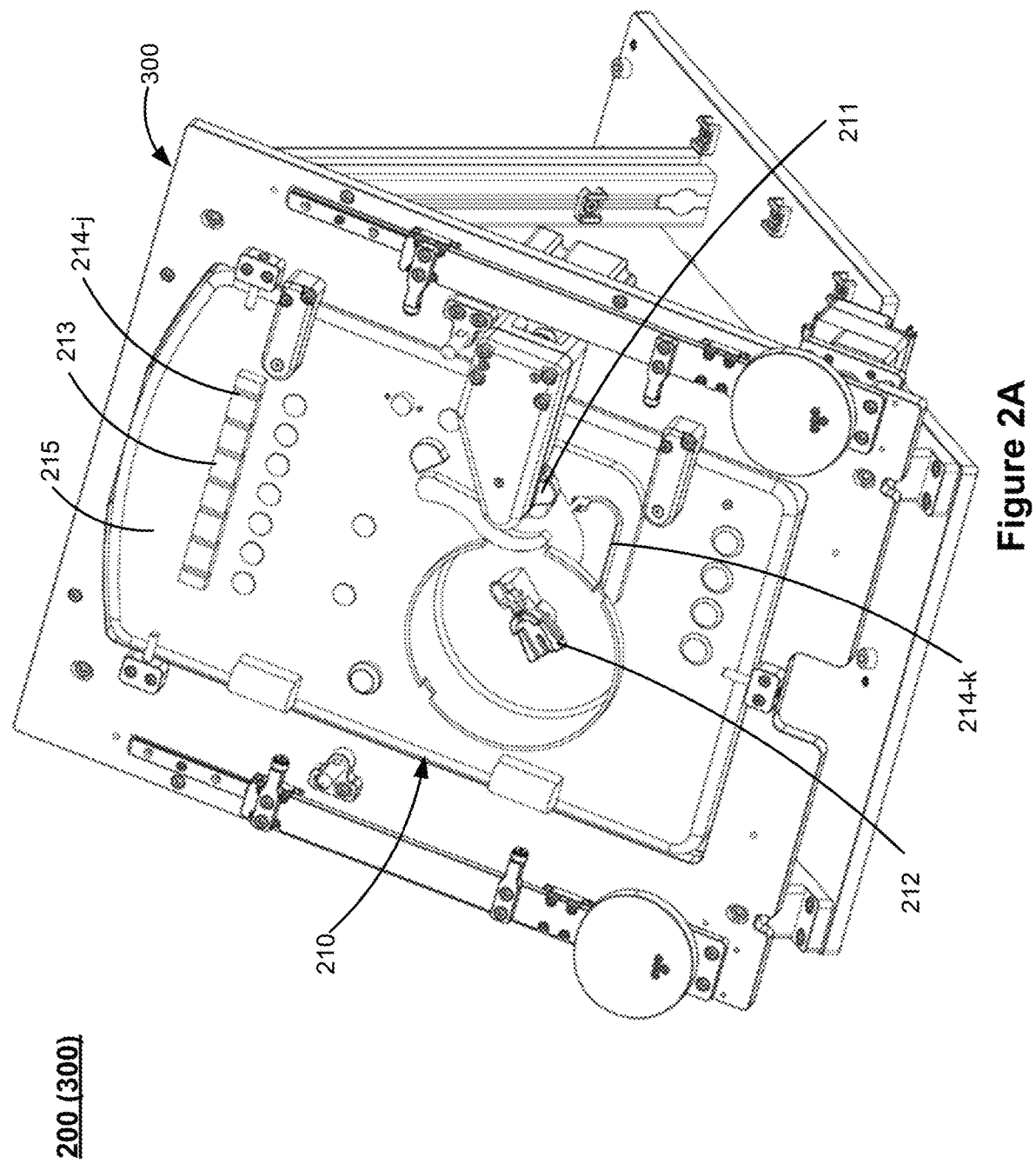
FIG. 2A is a perspective view illustrating an exemplary dock of an exemplary apparatus, in which an instrument is secured on the exemplary dock, in accordance with some exemplary embodiments of the present disclosure.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

The present disclosure provides apparatuses that can facilitate automated loading and/or unloading a consumable kit to an instrument. An apparatus generally includes a dock for securing an instrument and a cartridge for holding a consumable kit. In various embodiments, the cartridge can be gripped by a robot (e.g., a robotic end of arm tool) and moved to or away from the dock by the robot on demand. Moreover, the cartridge can be aligned and locked with the dock to ensure the consumable kit installed properly or precisely on the instrument without any human involvement. As such, the apparatuses of the present disclosure advantageously leverage advanced robotic features and technologies while retaining the benefits of conventional closed-system processes (e.g., providing a sterile clean room environment). This enables the transformation of cellular engineering target manufacturing from labor-based and low-throughput processes to fully industrialized, high-throughput processes with high scale, efficiency and repeatability.

Reference will now be made in detail to various embodiments of the present disclosure, examples of which are illustrated in the accompanying drawing and described below. While the disclosure will be described in conjunction with exemplary embodiments, it will be understood that the present description is not intended to limit the invention(s) to those exemplary embodiments. On the contrary, the invention(s) is/are intended to cover not only the exemplary embodiments, but also various alternatives, modifications, equivalents and other embodiments, which may be included within the spirit and scope of the present invention as defined by the appended claims.

It will also be understood that, although the terms first, second, etc. may be used herein to describe various elements, these elements should not be limited by these terms. These terms are only used to distinguish one element from another. For example, a first instrument could be termed a second instrument, and, similarly, a second instrument could be termed a first instrument, without departing from the scope of the present disclosure. The first instrument and the second instrument are both instruments, but they are not the same instrument.

The terminology used in the present disclosure is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and or "comprising," when used in this specification, specify the presence of stated features, integers, steps, operations, elements, and or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Furthermore, when a reference number is given an "i" denotation, the reference number refers to a generic component, set, or embodiment. For instance, an application termed "application i" refers to the $i^{th}$ application in a plurality of applications.

The term "about" or "approximately" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number. It should be appreciated that all numerical values and ranges disclosed herein are approximate values and ranges, whether "about" is used in conjunction therewith. It should also be appreciated that the term "about," as used herein, in conjunction with a numeral refers to a value that may be ±0.01% (inclusive), ±0.1% (inclusive), ±0.5% (inclusive), ±1% (inclusive) of that numeral, ±2% (inclusive) of that numeral, ±3% (inclusive) of that numeral, ±5% (inclusive) of that numeral, ±10% (inclusive) of that numeral, or ±15% (inclusive) of that numeral. It should further be appreciated that when a numerical range is disclosed herein, any numerical value falling within the range is also specifically disclosed.

For purposes of explanation, the description herein has been described with reference to specific implementations. However, the illustrative discussions are not intended to be exhaustive or to limit the implementations to the precise forms disclosed. Many modifications and variations are possible in view of the above teachings. The implementations are chosen and described in order to best explain the principles and their practical applications, to thereby enable others skilled in the art to best utilize the implementations and various implementations with various modifications as are suited to the particular use contemplated.

In the interest of clarity, not all of the routine features of the implementations described herein are shown and described. It will be appreciated that, in the development of any such actual implementation, numerous implementation-specific decisions are made in order to achieve the designer's specific goals, such as compliance with use case- and business-related constraints, and that these specific goals will vary from one implementation to another and from one designer to another. Moreover, it will be appreciated that such a design effort might be complex and time-consuming, but nevertheless be a routine undertaking of engineering for those of ordering skill in the art having the benefit of the present disclosure.

Referring to FIGS. 1A-1C, there is depicted a Rotea system 100 for cell processing applications, such as CAR-T therapy, stem cell therapy, and PBMC isolation. The system 100 includes an instrument 110 that utilizes counterflow centrifugation (CFC) to separate cells, aggregates, or beads based on size and to concentrate particles with certain outer diameters. In some embodiments, the instrument 110 includes a peristaltic pump 111, a chamber carrier 112, a bubble sensor strip 113, one or more tubing tracks 114, one or more other elements such as two kit location buttons, or a combination thereof. In some embodiments, the system 100 also includes a Rotea single-use kit 120 that can be used with the instrument 110 for cell processing applications. In some embodiments, he single-use kit 120 includes a pump tube 121, a centrifuge chamber or cone 122, a plurality of input/output tubes 123 (e.g., 8 input/output sterile weldable tubes), a tube management member 124, one or more other elements such as kit location button(s) and connector(s), or a combination thereof.

In some embodiments, to start a cell processing application, the single-use kit must be loaded to the instrument. Conventionally, this is done manually by a highly skilled technician who needs to perform a complicated set of actions. For instance, they have to (i) load the single-use kit start by hanging the bags in an order that best lines them up with the tube ports on the bubble sensor strip, (ii) line up the kit with the two kit location buttons, (iii) stretch the pump tubing around the peristaltic pump, (iv) press the bulb shape connector into place, (v) make sure the tubing over the pressure sensor is correctly placed in the tubing track, (vi) attach the centrifuge chamber or cone by lifting the silver lever in the chamber carrier and securing it by returning the lever to its upright position, (vii) press the tubing from each port on the kit into the tracks along the bubble sensor strip, (viii) make sure the bags aren't tangled so they can follow the protocol progress, and (ix) close the door (not shown) by pressing down on the door latch. In addition to requiring highly trained labor, this setting up process also takes a long time even for a skilled technician.

Figure 2B:
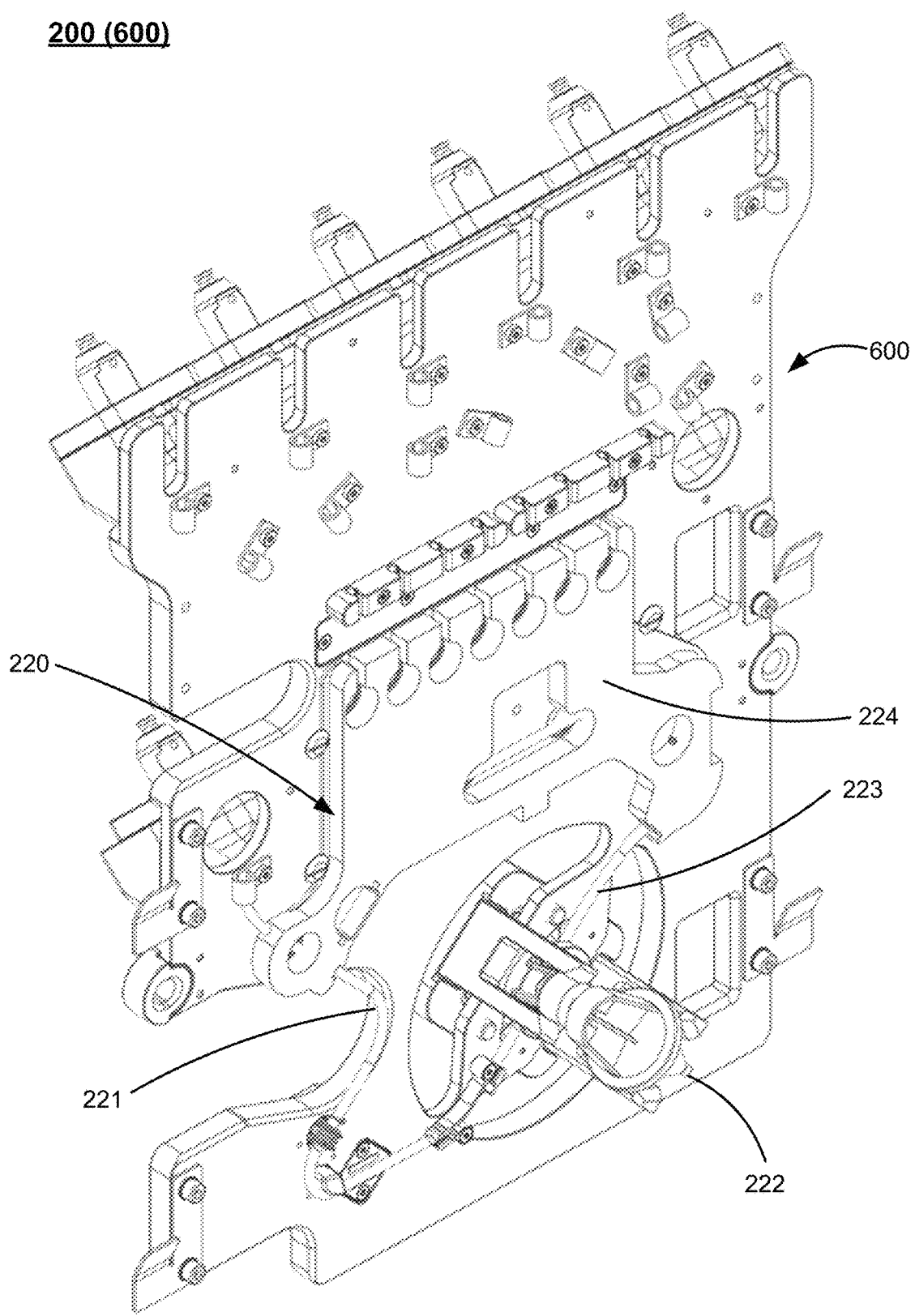
FIG. 2B is a perspective view illustrating an exemplary cartridge of an exemplary apparatus, in which a consumable kit is held by the exemplary cartridge, in accordance with some exemplary embodiments of the present disclosure.
Figure 3A:
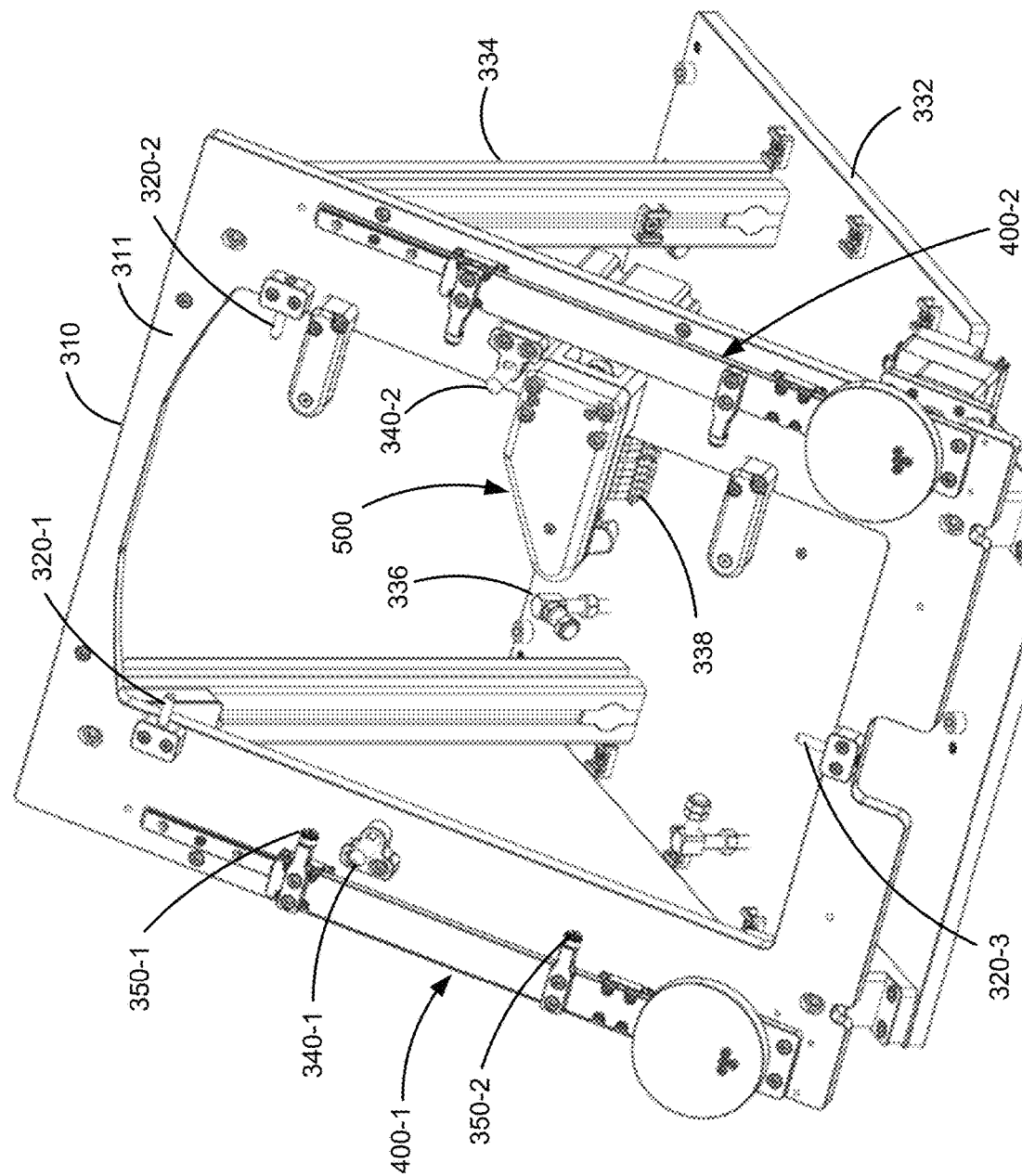
FIG. 3A is a perspective view illustrating an exemplary dock in accordance with some exemplary embodiments of the present disclosure.
Figure 3B:
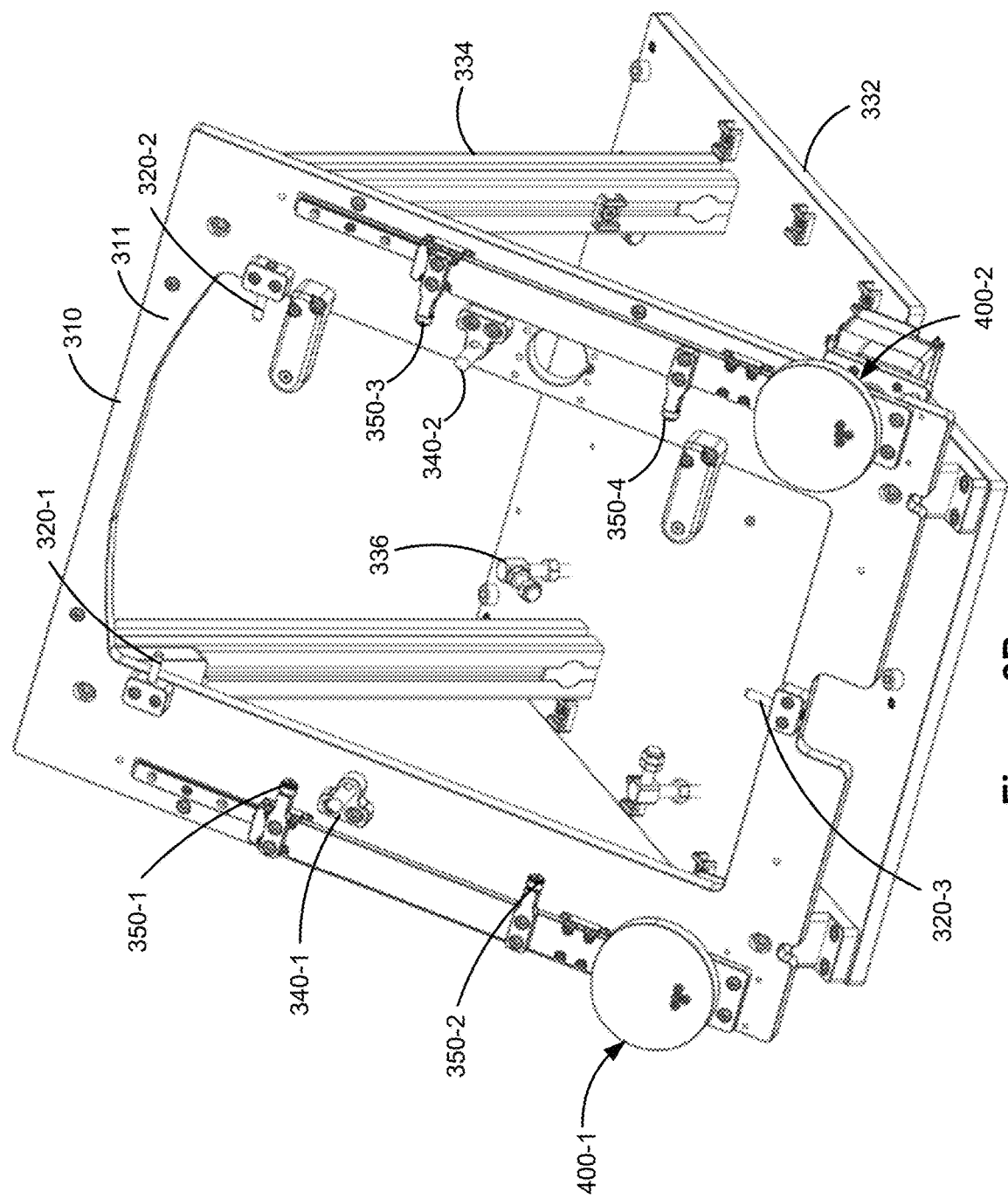
FIG. 3B is a perspective view illustrating the exemplary dock of FIG. 3A where some components are removed for clarity of illustration.
Figure 3C:
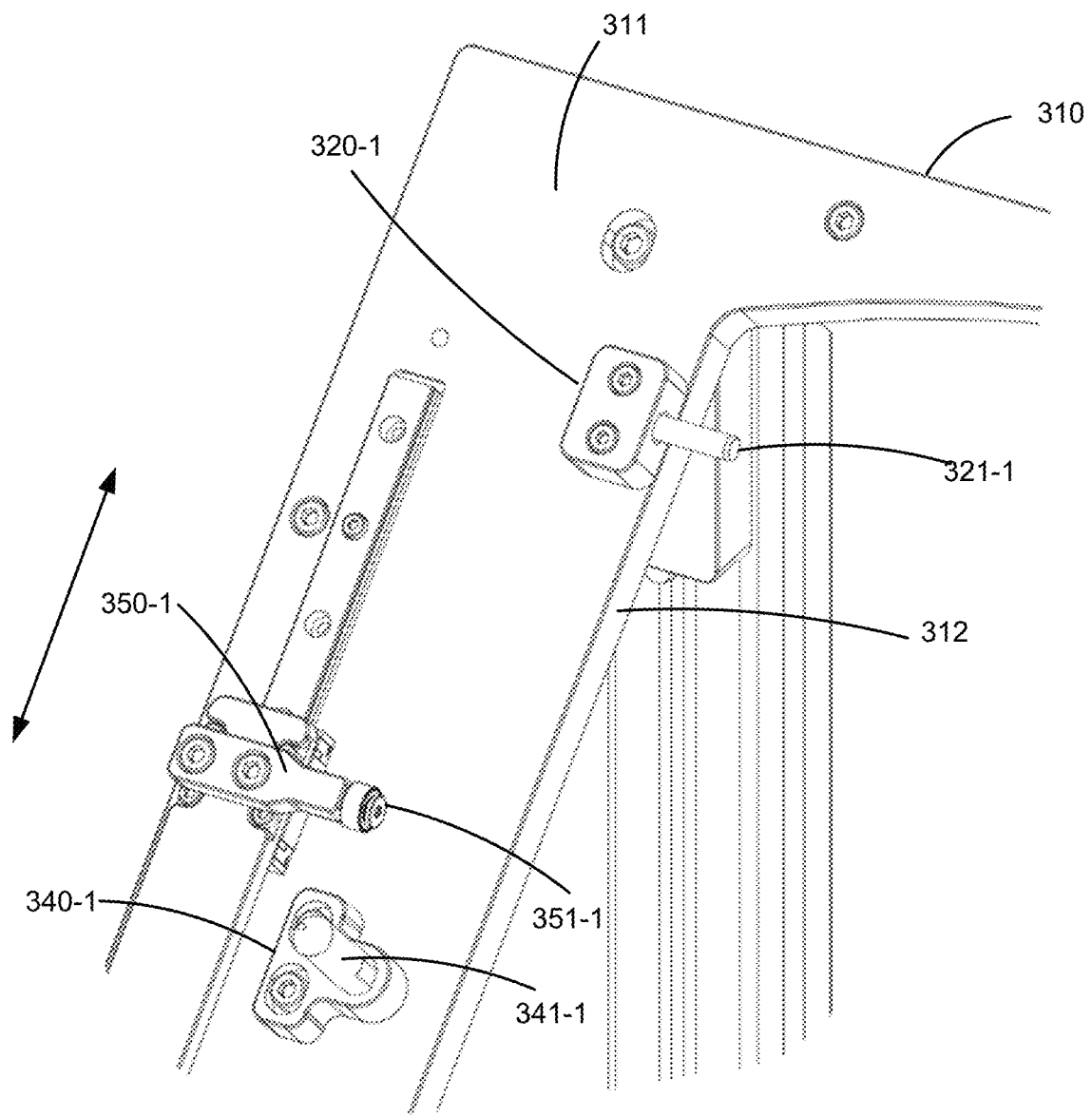
FIG. 3C is an enlarged view illustrating some components of the exemplary dock of FIG. 3A.
Figure 4A:
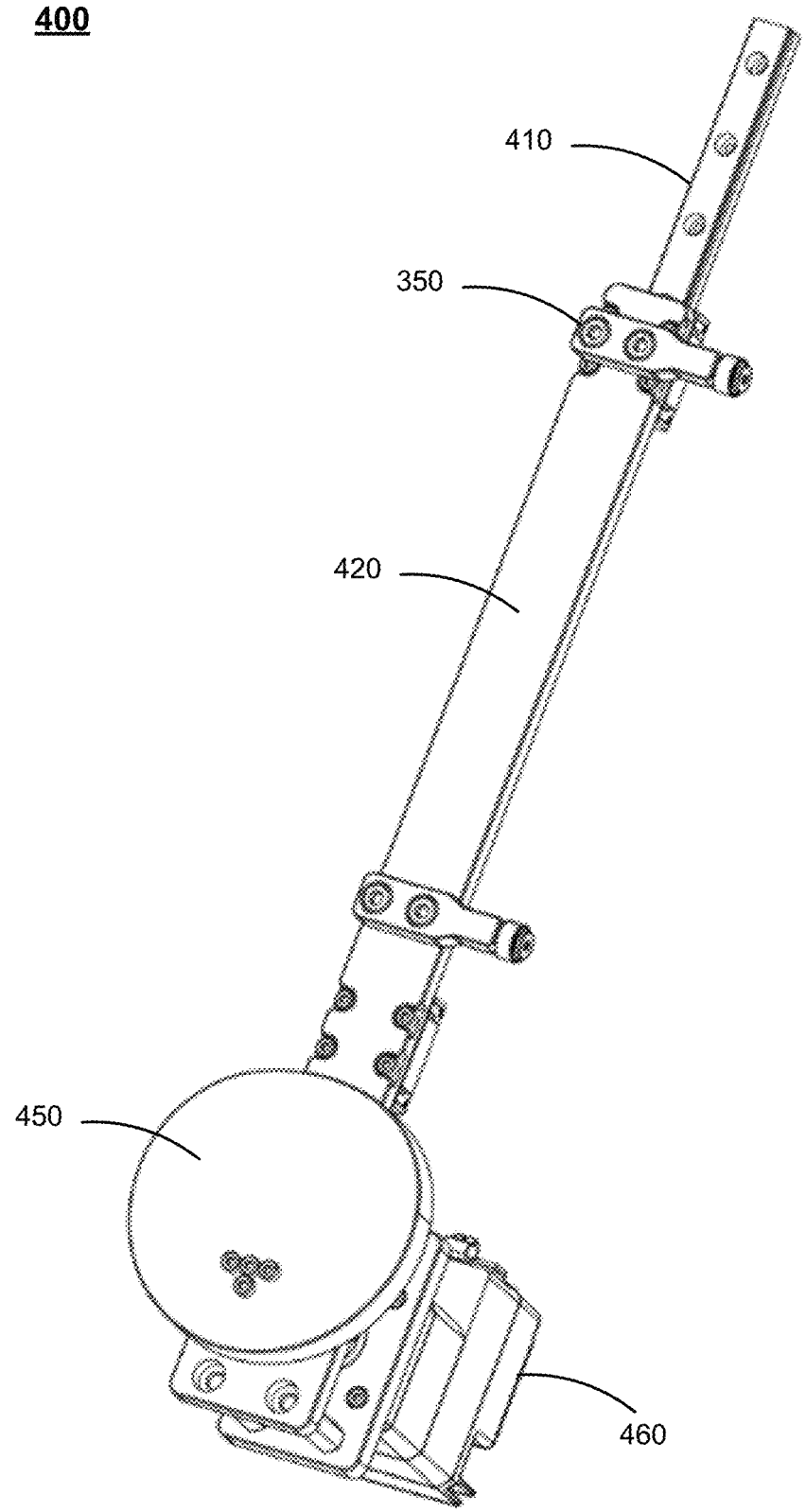
FIG. 4A is a perspective view illustrating an exemplary locking unit in accordance with some exemplary embodiments of the present disclosure.
Figure 4B:
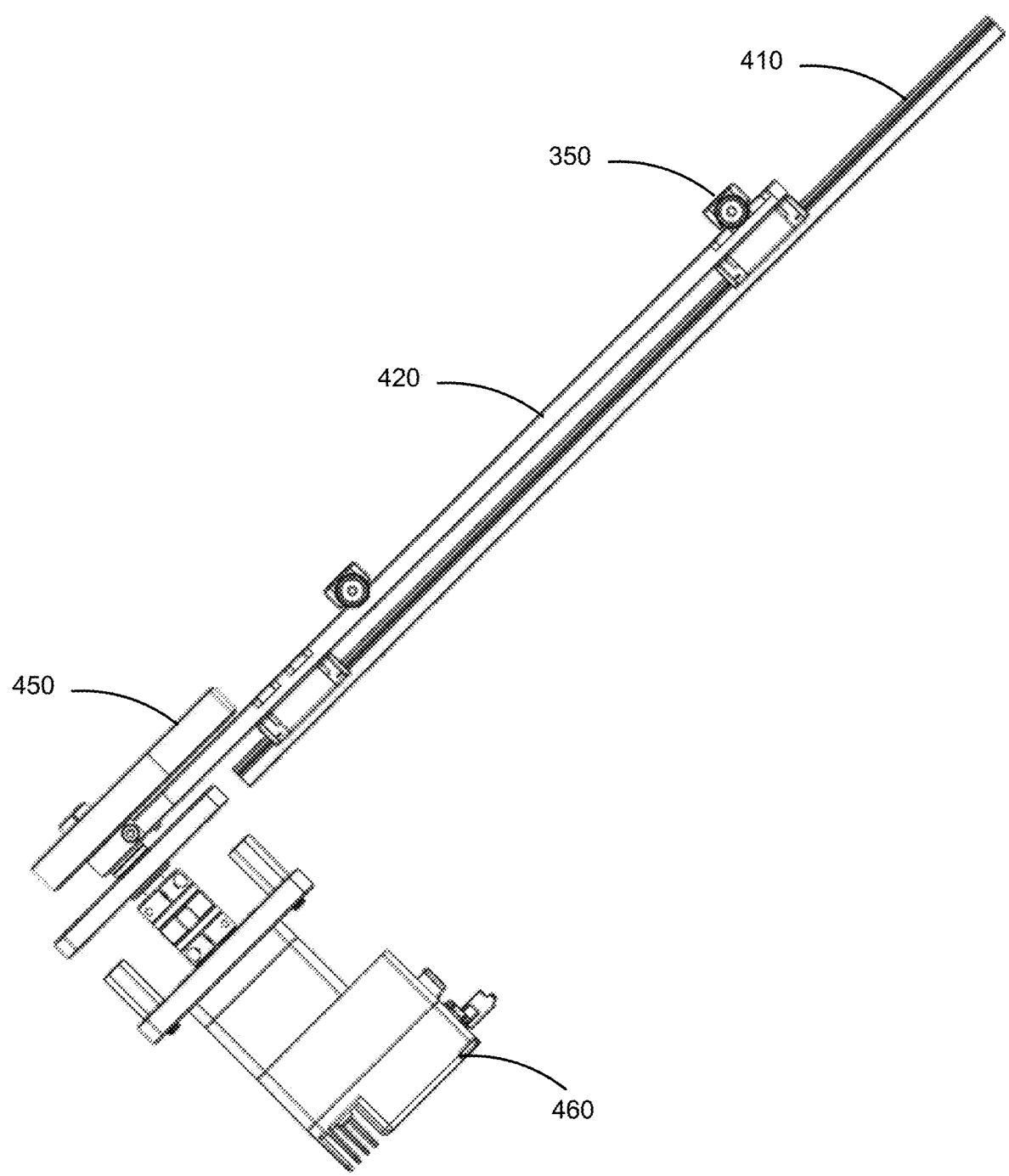
FIG. 4B is a side view illustrating the exemplary locking unit of FIG. 4A.
Figure 4C:
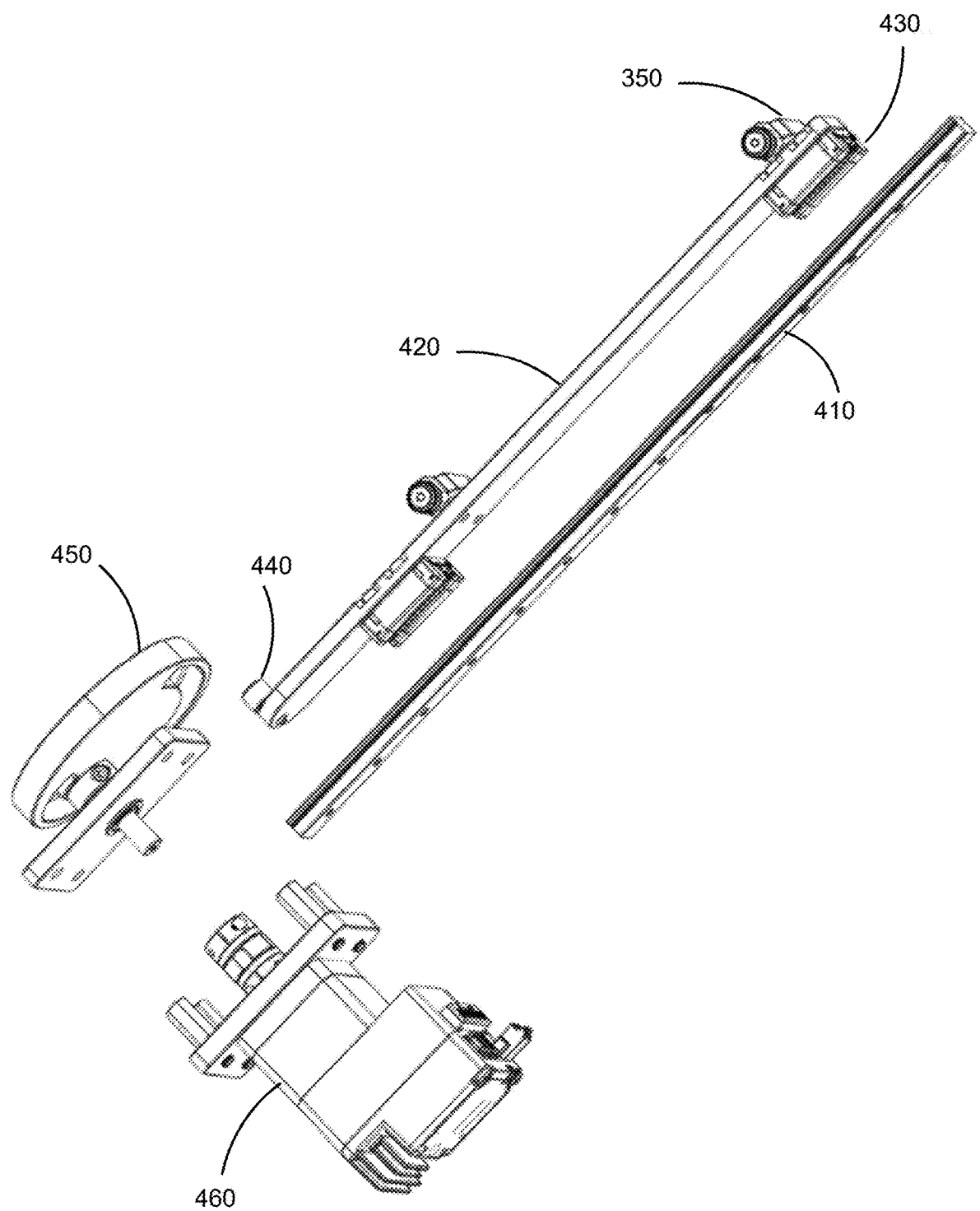
FIG. 4C is a partially exploded view illustrating the exemplary locking unit of FIG. 4A.
Figure 5D:
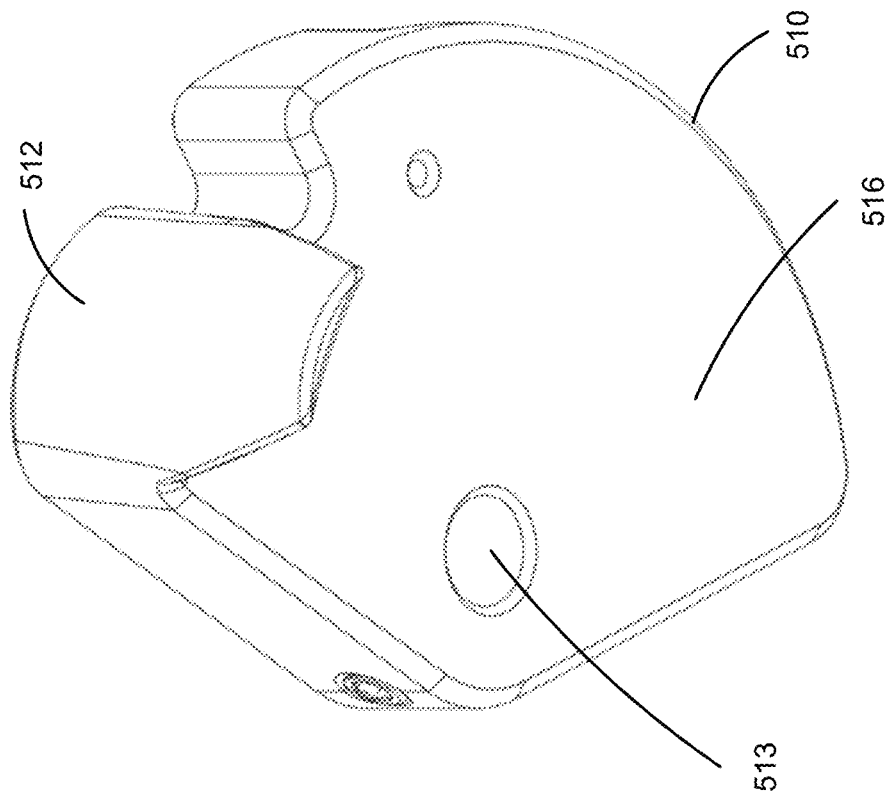
FIG. 5D is another perspective view illustrating the exemplary tube loading member of FIG. 5C.
Figure 5C:
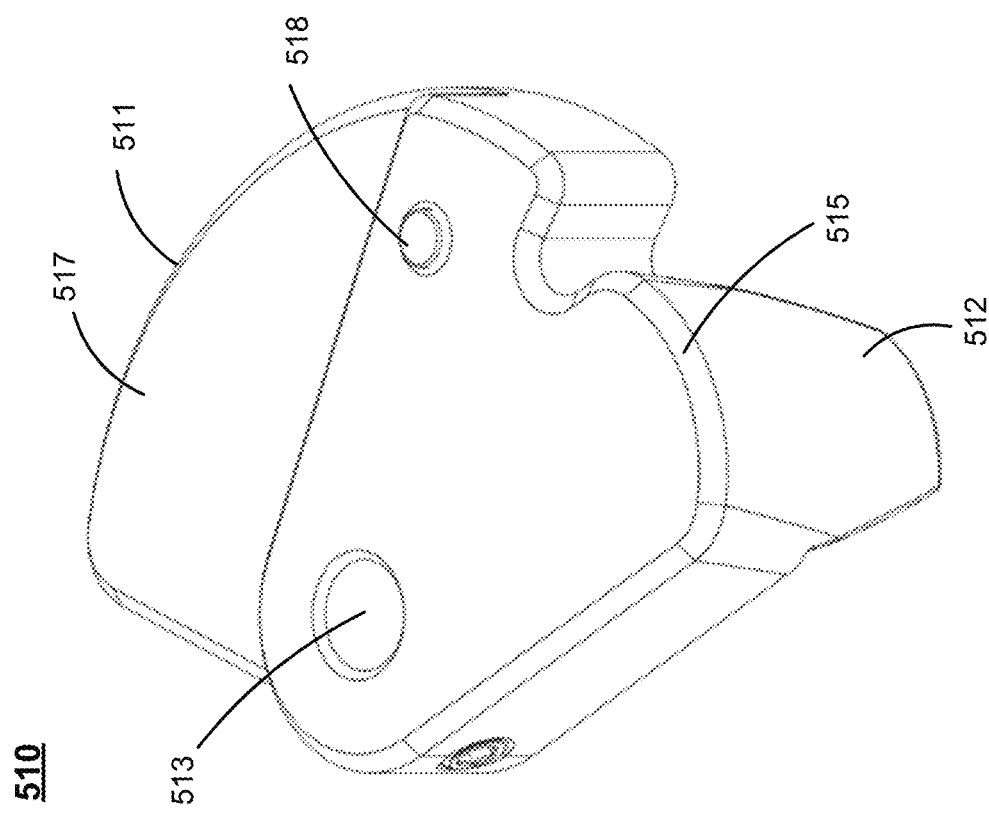
FIG. 5C is a perspective view illustrating an exemplary tube loading member in accordance with some exemplary embodiments of the present disclosure.
Figure 5F:
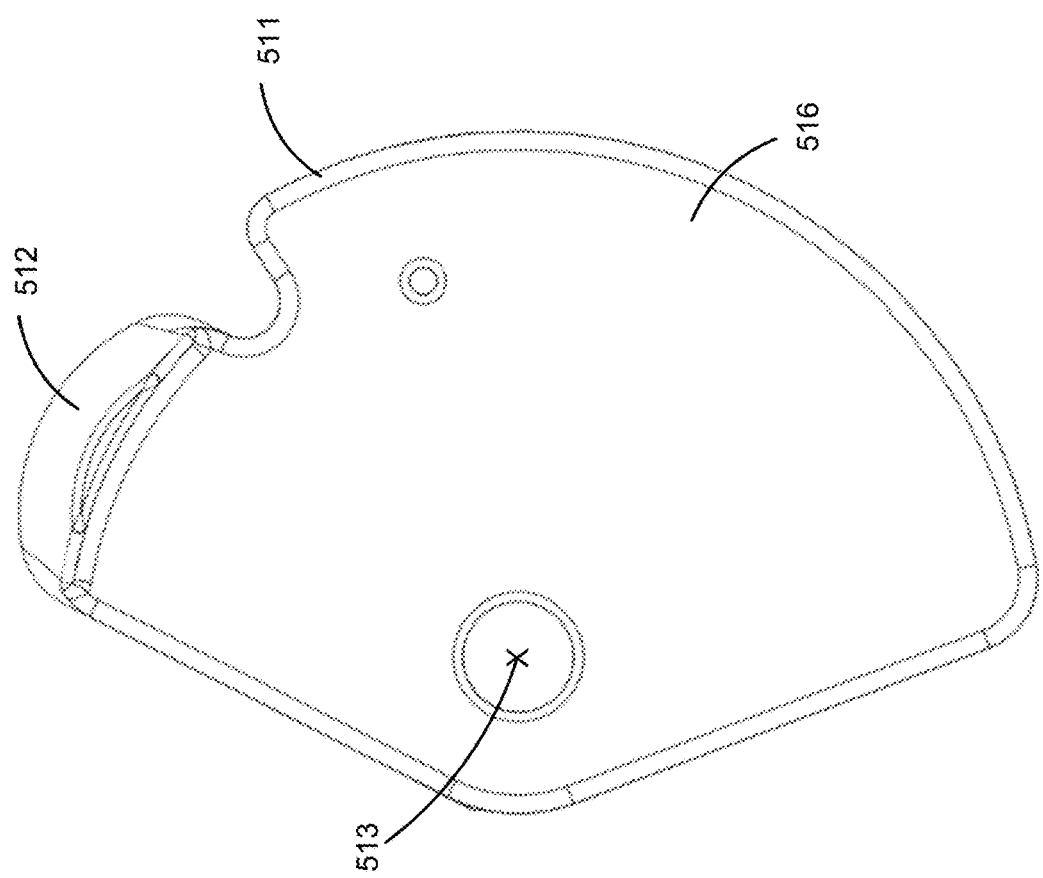
FIG. 5F is a bottom view illustrating the exemplary tube loading member of FIG. 5C.
Figure 5E:
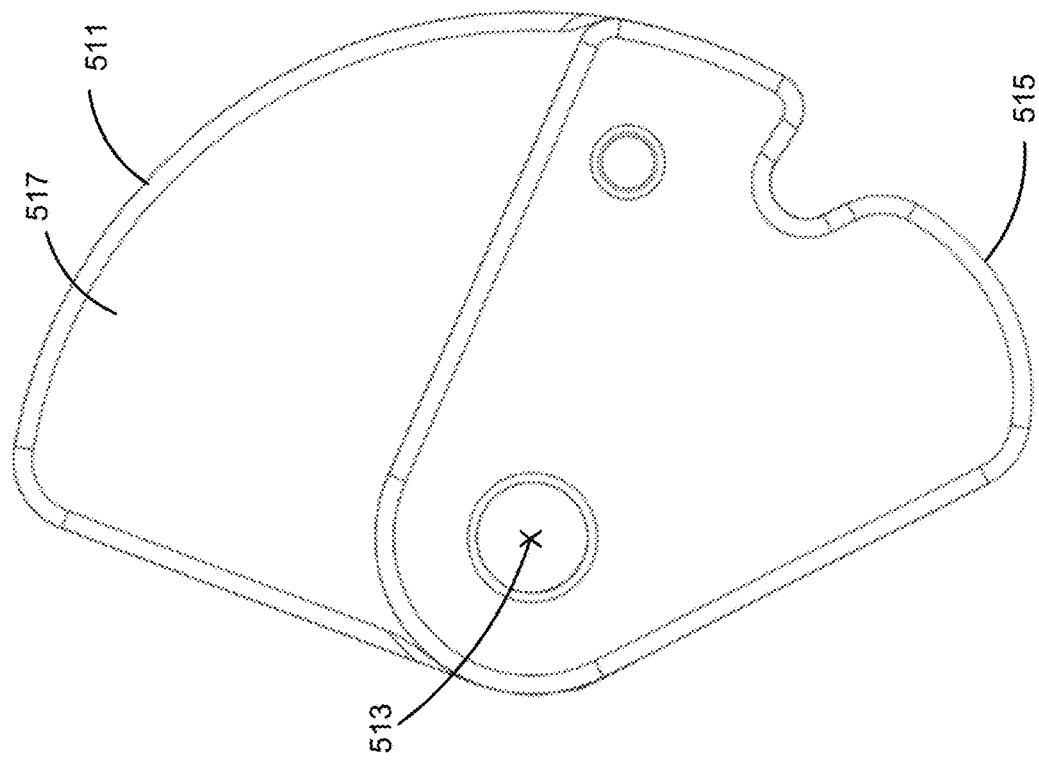
FIG. 5E is a top view illustrating the exemplary tube loading member of FIG. 5C.
Figure 5H:
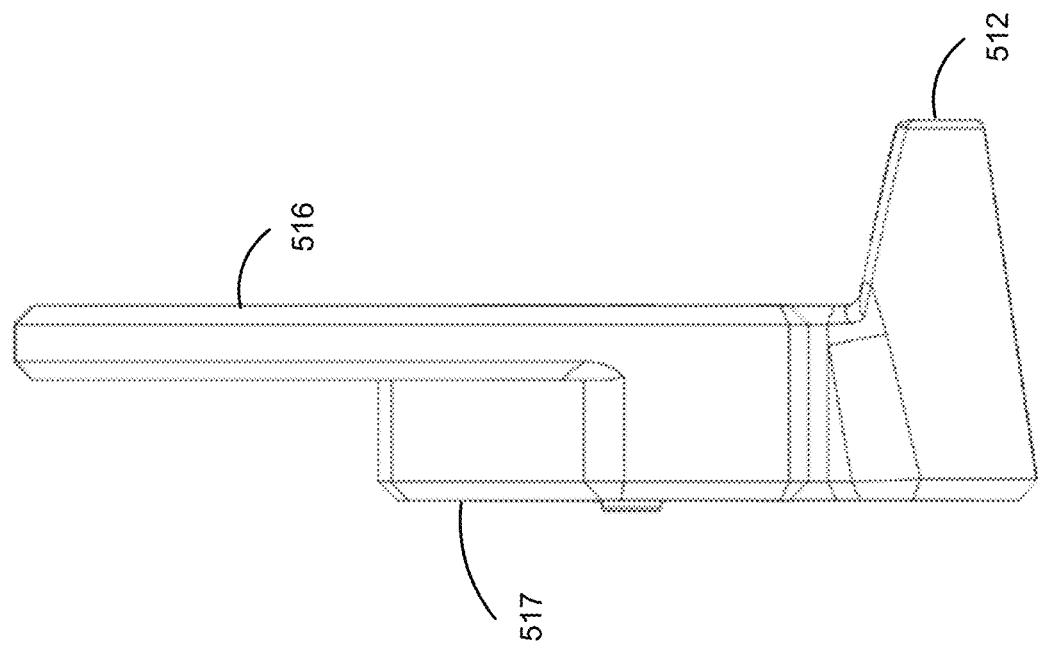
FIG. 5H is a second side view illustrating the exemplary tube loading member of FIG. 5C.
Figure 5G:
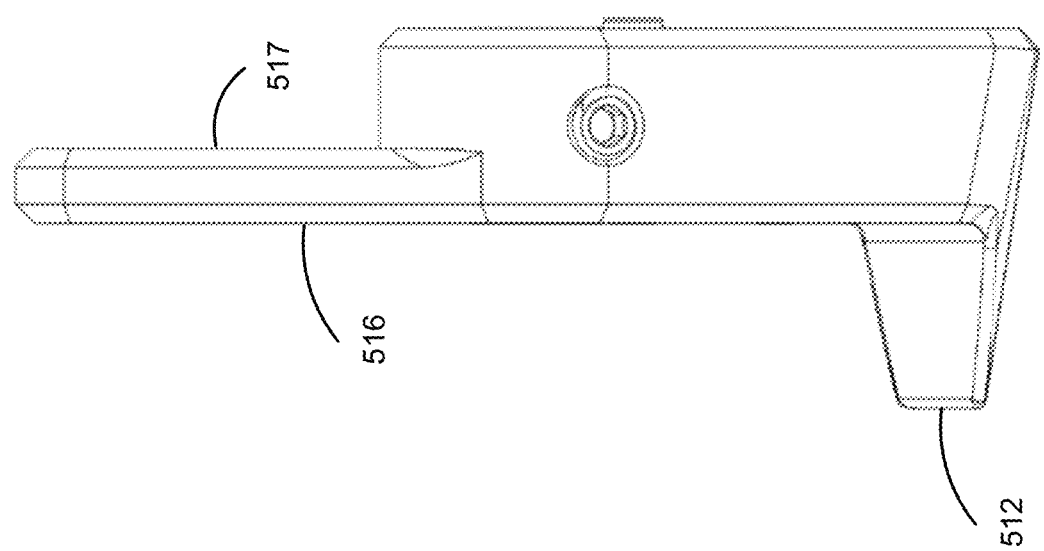
FIG. 5G is a first side view illustrating the exemplary tube loading member of FIG. 5C.
Figure 5J:
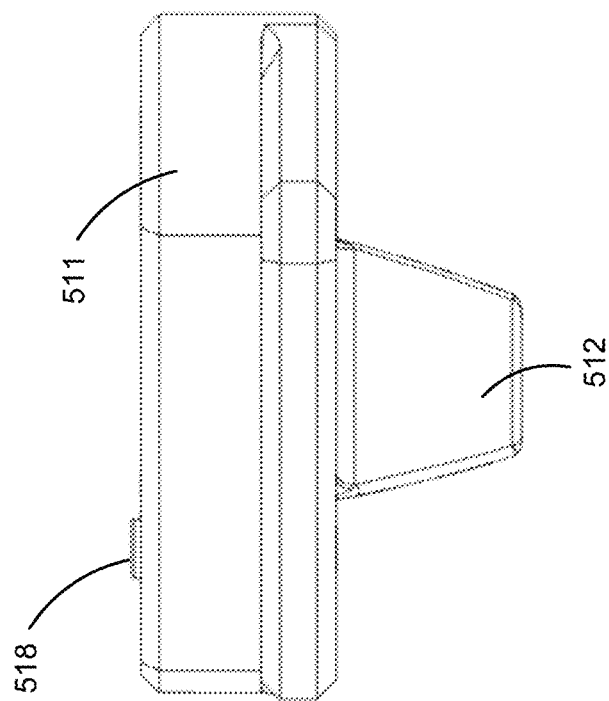
FIG. 5J is a fourth side view illustrating the exemplary tube loading member of FIG. 5C.
Figure 5I:
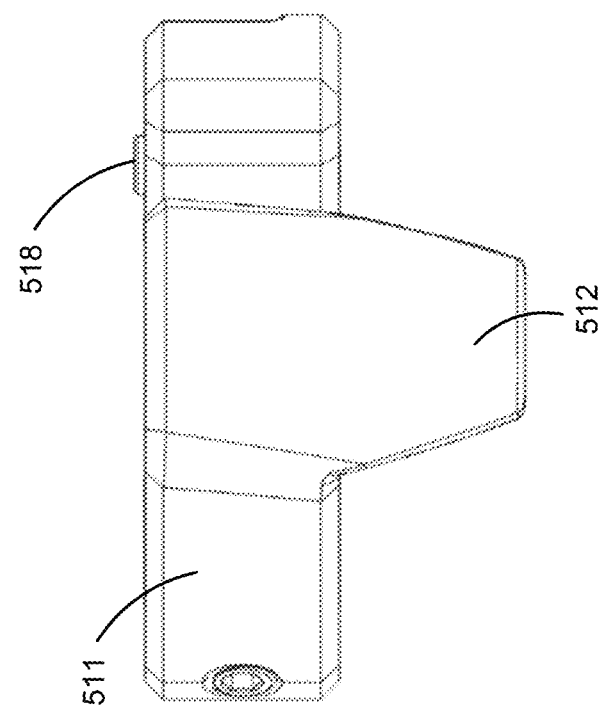
FIG. 5I is a third side view illustrating the exemplary tube loading member of FIG. 5C.

To address this and/or other issues, the present disclosure provides apparatuses to facilitate automated loading and/or unloading a consumable kit to an instrument. For instance, FIGS. 2A and 2B collectively illustrate an exemplary apparatus, generally designated 200, to facilitate automated loading and/or unloading a consumable kit (e.g., the consumable kit 220) to an instrument (e.g., the instrument 210) in accordance with some exemplary embodiments of the present disclosure. The instrument 210 can be but do not have to be the Rotea instrument 110. It can include a pump (e.g., a peristaltic pump), a carrier (e.g., a centrifuge carrier), one or more sensors (e.g., bubble sensor, pressure sensor), one or more tubing tracks, one or more kit location buttons, or any combination thereof. It can also include additional, optional, or alternative elements for cell processing applications. In some embodiments, it is a CFC machine. As a non-limiting example, FIG. 2B illustrates that the instrument 210 includes a peristaltic pump 211, a chamber carrier 212, a bubble sensor strip 213, a plurality of tubing tracks 214, and a front surface 215. Similarly, the consumable kit can be but do not have to be the Rotea single-use kit. It can include a pump tube, a centrifuge capsule (e.g., centrifuge chamber or cone), a plurality of input and/or output tubes, a tube management member, one or more connectors, or any combination thereof. It can also include additional, optional, or alternative elements for cell processing applications. In some embodiments, it is a closed system kit (e.g., a kit for use in a clean room environment). As a non-limiting example, FIG. 2A illustrates that the consumable kit 220 includes a pump tube 221, a centrifuge capsule (e.g., centrifuge chamber or cone) 222, a plurality of input and/or output tubes (for clarity of illustration, only a portion is shown) 223, and a tube management member 224.

As can be seen, the consumable kit includes flexible objects (e.g., tubes) and installation of the consumable kit requires proper handling of these flexible objects (e.g., putting a tube in a track, seating a tube around a head of a pump). Humans can handle this task because we have a fantastic ability to manipulate flexible objects and can control the objects' position in confined spaces with the advanced dexterity capabilities of our hands aided by our sense of touch, and feedback from our eyes and muscles that allows us to maintain a controlled grip. Robots, however, are adept at handling rigid objects and still struggle with handling flexible objects. Because the intrinsic material properties of non-rigid objects lead to dynamic distortion and inaccurate manipulation or grasping, building machines with the functionality to facilitate autonomous installation of the consumable kit to the instrument is extremely challenging.

To achieve this difficult task, the present disclosure provides the apparatus 200 with a dock, generally designated 300, for securing the instrument 210 and a cartridge, generally designated 600, for holding the consumable kit 220. The cartridge 600 is movable, for instance, by a robot (e.g., a robotic end of arm tool), and can be selectively coupled to the dock 300. The dock and the cartridge collectively include various innovative features to facilitate automated coupling of the cartridge with the dock and ensure proper installation of the consumable kit on the instrument. For instance, in some embodiments, the dock and the cartridge collectively include one or more mechanisms to (i) establish the front surface of the instrument as a datum plane for coupling the cartridge and the dock, (ii) establish a single degree of freedom motion for moving the cartridge relative to the dock, (iii) lock the cartridge with the dock in the single degree of freedom motion, (iv) seat a pump tube around a pump head, (v) set a centrifuge carrier of the instrument in a desired position, (vi) help insert the input/output tubes of the consumable kit into corresponding tracks on the instrument, (vii) unlock a centrifuge carrier of the instrument and remove a centrifuge capsule from the centrifuge carrier of the instrument, (viii) facilitate moving of the cartridge by a robot (e.g., a robotic end of arm tool), (ix) enable automated connection of the consumable kit with external components, or any combination thereof. Thus, by utilizing a cartridge and a dock of the present disclosure, the apparatus 200 can facilitate automated loading and/or unloading a consumable kit to an instrument while retaining the benefits of conventional systems and processes (e.g., without any modification to any core elements of the conventional systems and processes). This enables the transformation of cellular engineering target manufacturing from labor-based and low-throughput processes to fully industrialized, high-throughput processes with high scale, efficiency and repeatability.

For instance, referring to FIGS. 2A and FIGS. 3A-3C, in some embodiments, the dock 300 includes a mechanism to establish a datum plane, secure the instrument and/or achieve other functionalities. For instance, in some embodiments, the dock 300 includes a frame, such as a frame 310, for surrounding (e.g., bordering) at least a portion of a perimeter of the instrument at or adjacent to the front surface 215 of the instrument. The frame can be a closed frame surrounding the entire perimeter of the instrument at or adjacent to the front surface of the instrument, or an open frame surrounding only a portion of the perimeter of the instrument at or adjacent to the front surface of the instrument. As a non-limiting example, the frame 310 is illustrated to be a closed frame. The frame includes a front surface 311 that is planar or substantially planer.

In some embodiments, the dock 300 includes a plurality of face reference members, such as face reference members 320, configured to align the front surface of the instrument with the front surface of the frame, thereby establishing the front surface of the instrument as a datum plane for coupling the cartridge 600 with the dock 300 and hence installing the consumable kit 220 on the instrument 210. The dock 300 can include any suitable number (e.g., 2, 3, 4, 5, or more than 5) of face reference members, which can be disposed at any suitable positions on the frame. In some embodiments, the dock 300 includes at least one face reference member (e.g., 320-1) disposed at a left side of the frame, at least one face reference member (e.g., 320-2) disposed at a right side of the frame, and at least one face reference member (e.g., 320-3) disposed at a bottom side of the frame. In some embodiments, the dock 300 consists of face reference members acting as three point contacts to the front surface of the instrument, thereby establishing the front surface of the instrument as the datum.

In some embodiments, the plurality of face reference members is disposed at the front surface of the frame. For instance, in some embodiments, a face reference member includes a pin, such as a pin 321, elongated in a direction parallel or substantially parallel to the front surface of the frame. A portion of the pin (e.g., a suspension) is extended beyond an inner edge (e.g., edge 312) of the frame to abut the front surface of the instrument, thereby aligning the front surface of the frame with the front surface of the instrument. The pin can be fastened, for instance, by a fastener, to the frame or integrally formed with the frame.

In some embodiments, the dock 300 includes a base, such as a base 332, configured to hold the instrument 210. The frame is connected to the base. In embodiments where the front surface of the instrument 210 is slanted, the dock 300 includes one or more upright members (e.g., upright with respect to the base), such as upright members 334. The one or more upright members are fixed on (e.g., connected to or formed with) the base to support the frame at an angle with respect to the base so that the front surface of the frame is aligned or substantially aligned with the front surface of the instrument. In some embodiments, the dock 300 includes one or more stoppers, such as stoppers 336, fixed on the base, to abut a wall (e.g., a side wall or a back wall) of the instrument. Abutting the wall(s) of the instrument by the stopper(s) helps to secure the instrument with the dock and/or align the front surface of the frame with the front surface of the instrument. In some embodiments, each of the one or more stoppers is adjustable (e.g., with an extension that allows one to adjust its length to abut a wall of the instrument).

Referring to FIGS. 3A-3C and 6A-6D, in some embodiments, the dock 300 and the cartridge 600 include a mechanism to establish a single degree of freedom motion for moving the cartridge relative to the dock. For instance, in some embodiments, the cartridge 600 includes a plurality of first docking members, such as first docking members 620, coupled to or formed with a mounting member, such as a mounting member 610, and the dock 300 includes a plurality of second docking members, such as second docking members 340, coupled to or formed with the frame 310. The cartridge can include any suitable number (e.g., 2, 3, 4, 5, or more) of first docking members, which can be but do not have to be identical or symmetric to each other. Similarly to the cartridge, the dock can include any suitable number (e.g., 2, 3, 4, 5, or more) of second docking members, which can be but do not have to be identical or symmetric to each other. As a non-limiting examples, two first docking members 620 and two second docking members 340 are shown.

Each of the plurality of first docking members and a corresponding second docking member in the plurality of second docking members are configured to removably couple with each other. For instance, in the illustrated embodiment, the first docking member 620-1 and the second docking member 340-1 are configured to removably couple with each other, and the first docking member 620-2 and the second docking member 340-2 are configured to removably couple with each other.

In some embodiments, one of the first and second docking members includes a pin and the other of the first and second docking members includes an opening (e.g., a bushing) to receive the pin. For instance, as a non-limiting example, it is shown that the second docking member 340 includes a pin 341 and the first docking member 620 includes an opening 621 to receive the pin. The pin is elongated in a direction perpendicular or substantially perpendicular to the front surface of the instrument (or the front surface of the frame). As such, coupling of the plurality of first docking members with the plurality of second docking members will restrict the mounting member of the cartridge from moving relative to the frame in a plane parallel or substantially parallel to the front surface of the instrument, but allow the mounting member of the cartridge to move relative to the frame in a first direction perpendicular or substantially perpendicular to the front surface of the instrument. In other words, coupling of the plurality of first docking members with the plurality of second docking members establishes a single degree of freedom motion for moving the cartridge with respect to the dock. This also grossly positions the consumable kit with the instrument, and allows using one degree of freedom to precisely lock (e.g., clamp) the cartridge with the dock to install the consumable kit on the instrument.

Still referring to FIGS. 3A-3C and 6A-6D, in some embodiments, the dock 300 and the cartridge 600 include a mechanism to use the single degree of freedom to lock (e.g., clamp) the cartridge with the dock. For instance, in some embodiments, the cartridge 600 includes a plurality of first locking members, such as first locking members 630, coupled to or formed with the mounting member, and the dock 300 includes a plurality of second locking members, such as second locking members 350, coupled to the frame. The cartridge can include any suitable number (e.g., 2, 3, 4, 5, or more) of first locking members, which can be but do not have to be identical or symmetric to each other. Similarly to the cartridge, the dock can include any suitable number (e.g., 2, 3, 4, 5, or more) of second locking members, which can be but do not have to be identical or symmetric to each other. As a non-limiting examples, four first locking members 630 and four second locking members 350 are shown.

Each respective second locking member in the plurality of second locking members is operably movable relative to the frame between a corresponding first position and a corresponding second position to selectively engage with or disengage from a corresponding first locking member in the plurality of first locking members. For instance, in the illustrated embodiment, the second locking member 350-1 is operably movable relative to the frame in the direction indicated by the arrow in FIG. 3C to selectively engage with or disengage from the first locking member 630-1. Similarly, the second locking member 350-2 is operably movable relative to the frame to selectively engage with or disengage from the first locking member 630-2. The second locking member 350-3 is operably movable relative to the frame to selectively engage with or disengage from the first locking member 630-3. The second locking member 350-4 is operably movable relative to the frame to selectively engage with or disengage from the first locking member 630-4. In the illustrated embodiments, the four second locking members are operably movable relative to the frame in the same direction. However, the present disclosure is not limited thereto. The plurality of second locking members can be configured to move independently and/or in different directions.

In some embodiments, the first locking member includes a ramp, such as a ramp 631, having a sloping surface with respect to the front surface of the instrument. In some embodiments, the first locking member is made of a material, such as a sheet metal, a plastic, or the like. The second locking member includes a ramp follower, such as a ramp follower 351, operably movable on the sloping surface of the ramp. In some embodiments, the ramp follower is a ball bearing capable of rolling along the sloping surface of the ramp. Moving the ramp follower on the sloping surface of the ramp in one direction will push the mounting member of the cartridge toward the front surface of the instrument, and eventually lock the mounting member of the cartridge with the frame of the dock. Moving the ramp follower on the sloping surface of the ramp in an opposite direction will push the mounting member of the cartridge away from the front surface of the instrument and eventually allow removal of the cartridge from the dock. In other words, the mounting member of the cartridge can be locked or unlocked with the frame of the dock by a single degree of freedom motion of the mounting member (e.g., moving in a direction perpendicular or substantially perpendicular to the front surface of the instrument).

Advantageously, moving the ramp follower on the sloping surface of the ramp to engage the first and second locking members (along with some other features disclosed herein such as docking members, tube clips, etc.) allows for establishing proper alignment of the consumable kit with the instrument and facilitating correct installment of the consumable kit on the instrument. In some embodiments, engagement of the first and second locking members installs some or all different components of the consumable kit to the instrument simultaneously. For instance, in some embodiments, engagement of the first and second locking members inserts the plurality of input/output tubes of the consumable kit into their corresponding tubing tracks on the instrument.

Referring to 3A-3C and 4A-4C, in some embodiments, the plurality of second locking members are components of more or more locking units, such as the locking units 400. As a non-limiting example, two locking units are illustrated with one disposed at the left side of the frame and one disposed at the right side of the frame. Each locking unit includes two second locking members. However, the present disclosure is not limited thereto. The dock can include a single locking unit or more than two locking unit. Also, a locking unit can include a single second locking member or include more than two second locking members.

In some embodiments, the locking unit 400 includes a rail, such as a rail 410. The rail is fixed on or formed with the frame, and elongated in the direction indicated by the arrow in FIG. 3C. In some embodiments, the locking unit 400 includes a slide, such as a slide 420. The slide is coupled to the rail, for instance, by one or more bearings 430, and is operably movable along the rail. One or more second locking members 350 (e.g., 2 in the illustrated embodiments) are connected to or formed with the slide. In some embodiments, the slide is coupled to a cam assembly, such as a cam assembly 450, for instance, through a protrusion 440 disposed at an end portion of the slide. In some embodiments, the cam assembly is operably driven by a cam drive assembly (e.g., a motor), such as a cam drive assembly 460, and converts a rotary motion to a linear motion of the slide. Advantageously, this allows for precision clamping of the cartridge to the dock, establishing proper alignment of the consumable kit with the instrument and correct installment of the consumable kit on the instrument.

Referring to FIGS. 3A and 5A-5J, in some embodiments, the dock 300 includes a mechanism to seat a tube around a head of a pump of the instrument, e.g., seating the peristaltic tubing loop (at least a portion of it) around the fixed location pump head of the instrument. For instance, in some embodiments, the dock 300 includes a pump tube loading assembly, such as a pump tube loading assembly 500, connected to the frame and configured for placing at least a portion of a pump tube (e.g., the pump tube 221) of the consumable kit into a peristaltic pump head (e.g., the pump head 211) of the instrument. The pump tube loading assembly includes a loading member, such as loading member 510, and a driving unit, such as a driving unit 520, configured to rotate the loading member. In some embodiments, the driving unit includes a shaft assembly, such as a shaft assembly 521, and a motor, such as a motor 522, to drive the shaft assembly. In some embodiments, the shaft assembly is disposed at a bearing block, such as a bearing block 523, and covered by a cover, such as a cover 524. In some embodiments, the shaft assembly includes a drive shaft, one or more idler, and an output shaft coupled to each other by a timing belt, for instance, through pulleys, bearings, and/or other components. The drive shaft is coupled to the motor and the output shaft is coupled to the loading member, thereby facilitating rotation of the loading member in a motorized manner.

The loading member 510 is configured in accordance with the pump head of the instrument and has a unique shape to facilitate seating at least a portion of the pump tube around the pump head of the instrument. For instance, in some embodiments, the loading member includes a platform, such as a platform 511, and a finger, such as a finger 512, that is disposed at the platform and extends toward the instrument beyond the platform. The loading member is coupled to the driving unit (e.g., the output shaft), for instance, through a hole 513 formed at the platform. As such, the loading member can be rotated around an axis 214 by the driving unit. In some embodiments, when the cartridge is loaded to the dock, the axis 214 is aligned with an axis of the pump head (e.g., the peristaltic pump head) of the instrument.

Typically, the platform has a sector-shape or a substantial sector-shape with a circumferential edge, such as a circumferential edge 515, and the finger is disposed at or adjacent to this circumferential edge of the platform and extended toward the instrument beyond the platform. In some embodiments, the finger is tapered toward the instrument. As the loading member rotates (e.g., by the driving unit), the finger presses at least the portion of the pump tube of the consumable kit into the pump head and get it seated on rollers of the pump head of the instrument.

In some embodiments, the circumferential edge is curved. In some embodiments, at least a portion of the circumferential edge is circular or substantially circular with respect to the axis 514. In some embodiments, the platform has a lower surface (e.g., the surface facing the instrument), such as a lower surface 516, and an upper surface (e.g., the surface facing away from the instrument), such as an upper surface 517. The lower surface is planar or substantially planar, and parallel or substantially parallel to the front surface of the instrument. The lower surface serves as a retaining surface to confine at least the portion of the pump tube of the consumable kit and/or to help preventing prevent at least the portion of the pump tube of the consumable kit from popping out of the pump head. In some embodiments, the upper surface includes one or more steps (e.g., the upper surface includes two or more levels) to provide a space for other element(s), to reduce the size of the platform, and/or to enhance the strength of the platform. In some embodiments, the loading member includes additional or optional elements, such as a magnet 518 disposed at the platform to assist in locking the loading member when desired.

The dock can include additional, optional, or alternative components. For instance, referring to FIG. 3A, in some embodiments, the dock includes a power and/or control unit, such as an electrical distribution unit 338. The power and/or control unit is in electrical communication (wire or wireless) with one or more motors (e.g., motor 460, motor 522) to power and/or control the motion of the one or more motors.

Figure 6A:
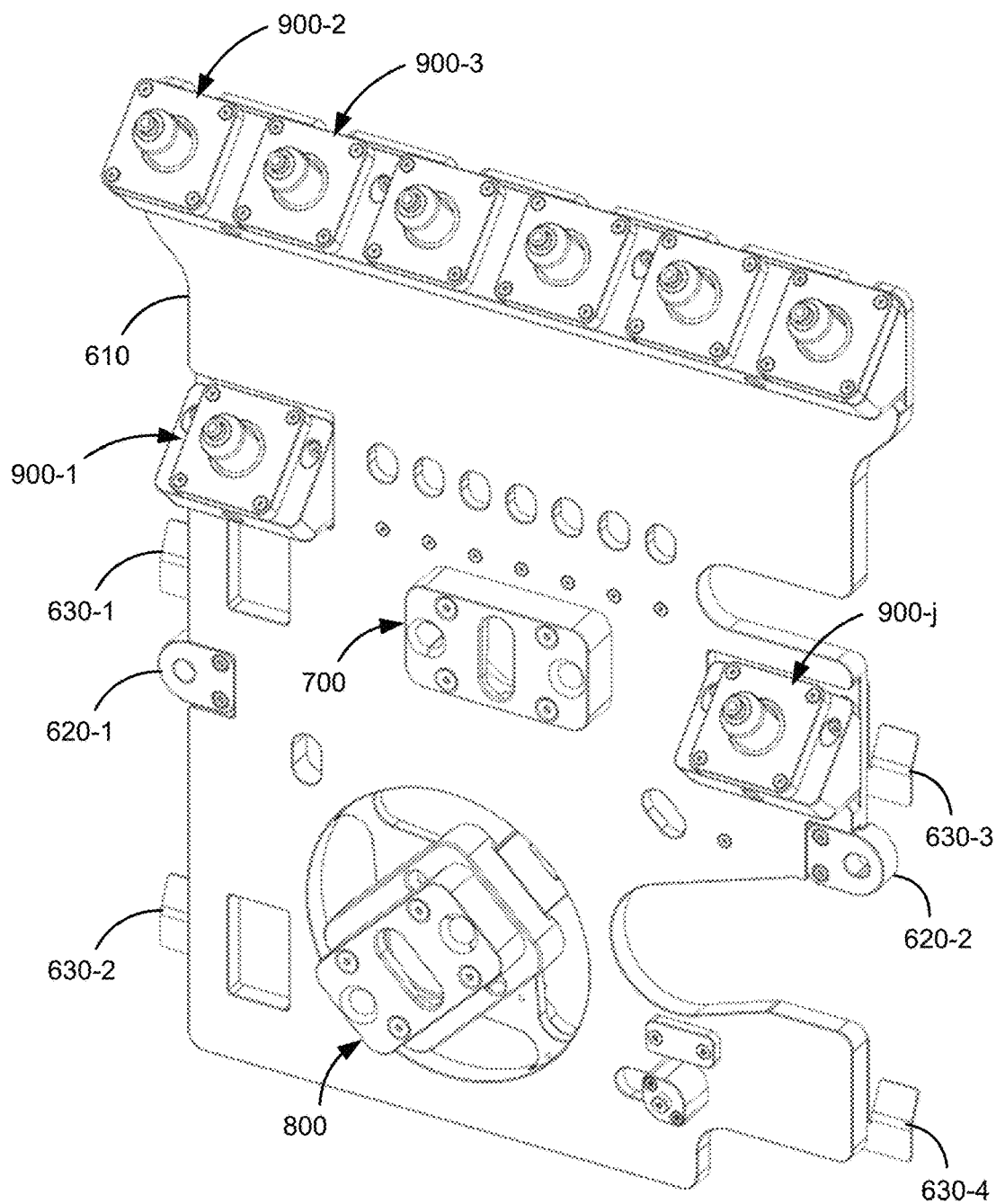
FIG. 6A is a front perspective view illustrating an exemplary cartridge in accordance with some exemplary embodiments of the present disclosure.
Figure 6B:
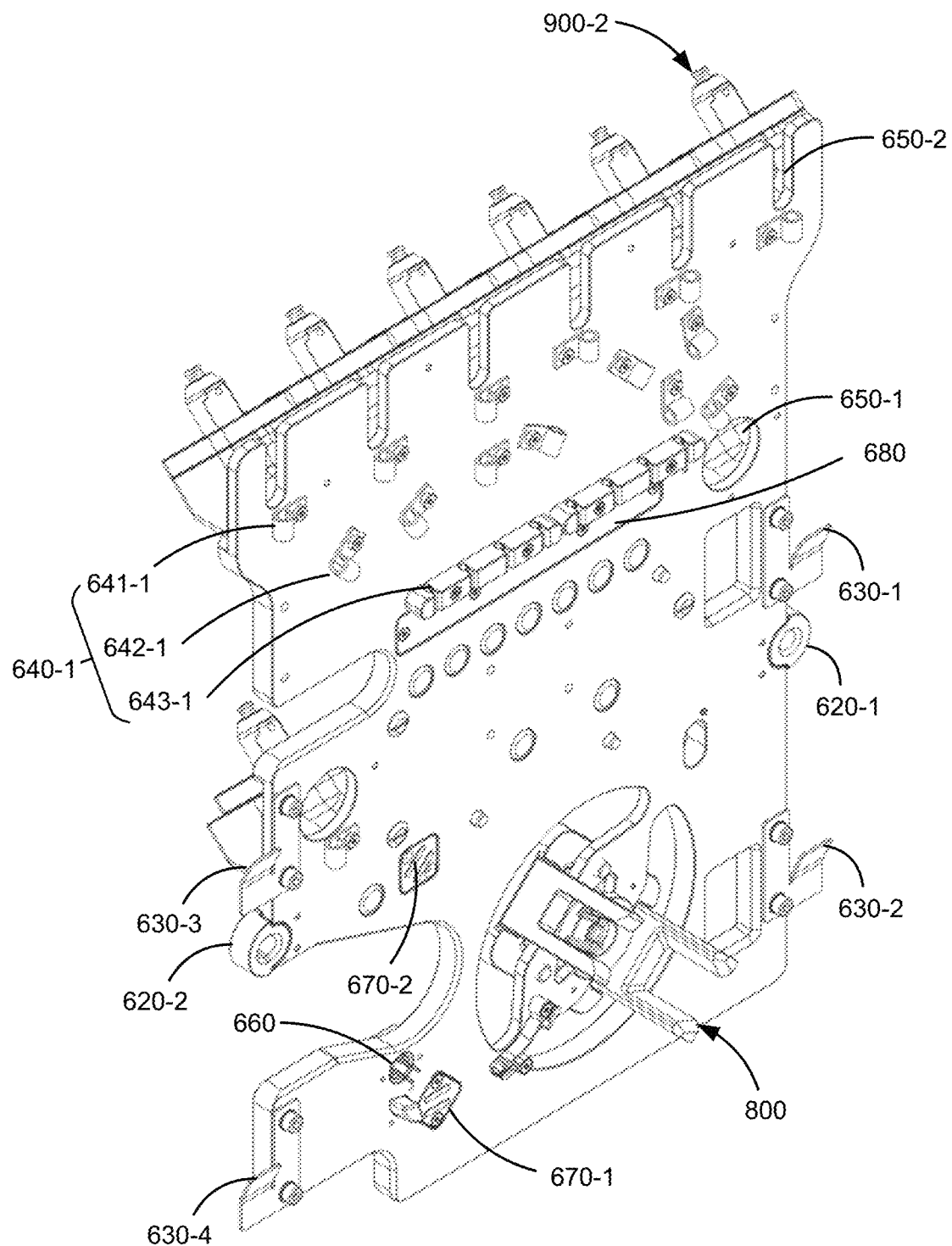
FIG. 6B is a rear perspective view illustrating the exemplary cartridge of FIG. 6A.
Figure 6C:
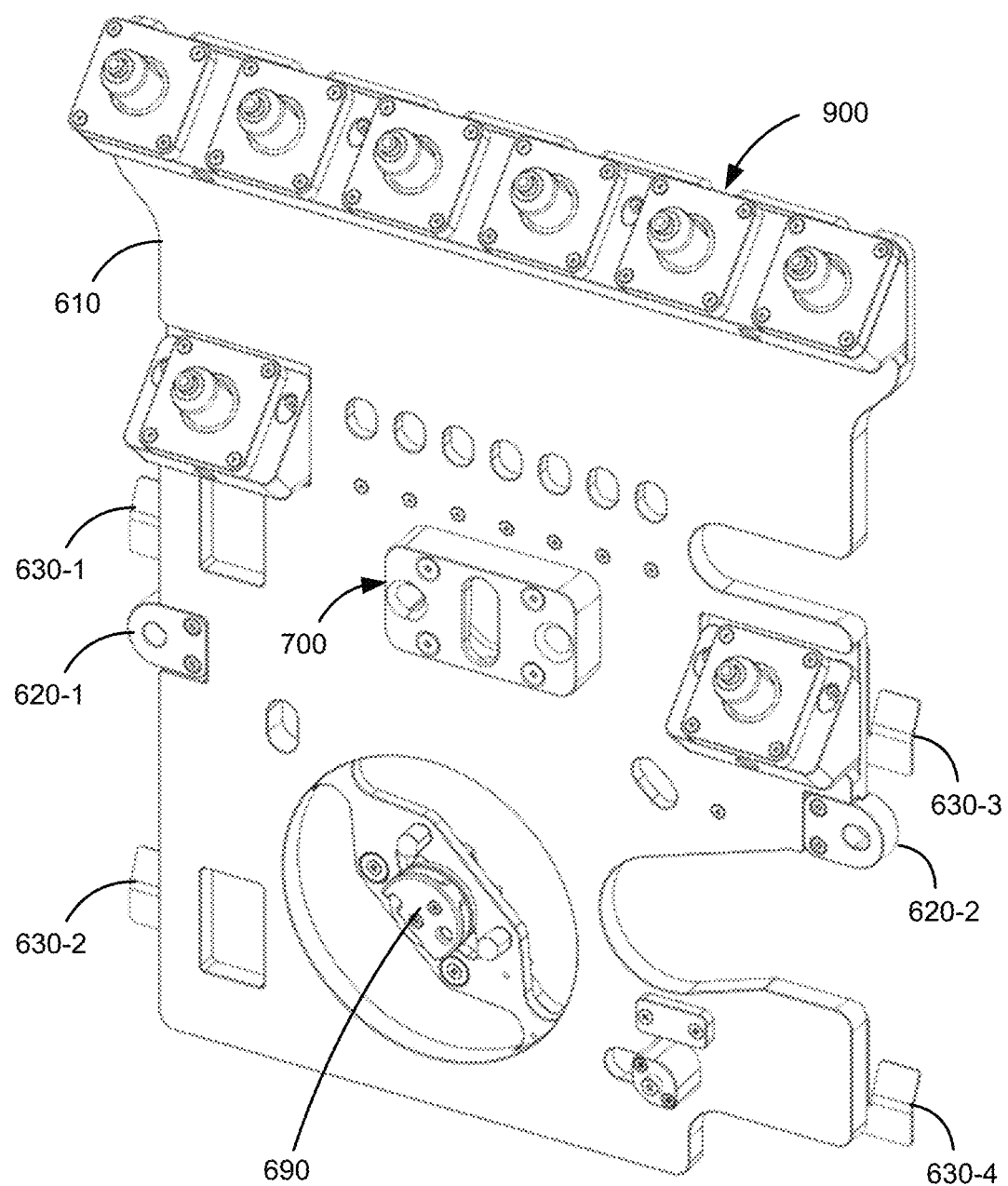
FIG. 6C is a front perspective view illustrating the exemplary cartridge of FIG. 6A where some components are removed for clarity of illustration.
Figure 6D:
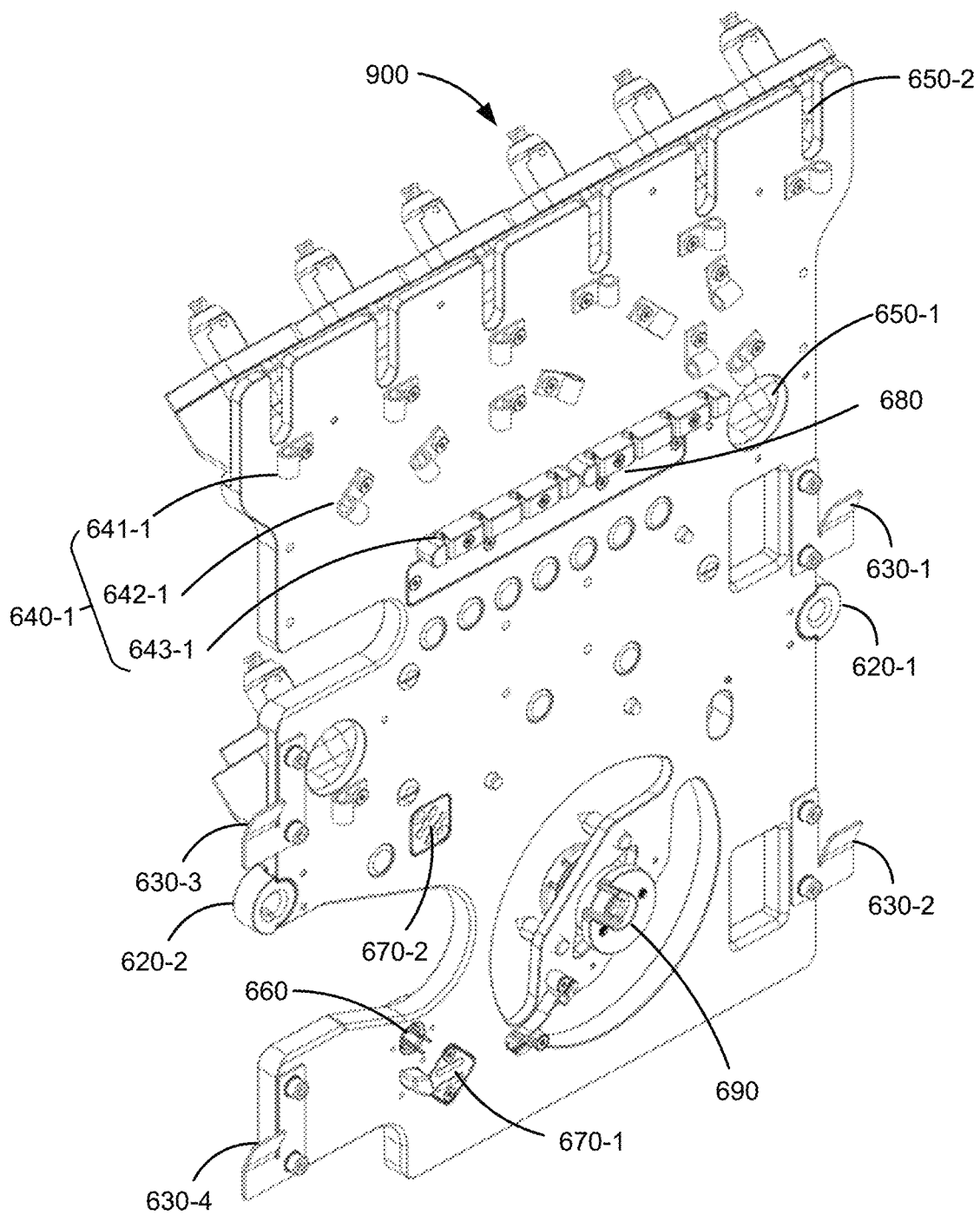
FIG. 6D is a rear perspective view illustrating the exemplary cartridge of FIG. 6C.

Referring to FIGS. 6B and 6D, in some embodiments, the cartridge 240 includes a mechanism to help insert the input/output tubes of the consumable kit into corresponding tracks on the instrument. For instance, in some embodiments, the cartridge includes a plurality of tube retaining sets, such as tube retaining sets 640. Each respective tube retaining set in the plurality of tube retaining sets includes one or more corresponding tube retaining members disposed at the back side of the mounting member and configured to retain a corresponding tube in a plurality of input and output tubes of the consumable kit. In some embodiments, a tube retaining member is a fastener, a clip, a slot, or the like. For instance, in the illustrated embodiment, the tube retaining set 640-1 includes a retaining member 641-1, a retaining member 642-1 and a retaining member 643-1, where the retaining members 641-1, 642-1 are in a form of a P-clip and the retaining member 643-1 is in a form of a slot. However, the present disclosure is not limited thereto. A tube retaining set can have one, two, three, four, five or more than five retaining members, and a retaining member can have a different shape and/or size. Moreover, a tube retaining set can have the same number of retaining members as another tube retaining set or a different number of retaining members from another tube retaining set.

In some embodiments, the one or more corresponding tube retaining members of each respective tube retaining set are disposed respectively at one or more corresponding locations on the back side of the mounting member such that engagement of each respective second locking member in the plurality of second locking members with the corresponding first locking member in the plurality of first locking members pushes the corresponding tube in the plurality of input and output tubes of the consumable kit into a corresponding tubing track in a plurality of tubing tracks formed at the front surface of the instrument. That is, through the single degree of freedom that locks (e.g., clamps) the cartridge with the dock, the input/output tube(s) of the consumable kit are inserted into the corresponding tracks on the instrument, thereby helping to ensure the proper installation of the consumable kit to the instrument.

Figure 11A:
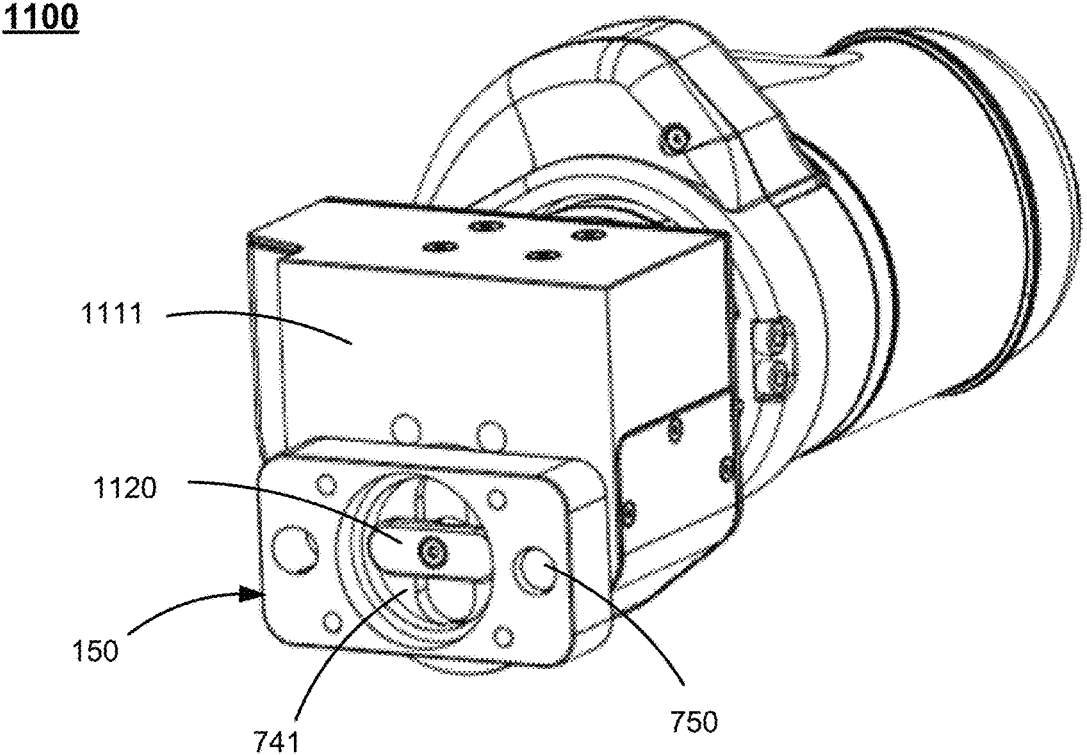
FIG. 11A is a perspective view illustrating an exemplary robotic end of arm tool in accordance with some exemplary embodiments of the present disclosure.
Figure 11B:
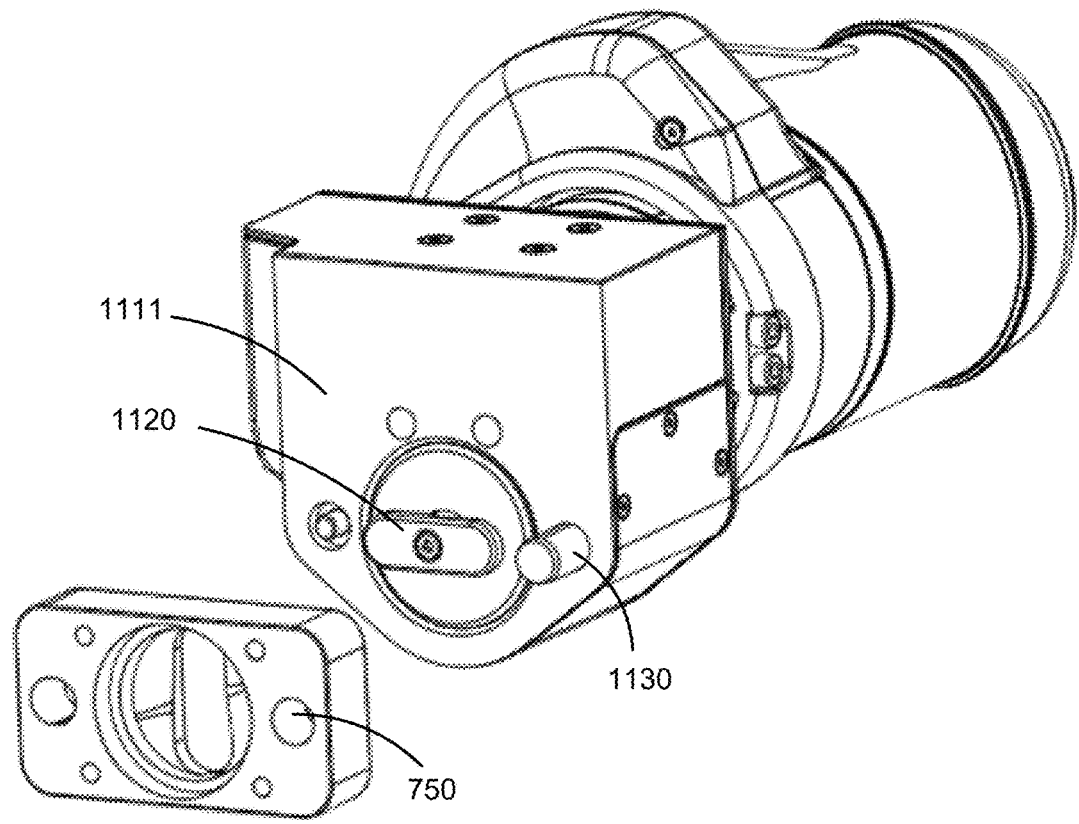
FIG. 11B is a perspective view illustrating the use of the exemplary robotic end of arm tool to grip the exemplary interface member of FIG. 7A in accordance with some exemplary embodiments of the present disclosure.

Referring to FIGS. 6A, 6C and 7A-7G, in some embodiments, the cartridge 600 includes a mechanism to facilitate moving of the cartridge by a robot (e.g., a robotic end of arm tool). For instance, in some embodiments, the cartridge includes a first interface member, such as a first interface member 700, to facilitate moving of the mounting member to or from the dock by a robotic end of arm tool (EOAT), such as an EOAT 1100 illustrated in FIGS. 11A and 11B. The EOAT 1100 includes a support having a supporting surface, such as a supporting surface 1110, that is planar or substantially planar. The EOAT 1100 also includes a cam bar, such as a cam bar 1120, that is coupled to the support and is operably ratable around an axis perpendicular or substantially perpendicular to the supporting surface of the support. The cam bar is elongated, e.g., having an elongated cross-section in a plane parallel to the supporting surface of the support with a length larger than a width.

The first interface member 700 is connected to (e.g., by one or more fasteners) or formed with the mounting member (e.g., by molding of a medical grade plastic material). The first interface member generally includes a first interface surface, a second interface surface, an elongated slot and a recess, such as a first interface surface 710, a second interface surface 720, an elongated slot 730 and a recess 740. In some embodiments, the first interface member is shaped in a form of a plate, a block or the like.

The first interface surface is accessible from a front side of the mounting member (e.g., the facing away from the mounting member) and the second interface surface is opposite to the first interface surface (e.g., facing the mounting member). The first interface surface is configured for abutting the supporting surface of the EOAT when the EOAT grips the first interface member. In some embodiments, the first interface surface is planar or substantially planar.

The elongated slot is formed through the first interface surface and configured to allow the elongated cam bar of the EOAT to insert into the first interface member. In some embodiments, the elongated slot has a width, e.g., a width "W," and a length, e.g., a length "L." The width of the elongated slot is equal to or greater than the width of the elongated cam bar of a robotic end of arm tool (EOAT) but smaller than the length of the cam bar of the EOAT. The length of the elongated slot is equal to or greater than the length of the cam bar of the EOAT. As such, the elongated slot allows insertion of the cam bar of the EOAT into the first interface member and removal of the cam bar of the EOAT from the first interface member when the cam bar of the EOAT is aligned or substantially aligned with the elongated slot.

Figure 7A:
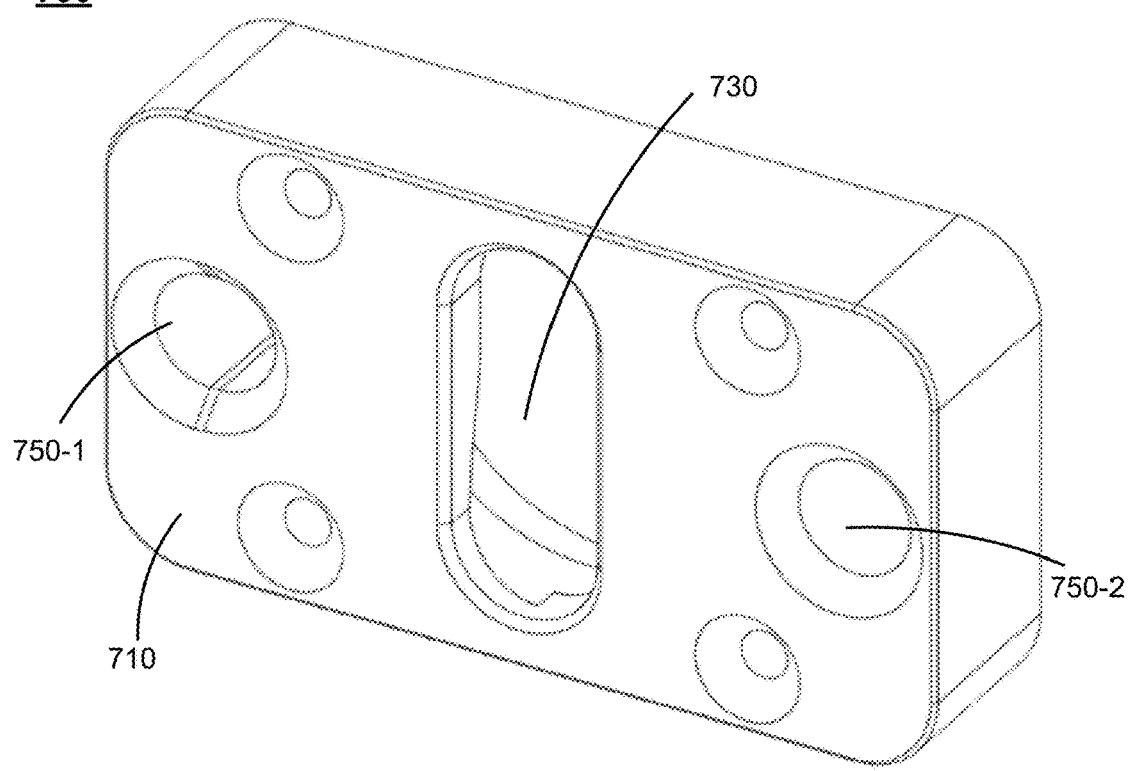
FIG. 7A is a front perspective view illustrating an exemplary interface member in accordance with some exemplary embodiments of the present disclosure.
Figure 7B:
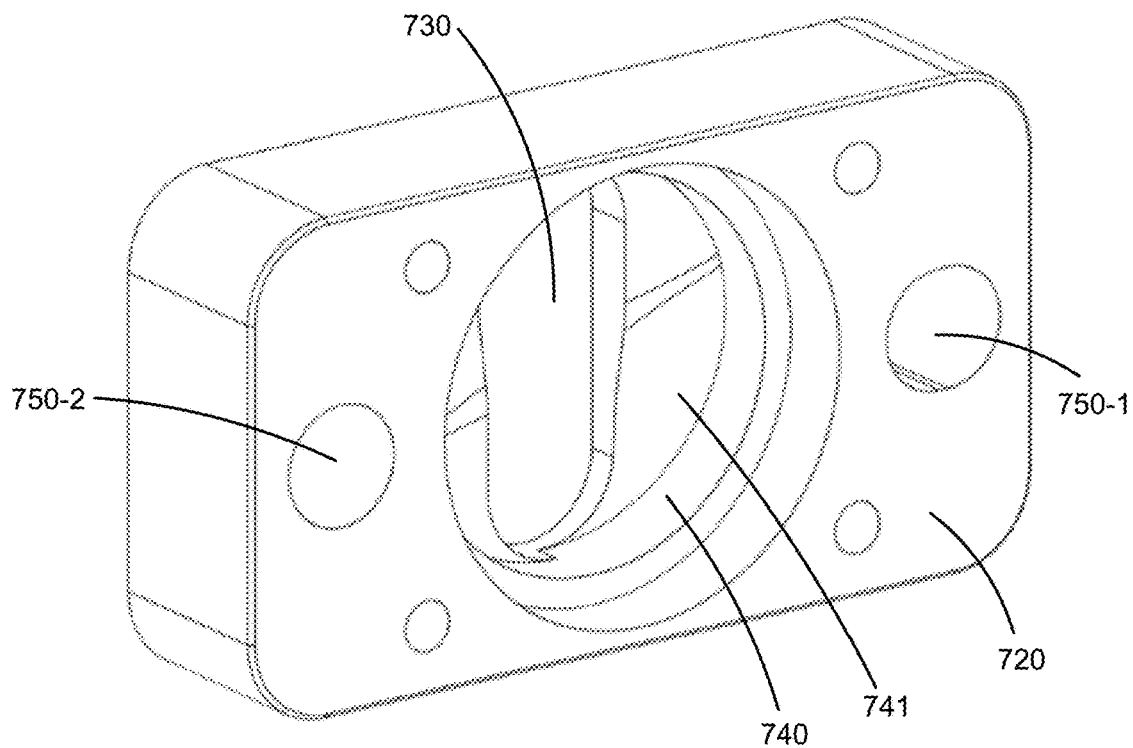
FIG. 7B is a rear perspective view illustrating the exemplary interface member of FIG. 7A.
Figure 7C:
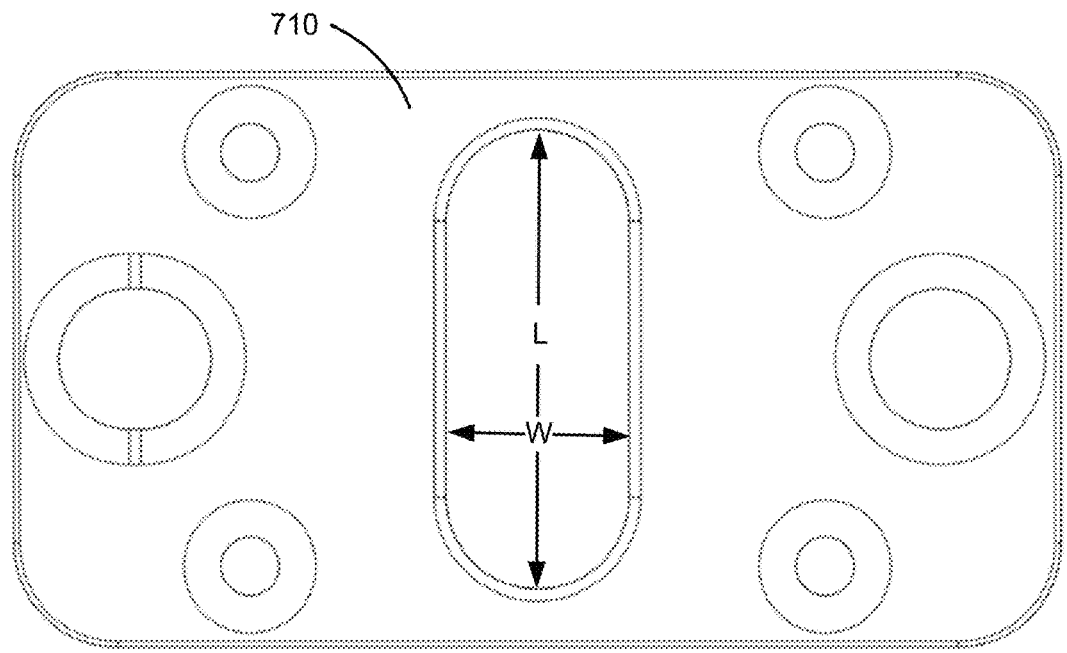
FIG. 7C is a front side view illustrating the exemplary interface member of FIG. 7A.
Figure 7D:
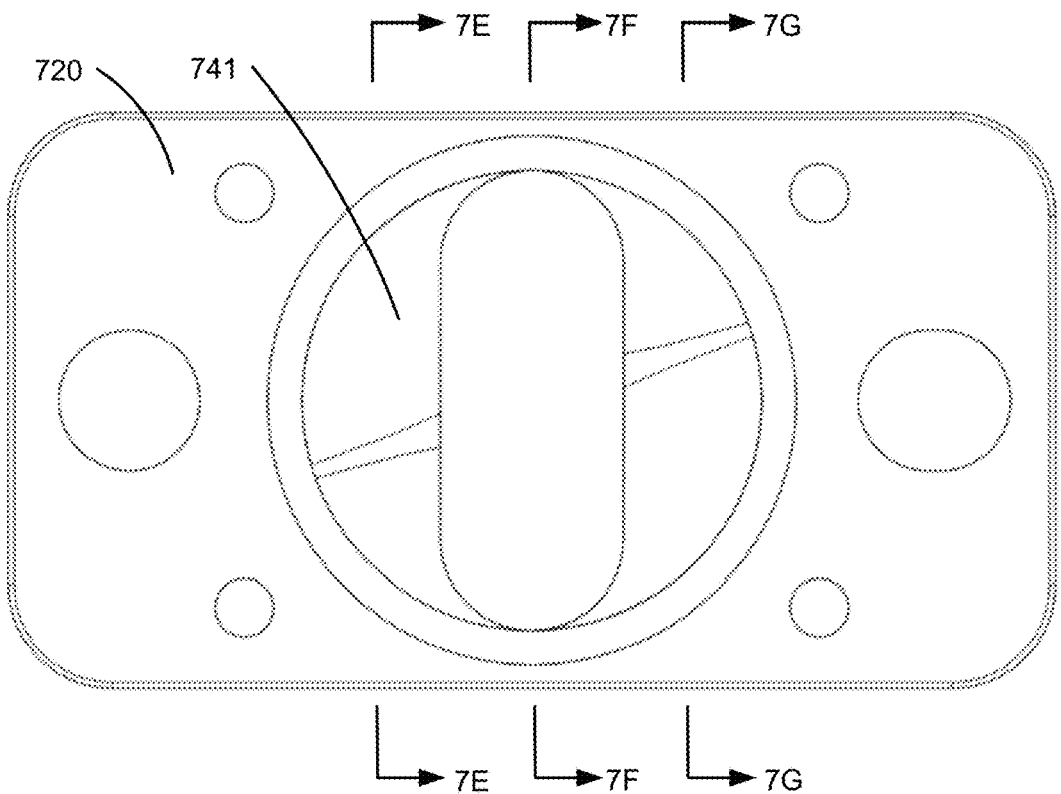
FIG. 7D is a rear side view illustrating the exemplary interface member of FIG. 7A.
Figure 7G:
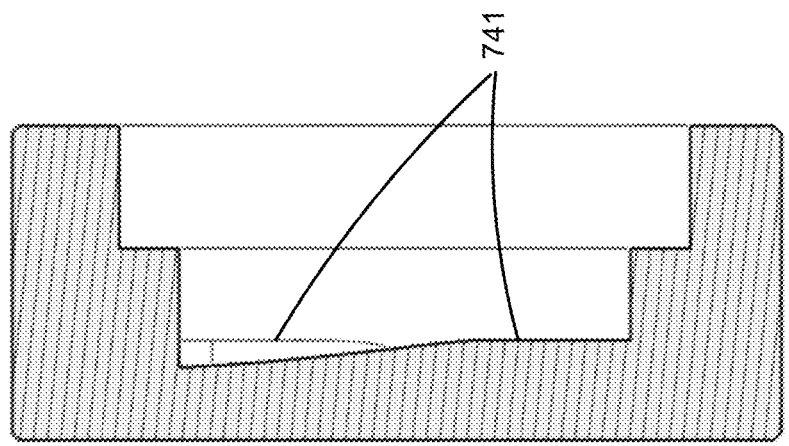
FIG. 7G is a cross-sectional view taken along line 7G-7G of FIG. 7D.
Figure 7F:
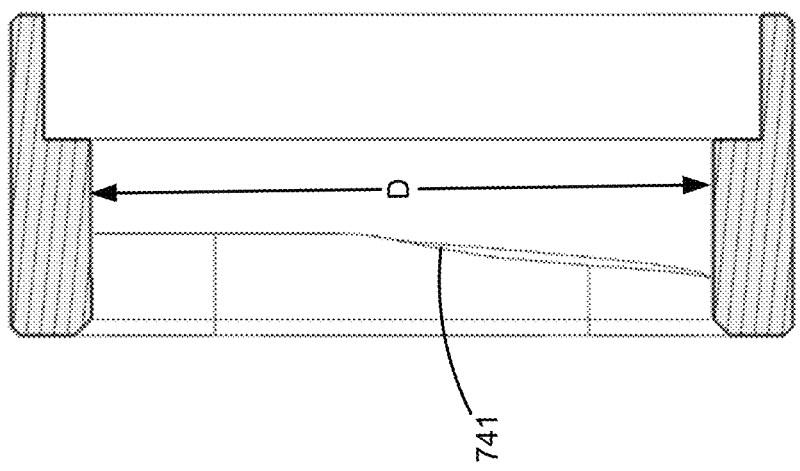
FIG. 7F is a cross-sectional view taken along line 7F-7F of FIG. 7D.
Figure 7E:
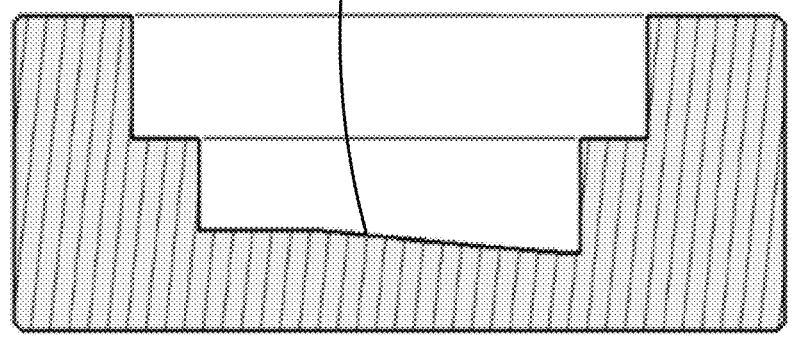
FIG. 7E is a cross-sectional view taken along line 7E-7E of FIG. 7D.
Figure 8B:
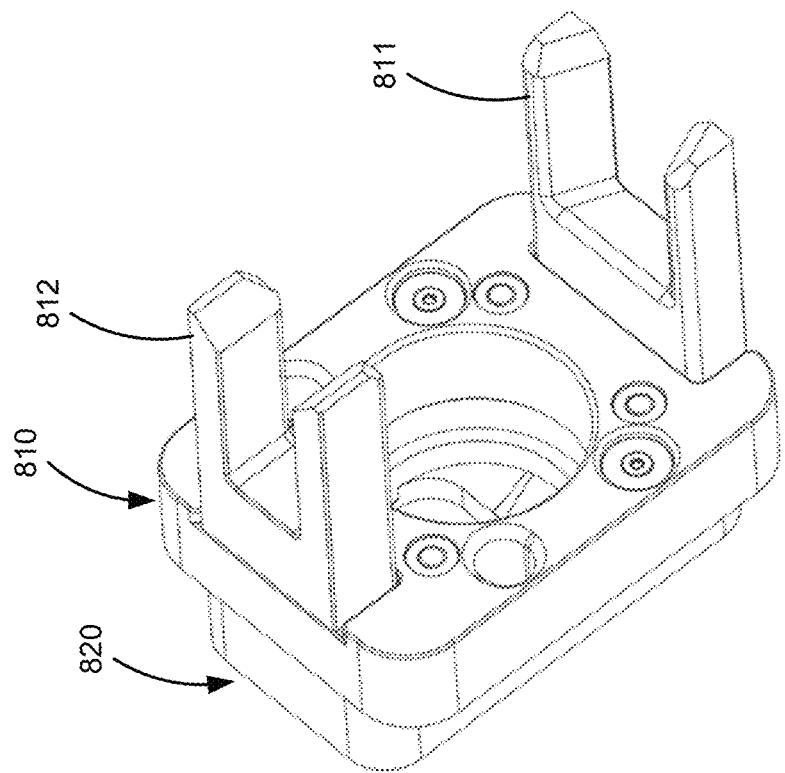
FIG. 8B is a rear perspective view illustrating the exemplary capsule removal assembly of FIG. 8A.
Figure 8A:
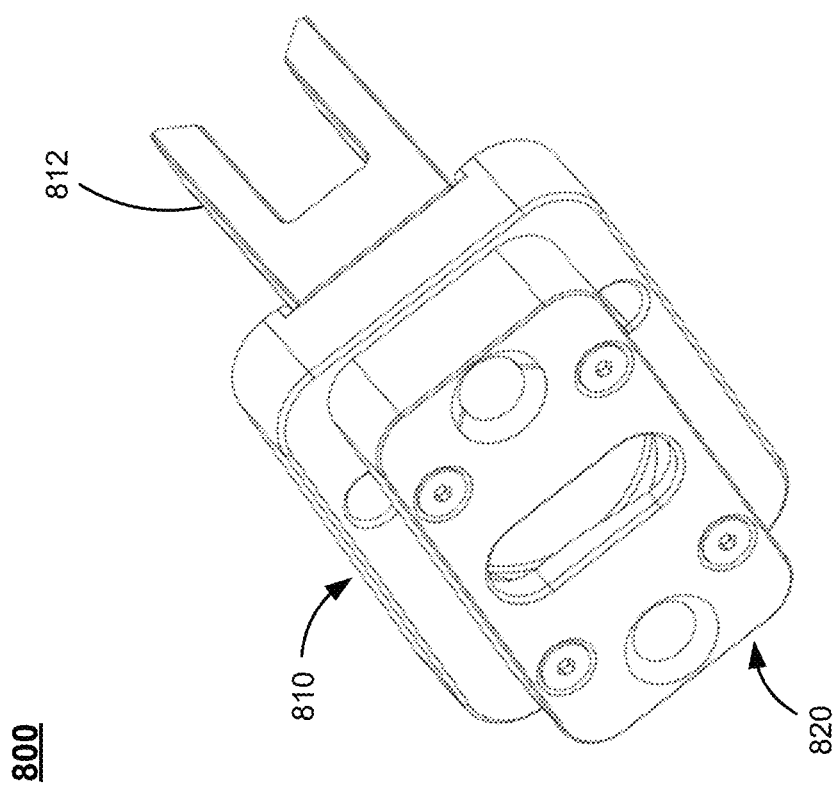
FIG. 8A is a front perspective view illustrating an exemplary capsule removal assembly in accordance with some exemplary embodiments of the present disclosure.

The recess is recessed from the second interface surface toward the first interface surface. It has a dimension, e.g., a diameter "D," that is larger than the width of the elongated slot and the length of the elongated cam bar, thereby allowing the elongated cam bar of the EOAT to rotate within the first interface member. In some embodiments, the recess is a circular blind hole formed through the second interface surface and aligned with the elongated slot. In some embodiments, the recess has a bottom surface, such as a bottom surface 741 within the first interface member. The bottom surface is characterized by a first cam profile, e.g., curved or slanted relative to the first interface surface. As a non-limiting example, FIGS. 7E-7G illustrate an exemplary profile of the bottom surface in accordance with some exemplary embodiments of the present disclosure. However, the present invention is not limited to. The bottom surface can be configured with other profiles. In some embodiments, a surface of the cam bar that faces the supporting surface of the support is characterized by a second cam profile. In some embodiments, the cam bar includes one or more chamfered edges (e.g., 45 degrees chamfered edge). In some embodiments, the first cam profile of the bottom surface of the recess of the first interface member and the second cam profile of the surface of the cam bar are complemental to each other.

When the cam bar of the EOAT rotates, the cam bar of the EOAT abuts the bottom surface of the recess of the first interface member while the first interface surface of the first interface member abuts the supporting surface of the EOAT. As such, the EOAT grips the first interface member and thus the cartridge. Accordingly, the cartridge can be moved to any desired location on demand by the EOAT through the first interface member. In some embodiments, the cam profile of the cam bar includes one or more chamfered edges (e.g., one or more 45 degree chamfered edges), thereby allowing the cam bar to rotate to a lock position and jamming against the bottom surface of the recess of the interface member as a hard stop.

In some embodiments, the first interface member 700 includes a plurality of first alignment elements, such as first alignment elements 750, connected to or formed with the first interface member. The EOAT 1110 includes a plurality of second alignment elements, such as second alignment elements 1130, connected to or formed with the support. The first and second alignment elements are configured to couple with each other. In some embodiments, one of the first and second alignment elements is a pin and the other of the first and second alignment elements is a pin hole. As a non-limiting example, it is illustrated that the first interface member includes a plurality of pin holes (e.g., 2 pin holes) and the EOAT includes a plurality of pins (e.g., 2 pins), of which each respective pin hole in the plurality of pin holes is configured to receive a corresponding pin in the plurality of pins, thereby facilitating alignment of the robotic EOAT with the interface member.

Referring to FIGS. 6A-6B and 8A-8B, in some embodiments, the cartridge 600 includes a mechanism to remove a centrifuge capsule (e.g., the centrifuge capsule 122) of a consumable kit (e.g., the consumable kit 120) from a centrifuge chamber carrier (e.g., the chamber carrier 112) of the instrument. For instance, in some embodiments, the cartridge includes a capsule removal assembly, such as a capsule removal unit 800, configured to removably couple to the mounting member. In some embodiments, the capsule removal assembly includes a capsule releasing member, such as a capsule releasing member 810, for unlocking the centrifuge capsule of the consumable kit from the centrifuge chamber carrier of the instrument. In some embodiments, the capsule releasing member includes a first jaw, such as a first jaw 811, and a second jaw, such as a second jaw 812. The first and second jaws are insertable through one or more holes formed on the mounting member. The first jaw is configured to grip the centrifuge capsule of the consumable kit, and the second jaw is configured to lift a lever in the centrifuge chamber carrier of the instrument, thereby unlocking the centrifuge capsule of the consumable kit from the centrifuge chamber carrier of the instrument.

In some embodiments, the cartridge includes a second interface member, such as a second interface member 820, connected to or formed with the capsule releasing member. the second interface member is robot-operable, thereby facilitating moving of the capsule releasing member relative to the instrument. The second interface member can be configured the same as or different from the first interface member. As a non-limiting example, the second interface member is illustrated to be identical to the first interface member.

Referring to FIGS. 6A-6D, in some embodiments, the cartridge 240 includes a mechanism to enable automated connection of the consumable kit with other components or devices (e.g., components or devices other than the instrument 110). For instance, in some embodiments, the cartridge includes a plurality of port assemblies, such as the port assemblies 900, disposed at the mounting member. The port assemblies can be configured the same as each other or different from each other. As a non-limiting example, the port assemblies are illustrated to be identical or almost identical to each other. The port assemblies can be disposed at any suitable locations, and can be aligned with each other (e.g., the port assembly 900-2 is aligned with the port assembly 900-3) or offset from each other (e.g., the port assembly 900-1 is offset from the port assembly 900-2 and/or the port assembly 900-*j*).

In various embodiments, the port assembly includes a floating non-rotating design that is compatible with a variety of fluid and non-fluid connectors and incorporates an external lead-in feature for the mating coupler. One of the key innovations is the combination of the port body shape which has a tip (e.g., a large chamfered tip) to engage with a mating coupler and corresponding size multi-directional planar float of the port body that accommodates axial misalignment but resists torsional loads typically associated with a threaded connector. The port body is designed to house fluid, gas, and electrical connectors effectively converting an array of industry standard connectors into robotic compatible connectors due to the external mating feature and position tolerance compensation via the floating design (e.g., movable) of the port body. In some embodiments, the port assembly is configured for accommodating axial misalignment during mating with a device or a component of a device.

Referring to FIGS. 9A-9G, in some embodiments, the port assembly 900 includes a port body, such as a port body 901, and a retainer, such as a retainer 902, coupled to each other. The port body is configured to hold a first device (e.g., a connector), such as a first device 903. The retainer is connected to the mounting member and configured to restrict the port body from rotating relative to the retainer but allow the port body to move translationally relative to the retainer in a plane substantially perpendicular to an axial direction of the port body. Accordingly, the retainer restricts the first device, which is held by the port body, from rotating relative to the retainer but allows the first device to move translationally relative to the retainer in the plane substantially perpendicular to the axial direction of the port body. Advantageously, this can accommodate axial misalignment when connecting the first device with a second device while constraining rotation.

Figure 9B:
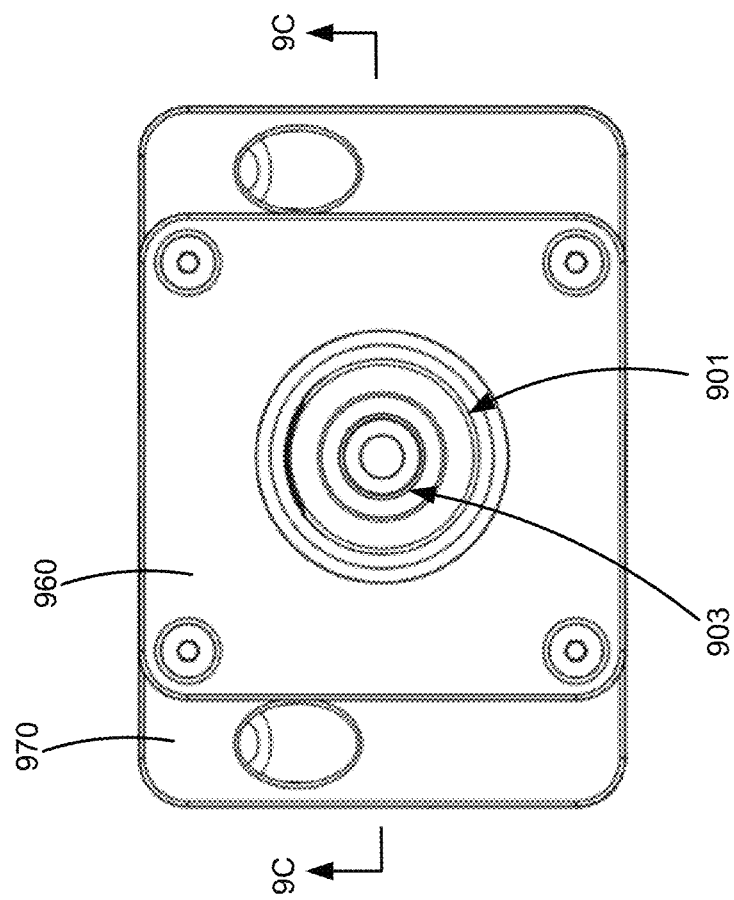
FIG. 9B is a top view illustrating the exemplary port assembly of FIG. 9A.
Figure 9A:
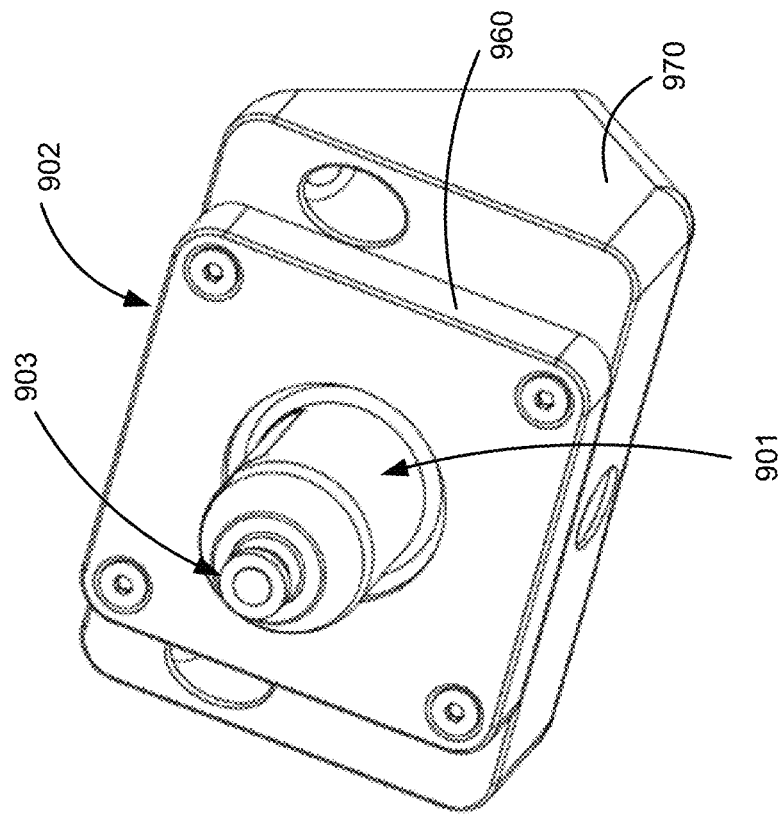
FIG. 9A is a perspective view illustrating an exemplary port assembly in accordance with some exemplary embodiments of the present disclosure.
Figure 9C:
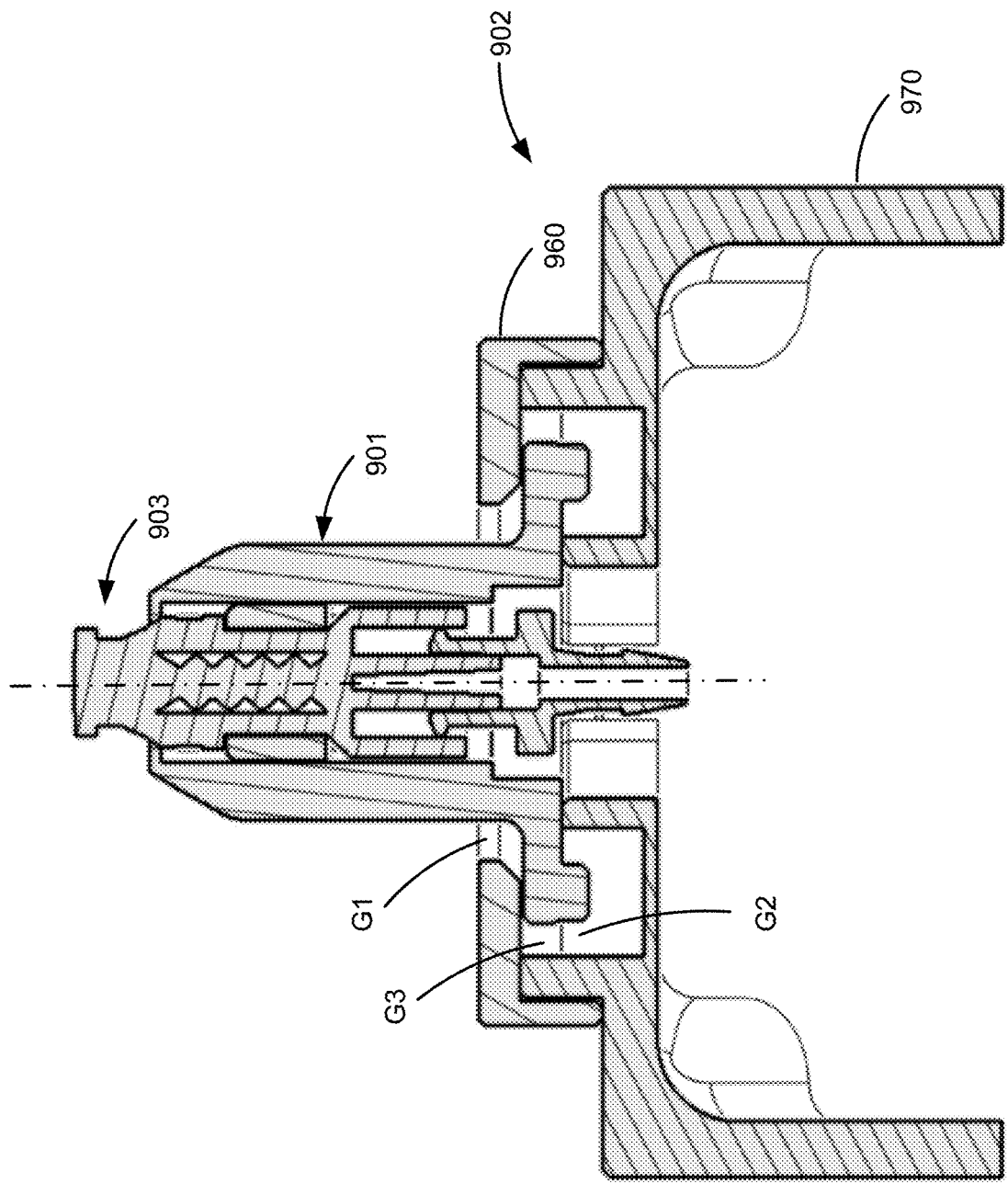
FIG. 9C is a cross-sectional view taken along line 9C-9C of FIG. 9B.
Figure 9D:
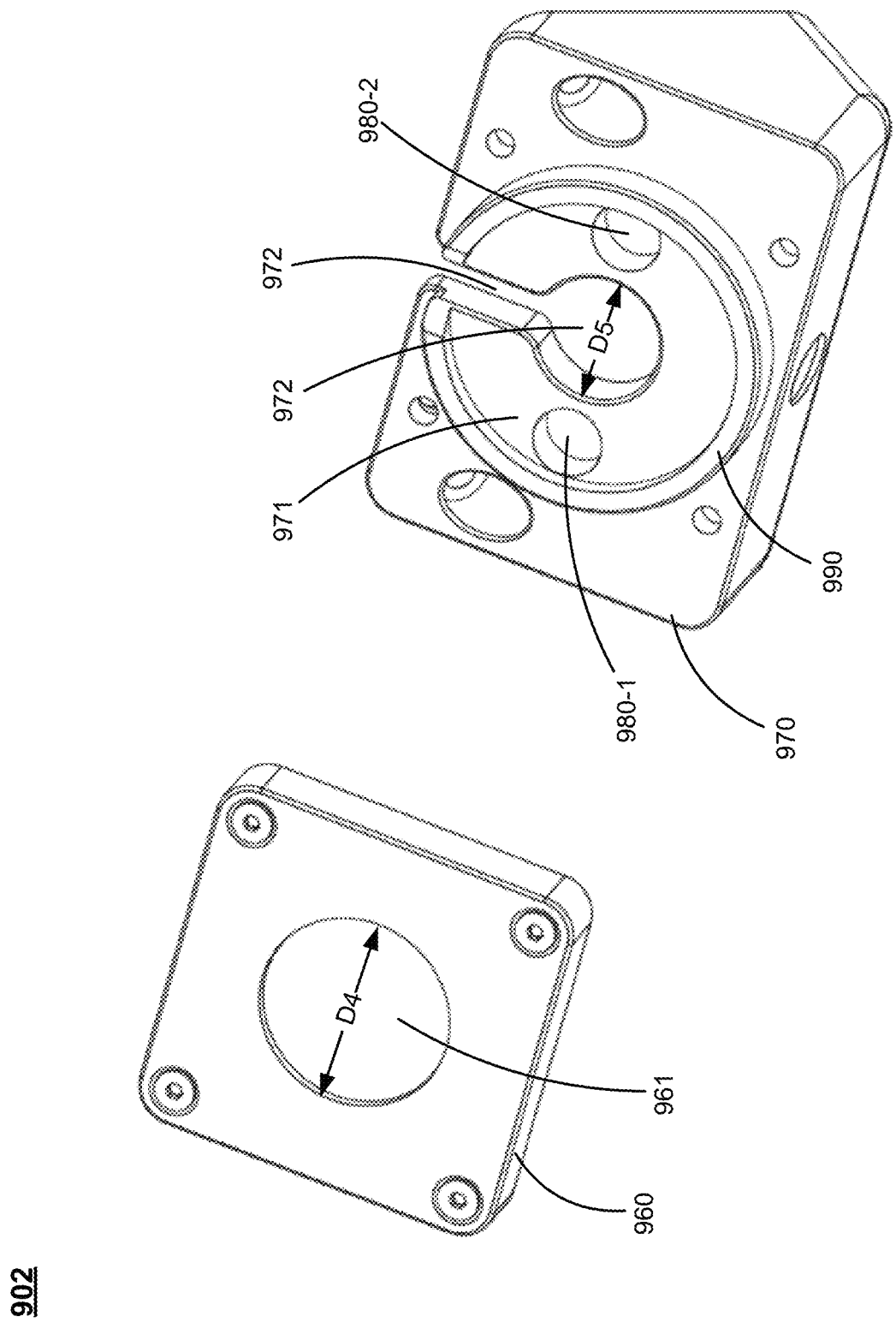
FIG. 9D is an exploded view illustrating an exemplary retainer in accordance with some exemplary embodiments of the present disclosure.
Figure 9E:
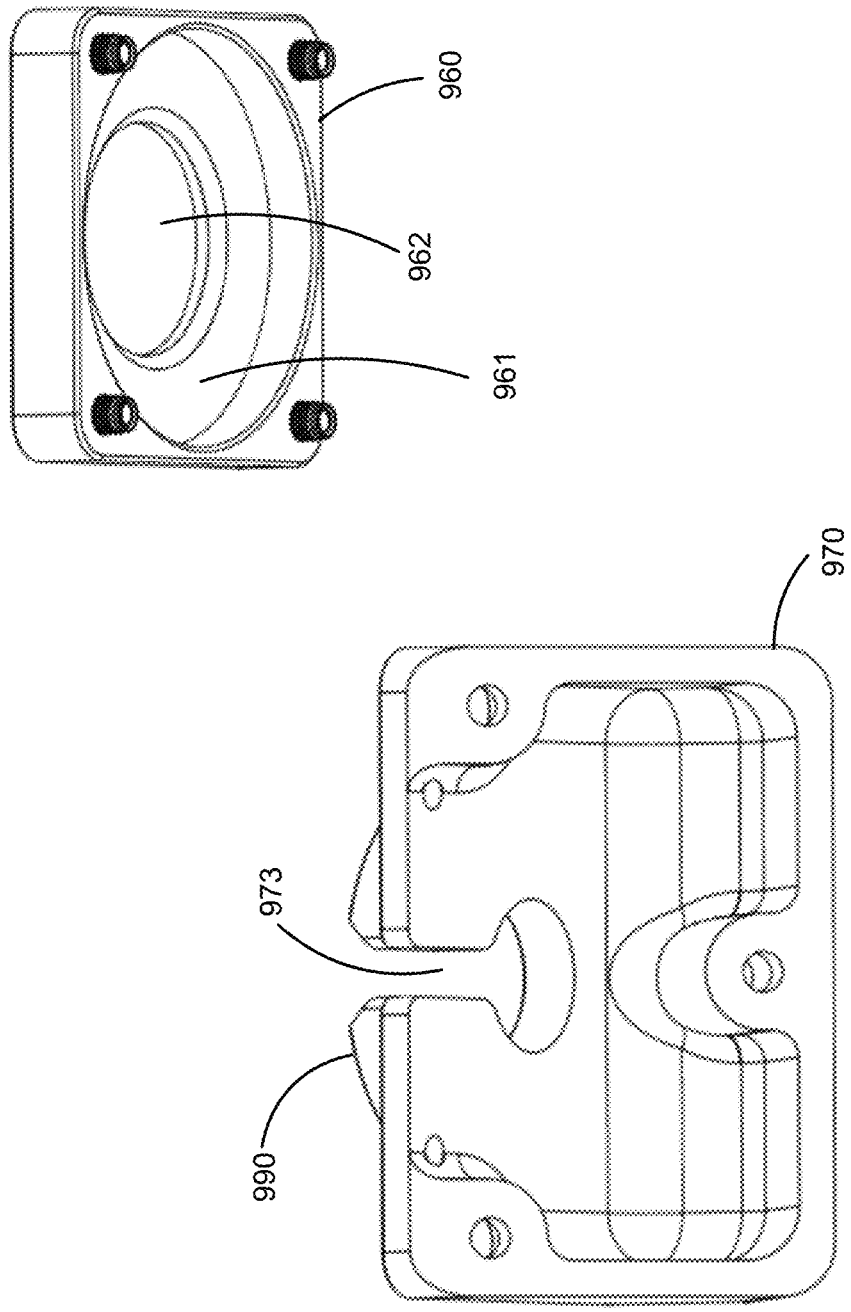
FIG. 9E is another exploded view illustrating the exemplary retainer of FIG. 9E.
Figure 9G:
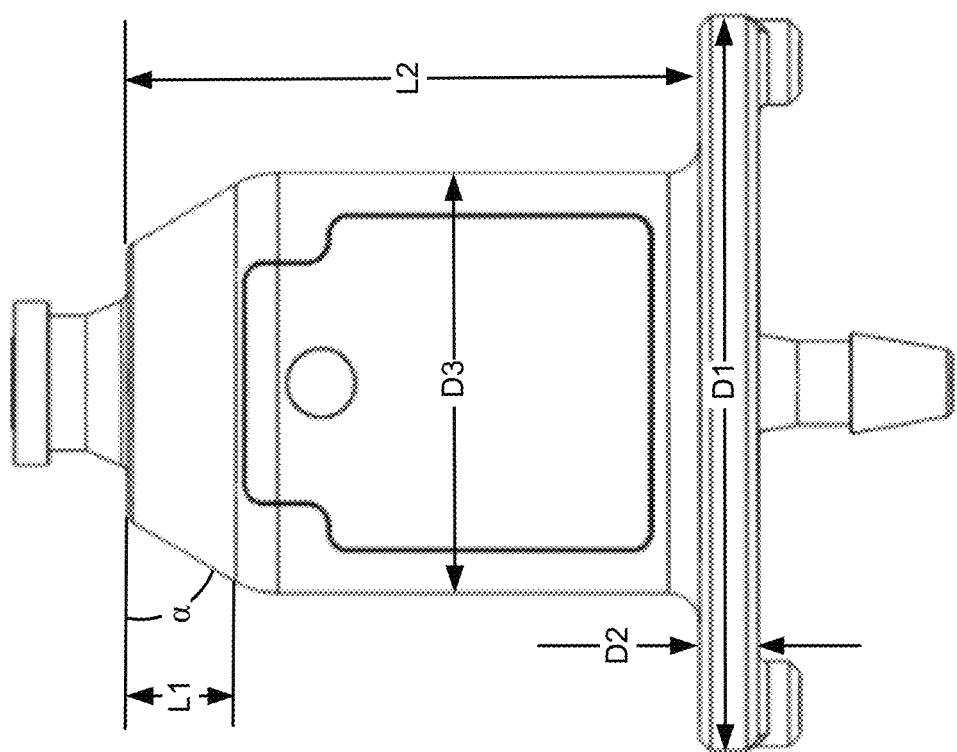
FIG. 9G is a side view illustrating the exemplary port body of FIG. 9F.
Figure 9F:
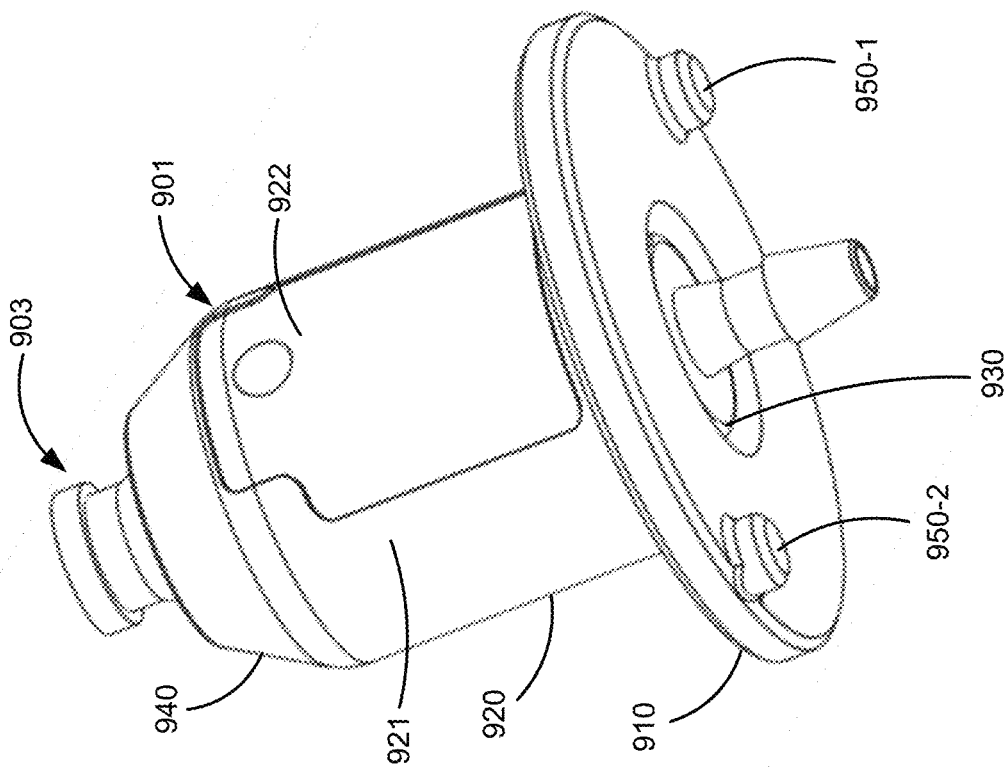
FIG. 9F is a perspective view illustrating an exemplary port body in accordance with some exemplary embodiments of the present disclosure.
Figure 10B:
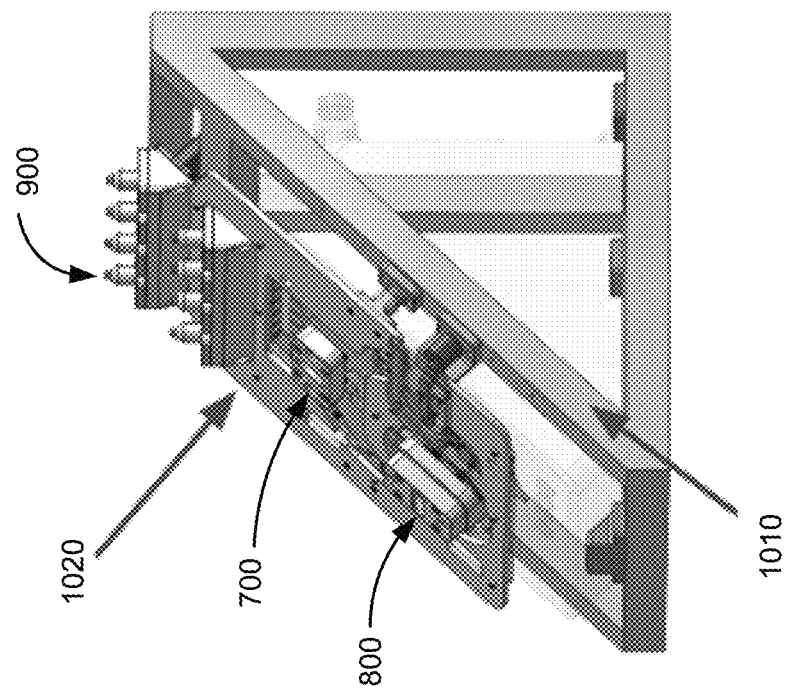
FIG. 10B is a perspective view illustrating the exemplary apparatus of FIG. 10A with the exemplary cartridge engaged with the exemplary dock in accordance with some exemplary embodiments of the present disclosure.
Figure 10A:
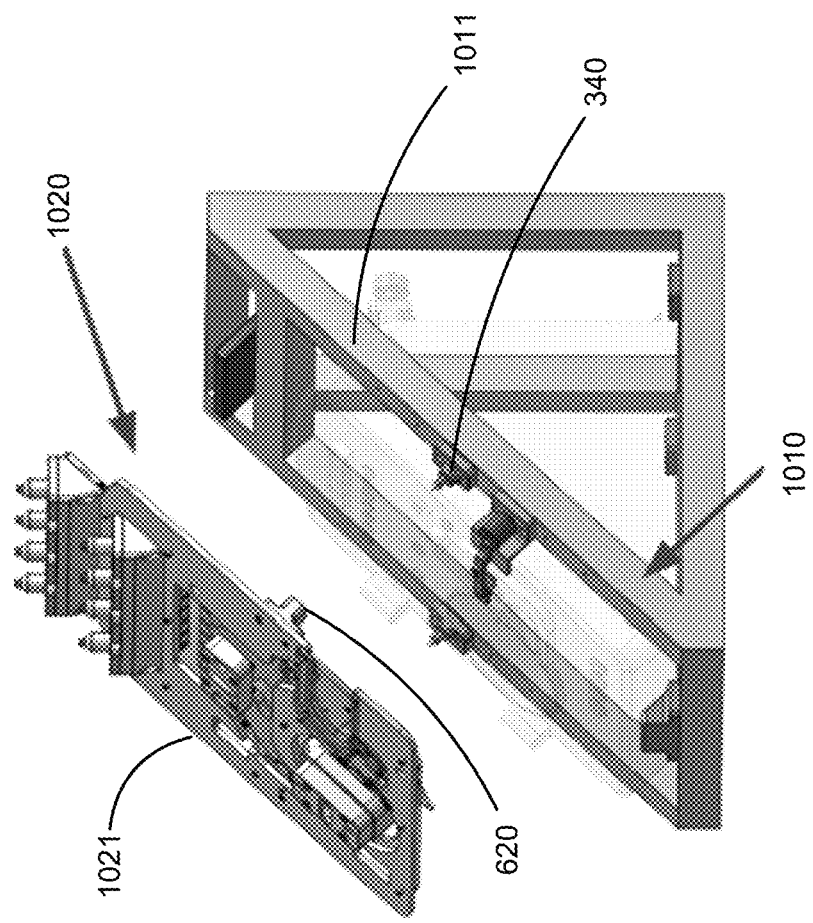
FIG. 10A is a perspective view illustrating an exemplary apparatus with an exemplary cartridge disengaged from an exemplary dock in accordance with some exemplary embodiments of the present disclosure.
Figure 10D:
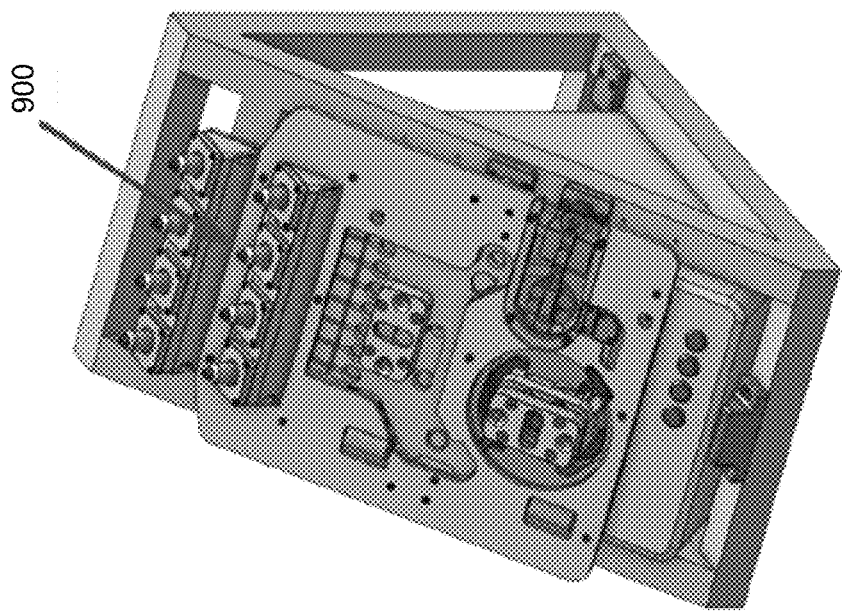
FIG. 10D is a perspective view illustrating installation of an consumable kit held by the exemplary cartridge on an instrument secured on the exemplary dock in accordance with some exemplary embodiments of the present disclosure.
Figure 10C:
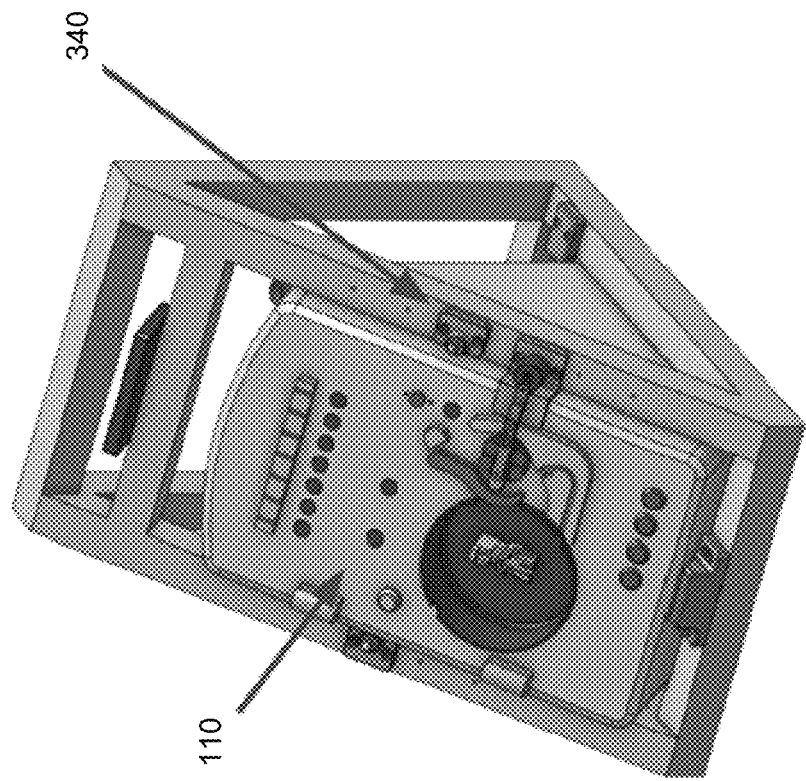
FIG. 10C is a perspective view illustrating an instrument secured on the exemplary dock in accordance with some exemplary embodiments of the present disclosure.
Figure 10F:
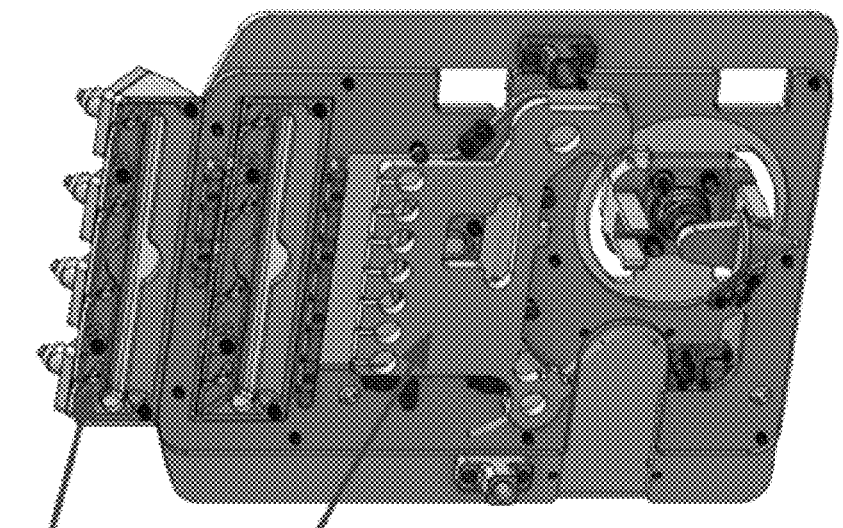
FIG. 10F is a rear perspective view illustrating the exemplary cartridge of FIG. 10E.
Figure 10E:
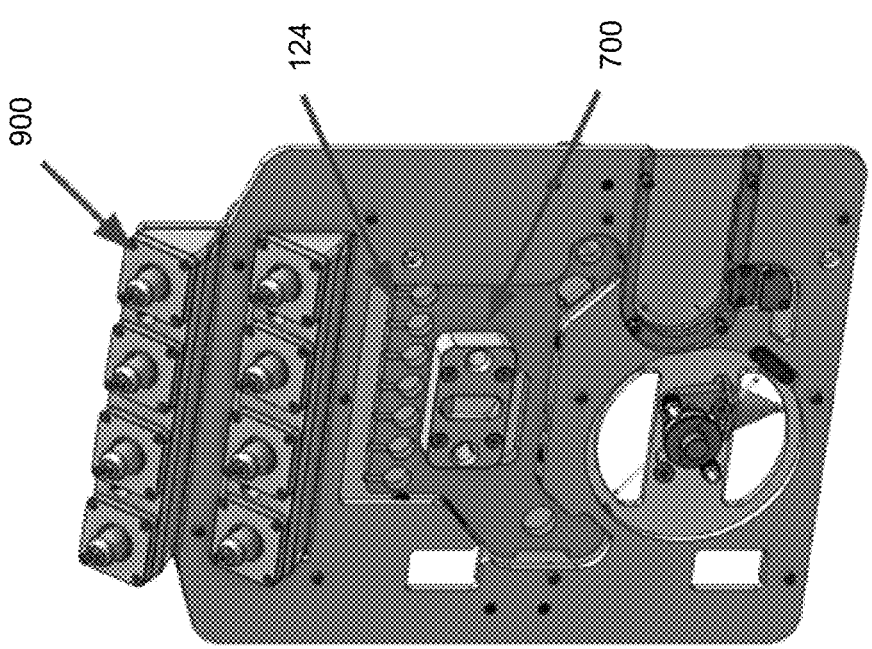
FIG. 10E is a front perspective view illustrating an exemplary cartridge in accordance with some exemplary embodiments of the present disclosure.
Figure 10H:
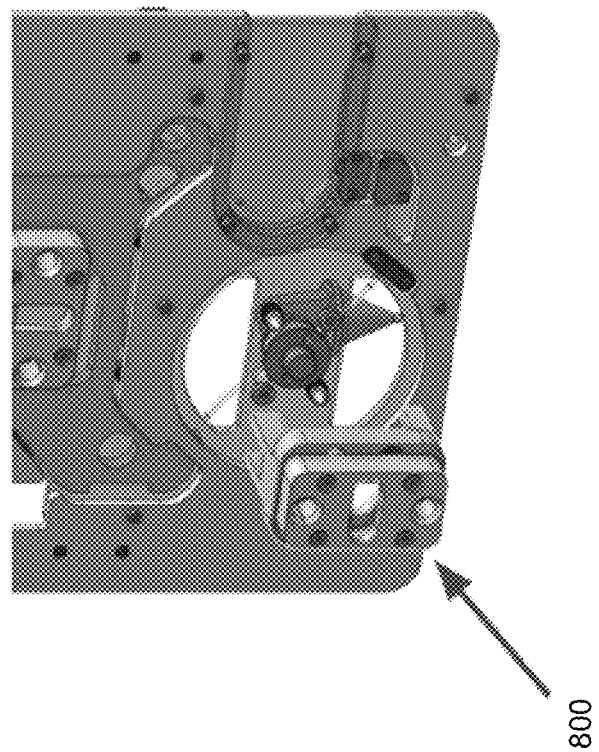
FIGS. 10G and 10H are perspective views illustrating an exemplary capsule removal assembly in accordance with some exemplary embodiments of the present disclosure.
Figure 10G:
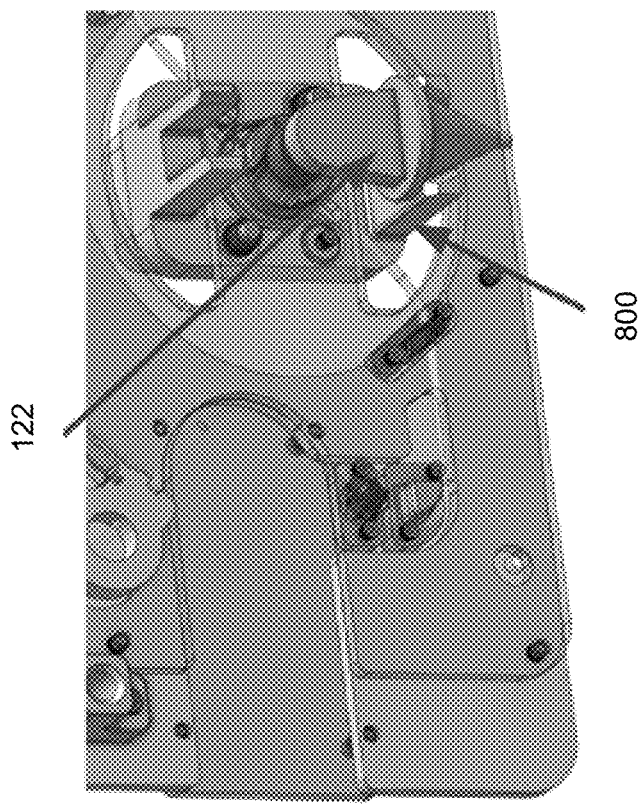

Referring in particular to FIGS. 9F and 9G, in some embodiments, the port body 901 includes a base, such as a base 910. While the base is illustrated to be of a circular shape, it should be noted that this is by way of example and the present disclosure is not limited thereto. For instance, the base can have a non-circular shape, such as oblong and oval. The base can also have other regular or irregular shapes. In some embodiments, the base is planar or substantially planar. The base is characterized by a first dimension (e.g., a width, a diameter) "D1" and a second dimension (e.g., a thickness) "D2."

In some embodiments, the port body 901 includes a stem, such as a stem 920, extended from the base. The stem is generally cylindrical or substantially cylindrical, with at least a portion of the stem having a circular or substantially circular cross section. The stem is characterized by a third dimension (e.g., an outer diameter) "D3" that is smaller than the first dimension "D1" of the base. In some embodiments, the stem includes two or more stem members that are removably coupled (e.g., snap-fitted, interference-fitted) with each other and configured to help secure the first device at the port body. For instance, in an exemplary embodiment, the stem includes a first stem member 921 and a second stem member 922 removably coupled with each other. In some embodiments, the first stem member is monolithically formed (e.g., molded) with the base as a single piece, and the second stem member is formed as a separate piece (e.g., an insert) to removably couple with the single piece.

In some embodiments, the port body 901 includes a bore, such as a bore 930, for housing at least a portion of the first device. The bore extends from an upper end portion of the stem to a lower end portion of the base. In other words, the bore passes completely through the port body. To help secure the first device with the port body, in some embodiments, a plurality of internal ribs are disposed on an inner surface of the stem or the port body (e.g., an interior surface that defines the bore). In some embodiments, the internal ribs are distributed circumferentially, with each internal rib having a surface configured for abutting an external wall of the first device and thus assists in securing the first device with the port body. In some embodiments, at least one internal rib in the plurality of internal ribs is formed on each of the first stem member and the second stem member.

In some embodiments, the port body 901 includes a tip, such as a tip 940, at a free end portion of the stem and configured for guiding a second device (not shown) when connecting the second device and the first device. As used herein, the free end portion of the stem refers to an end portion of the stem that is distal to the base and not disposed within the retainer. In some embodiments, the tip is a chamfered tip having a chamfer angle "a" and a chamfer length "L1." In some embodiments, the tip is a large chamfered tip with the chamfer angle of at least 45 degrees, at least 50 degrees, at least 55 degrees, or at least 60 degrees. In some embodiments, the stem has a length "L2," and the chamfer length "L1" of the tip is at least 10%, at least 15%, at least 20%, or at least 25% of the length "L2" of the stem. In an exemplary embodiment, the tip is a large chamfered tip with the chamfer angle within a range of from about 50 degrees to about 60 degrees and/or the chamfer length within a range of from about 15% to about 25% of the length of the stem. As such, the tip of the present disclosure makes it easy for robotic systems to interface with the port assembly when connecting the first device and a second device.

In some embodiments, the port body 901 includes one or more first anti-rotation members, such as one or more first anti-rotation members 950. The one or more first anti-rotation members are disposed at the base and configured to couple with one or more second anti-rotation members disposed at the retainer to restrict the port body from rotating relative to the retainer around an axis of the port body (e.g., the axis indicated by the dash line in FIG. 9C). The port body can include any suitable number (e.g., 1, 2, 3, or more than 3) of first anti-rotation members. For instance, in an exemplary embodiment, the port body includes two first anti-rotation members. Moreover, the one or more first anti-rotation members can be disposed at any suitable locations. For instance, in an exemplary embodiment, each of the one or more first anti-rotation members is formed at or adjacent to an outer edge of the base. Further, the one or more first anti-rotation members can be configured with any suitable shape that can be coupled with the second anti-rotation members disposed at the retainer. For instance, in a non-limiting embodiment, each of the one or more first anti-rotation members is a pin formed on the base. In addition, in embodiments with multiple first anti-rotation members, the first anti-rotation members can be but do not have to identical to each other, and can be but do not have to be disposed at locations symmetrical to each other.

Referring in particular to FIGS. 9D and 9E, in some embodiments, the retainer 902 includes a first retaining member, such as a first retaining member 960. The first retaining member has a first surface 961. A first through-hole, such as a first through-hole 962, is formed at the first retaining member. In some embodiments, the first through-hole is a circular or substantially circular through-hole. The first through-hole is characterized by a fourth dimension (e.g., a diameter) "D4." The fourth dimension "D4" of the first through-hole is larger or substantially larger than the third dimension "D3" of the stem, thereby allowing the stem of the port body to pass through and to move relative to the first retaining member. Moreover, the fourth dimension "D4" of the first through-hole is smaller than the first dimension "D1" of the base, thereby preventing the base of the port body from pulling out of the retainer via the first through-hole.

In some embodiments, the retainer 902 includes a second retaining member, such as a second retaining member 970, coupled or formed with the first retaining member. The second retaining member has a second surface 971 spaced apart from the first surface of the first retaining member in an axial direction of the port body, with the base of the port body disposed between the first surface of the first retaining member and the second surface of the second retaining member.

In some embodiments, the second dimension "D2" (e.g., the thickness) of the base equals or substantially equals a distance between the first surface of the first retaining member and the second surface of the second retaining member. For instance, in an exemplary embodiment, the thickness of the base equals or substantially equals a distance between the first surface of the first retaining member and the second surface of the second retaining member with a manufacturing clearance between the base and the first surface of the first retaining member and/or the second surface of the second retaining member. As such, the retainer restricts the base and thus the port body from moving in a direction parallel to the axis of the port body. Accordingly, the retainer restricts the first device from moving in a direction parallel to the axis of the port body.

In some embodiments, the retainer 902 includes one or more second anti-rotation members, such as second anti-rotation members 980, configured for coupling with the one or more first anti-rotation members of the port body, thereby restricting the port body from rotating relative to the retainer. The one or more second anti-rotation members can be disposed at the first retaining member or the second retaining member. As a non-limiting example, the one or more second anti-rotation members are illustrated at the second retaining member. Like the port body, the retainer can include any suitable number (e.g., 1, 2, 3, or more than 3) of second anti-rotation members. For instance, in an exemplary embodiment, the retainer includes two second anti-rotation members. The one or more second anti-rotation members can be configured with any suitable shape that can be coupled with the first anti-rotation members disposed at the retainer. For instance, in a non-limiting embodiment, each of the one or more second anti-rotation members is a hole formed at the second retaining member to receive a corresponding pin formed on the base. The hole can be a blind hole (e.g., a hole that does not pass completely through the second retaining member) or a through hole (e.g., a hole that passes completely through the second retaining member). As a non-limiting example, a blind hole is illustrated. The size of the hole is generally larger than the size of the corresponding pin.

However, the present disclosure is not limited thereto. For instance, in some alternative embodiments, each of the one or more second anti-rotation members is a pin disposed at the first retaining member or the second retaining member. Each of the one or more first anti-rotation members is a hole formed at the base to receive a corresponding pin disposed at the first retaining member or the second retaining member.

In some embodiments, one or more through-holes and/or one or more slots are formed at the second retaining member to facilitate connecting the first device with an input or output tube of the consumable kit. For instance, as a non-limiting example, it is illustrated that a second through-hole 972 and a slot 973 are formed on the second retaining member. The second through-hole is configured to allow an access to the first connector, and characterized by a fifth dimension (e.g., a diameter) "D5" of the second through-hole. The first dimension "D5" of the second through-hole is smaller than the first dimension "D1" of the base, thereby preventing the base of the port body from pulling out of the retainer via the second through-hole. In some embodiments, the second through-hole is a circular or substantially circular through-hole and concentric with the first through-hole formed on the first retaining member. The slot is configured to accommodate tubing or cable (e.g., an input or output tube of the consumable kit). In some embodiments, the slot extends from the second through-hole all the way to an outer edge of the second retaining member.

In some embodiments, the retainer 902 includes a rim, such as a rim 990, to help set a boundary for translational movement of the port body relative to the retainer. The rim can be disposed on the first surface of the first retaining member or the second surface of the second retaining member. In some embodiments, the rim is an integral part of the first or second retaining member. As a non-liming example, it is illustrated that the rim 990 is formed at the second surface of the second retaining member. The rim can be a single continuous rim or composed of multiple separate rim segments. It can be in a closed form shape or an open form shape. By way of example, the rim is shown to be continuous and in a closed form shape (except the portion cut off by the slot 973) that surrounds the base.

Referring in particular to FIG. 9C, in some embodiments, the port body 901 and the retainer 902 are configured such that one or more gaps are present between the port body and the retainer to allow for the translational movement of the port body relative to the retainer. The one or more gaps include but are not limited to: (i) a first gap "G1" between the stem of the port body and the first through-hole formed on the first retaining member (e.g., a gap between an outer surface of the stem 920 and a surface of the first retaining member that defines the first through-hole 962), (ii) a second gap "G2" between each respective first anti-rotation member in the one or more first anti-rotation members and a corresponding second anti-rotation member in the one or more second anti-rotation members (e.g., a gap between an outer surface of the pin 950 disposed at the base and a surface of the second retaining member that defines the hole 980), (iii) a third gap "G3" between the rim (e.g., an inner surface of the rim) formed on the first surface of the first retaining member or the second surface of the second retaining member and an outer edge of the base of the port body, or (iv) any combination thereof. In some such embodiments, the port body is movable translationally relative to the retainer in the plane substantially perpendicular to the axial direction of the port body within a range defined by the first gap, the second gap, the third gap, or any combination thereof. In some embodiments, the port body is movable translationally relative to the retainer in a radial direction of the port body. In some embodiments, the one or more gaps allow the port body to move translationally relative to the retainer in a radial direction of the port body for at least 1 mm, at least 1.5 mm, at least 2 mm, at least 2.5 mm, or at least 3 mm. in some embodiments, the one or more gaps allow the port body to move translationally relative to the retainer in a radial direction of the port body for at most 5 mm, at most 4.5 mm, at most 4 mm, at most 3.5 mm, or at most 3 mm. In some embodiments, the one or more gaps allow the port body to move translationally relative to the retainer in a radial direction of the port body from about 2 mm to about 3 mm. In an exemplary embodiment, the one or more gaps allow the port body to move translationally relative to the retainer in a radial direction of the port body for about 2.5 mm.

The cartridge can include additional, optional, or alternative components. For instance, referring to FIGS. 6C and 6D, in some embodiments, the cartridge includes a clip, such as a pump ball clip 660, configured to help retain the pump tube of the consumable kit. In some embodiments, the cartridge includes one or more windows, such as a window 670 and/or a window 680, to facilitate visualization. In some embodiments, the window 670 is positioned at a location corresponding to one or more pressure sensors of the instrument for visualizing and/or monitoring the pressure in the tube(s) of the consumable kit. The window 680 is positioned at a location corresponding to one or more bubble sensors of the instrument for visualizing and/or monitoring the bubbles in the tube(s) of the consumable kit. In some embodiments, the cartridge includes a bearing holder, such as a bearing holder 690. In some embodiments, the bearing holder is configured to assist in installing, holding, and/or removing the capsule and/or other functions.

Referring to FIGS. 10A-10H, there is depicted an exemplary apparatus, generally designated 1000, to facilitate automated loading and/or unloading a consumable kit (e.g., the consumable kit 220) to an instrument (e.g., the instrument 210) in accordance with some exemplary embodiments of the present disclosure. In some embodiments, the apparatus includes a dock, such as a dock 1010, for securing the instrument, and a cartridge, such as cartridge 1120, for holding the consumable kit. The cartridge 1020 is movable, for instance, by a robot (e.g., a robotic EOAT), and can be selectively coupled to the dock 1010.

Like the apparatus 200, in some embodiments, the dock 1110 includes a frame, such as a frame 1011, for surrounding (e.g., bordering) at least a portion of a perimeter of the instrument at or adjacent to the front surface 215 of the instrument. In some embodiments, the dock 1010 and the cartridge 1020 of the apparatus 1000 include a mechanism to establish a single degree of freedom motion for moving the cartridge relative to the dock. For instance, in some embodiments, the cartridge 1020 includes a mounting member, such as a mounting member 1021, and a plurality of first docking members, such as first docking members 620, coupled to or formed with the mounting member. The dock 1020 includes a plurality of second docking members, such as second docking members 340, coupled to or formed with the frame 1011. Each of the plurality of first docking members and a corresponding second docking member in the plurality of second docking members are configured to removably couple with each other, thereby establishing a single degree of freedom motion for moving the cartridge with respect to the dock. In some embodiments, the cartridge 1020 includes a mechanism to facilitate moving of the cartridge by a robot (e.g., a robotic end of arm tool). For instance, in some embodiments, the cartridge includes a first interface member, such as a first interface member 700, to facilitate moving of the mounting member to or from the dock by a robotic end of arm tool (EOAT). In some embodiments, the cartridge 1020 includes a mechanism to remove a centrifuge capsule (e.g., the centrifuge capsule 122) of a consumable kit (e.g., the consumable kit 120) from a centrifuge chamber carrier (e.g., the chamber carrier 112) of the instrument. For instance, in some embodiments, the cartridge includes a capsule removal assembly, such as a capsule removal unit 800, configured to removably couple to the mounting member.

The apparatuses (e.g., the apparatus 200, the apparatus 1000) of the present disclosure can be used alone or in combination with other devices to implement automated production of cellular engineering targets (e.g., cell therapies) at a biological foundry. Moreover, the components of the apparatuses (e.g., assemblies, units) disclosed herein are combinable in any useful number and combination. Further, at least some components of the apparatuses disclosed herein (e.g., the locking unit 400, the pump loading assembly 500, the first interface member 700, the port assembly 900) can be used alone or in combination with other devices different than the apparatus 200 and the apparatus 1000. For instance, the first interface member 700 and/or the port assembly 900 can be disposed at other cartridges to facilitate automated handling of such cartridges.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that includes a computer program mechanism embedded in a non-transitory computer-readable storage medium. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. An apparatus for facilitating automated loading of a consumable kit to an instrument, the apparatus comprising:
a cartridge comprising:
a mounting member for holding the consumable kit at a rear side of the mounting member;
a plurality of first docking members coupled to or formed with the mounting member; and
a plurality of first locking members coupled to or formed with the mounting member; and
a dock for securing the instrument, the dock comprising:
a frame for surrounding at least a portion of a perimeter of the instrument at or adjacent to a front surface of the instrument;
a plurality of second docking members coupled to or formed with the frame, wherein (i) each respective second docking member in the plurality of second docking members is configured to removably couple with a corresponding first docking member in the plurality of first docking members, and (ii) coupling of each respective second docking member in the plurality of second docking members with the corresponding first docking member in the plurality of first docking members (a) restricts the mounting member of the cartridge from moving relative to the frame in a plane parallel or substantially parallel to the front surface of the instrument, and (b) allows the mounting member of the cartridge to move relative to the frame in a first direction perpendicular or substantially perpendicular to the front surface of the instrument; and
a plurality of second locking members coupled to the frame, wherein (i) each respective second locking member in the plurality of second locking members is operably movable relative to the frame between a corresponding first position and a corresponding second position to selectively engage with or disengage from a corresponding first locking member in the plurality of first locking members, and (ii) engagement of each respective second locking member in the plurality of second locking members with the corresponding first locking member in the plurality of first locking members pushes the mounting member of the cartridge toward the front surface of the instrument and locks the mounting member of the cartridge with the frame of the dock.

2. The cartridge of claim 1, wherein the instrument is a counterflow centrifugation system or the consumable kit is a closed system kit.

3. The apparatus of claim 1, wherein the cartridge further comprises:
a plurality of tube retaining sets, wherein each respective tube retaining set in the plurality of tube retaining sets comprises one or more corresponding tube retaining members disposed at the rear side of the mounting member and configured to retain a corresponding tube in a plurality of input or output tubes of the consumable kit.

4. The apparatus of claim 3, wherein the one or more corresponding tube retaining members of each respective tube retaining set are disposed respectively at one or more corresponding locations on the rear side of the mounting member such that engagement of each respective second locking member in the plurality of second locking members with the corresponding first locking member in the plurality of first locking members pushes the corresponding tube in the plurality of input and output tubes of the consumable kit into a corresponding tubing track in a plurality of tubing tracks formed at the front surface of the instrument.

5. The apparatus of claim 3, wherein each of the one or more corresponding tube retaining members of a respective tube retaining set is a mechanical fastener.

6. The apparatus of claim 3, wherein the mounting member of the cartridge comprises a plurality of holes or windows for visualizing flow in the plurality of input or output tubes of the consumable kit.

7. The apparatus of claim 1, wherein the cartridge further comprises:
a first interface member connected to or formed with the mounting member, wherein the first interface member is configured for facilitating moving of the mounting member to or from the dock.

8. The cartridge of claim 7, wherein the first interface member comprises:
a first interface surface accessible from a front side of the mounting member, wherein the first interface surface is substantially planar;
a second interface surface opposite to the first interface surface;
an elongated slot formed through the first interface surface to allow an elongated cam bar of a robotic end of arm tool (EOAT) to insert into the first interface member; and
a recess recessed from the second interface surface toward the first interface surface, wherein the recess has a dimension larger than a width of the elongated slot and a length of the elongated cam bar, thereby allowing the elongated cam bar of the EOAT to rotate and engage with the first interface member.

9. The apparatus of claim 1, wherein the cartridge further comprises:
a plurality of port units connected to the mounting member, wherein each respective port unit in at least a subset of the plurality of port units is fluidly connected to a corresponding tube in a plurality of input and output tubes of the consumable kit.

10. The apparatus of claim 1, wherein:
each of the plurality of first docking members comprises a bushing; and
each of the plurality of second docking members comprises a post to removably couple with the bushing.

11. The apparatus of claim 1, wherein:
each of the plurality of first locking members comprises a ramp having a sloping surface with respect to the front surface of the instrument; and
each of the plurality of second locking members comprises a ramp follower operably movable on the sloping surface.

12. The apparatus of claim 1, wherein the dock further comprises:
a set of rails, each fixed on or formed with the frame; and
a set of slides, each respective slide in the set of slides coupled to a corresponding rail in the set of rails and operably movable along the corresponding rail,
wherein one or more second locking members in the plurality of second locking members are connected to or formed with each of the set of slides.

13. The apparatus of claim 12, wherein the dock further comprises:
a set of cam assemblies connected to the frame, wherein an end portion of each respective slide in the set of slides is coupled to a corresponding cam assembly in the set of cam assemblies and wherein the corresponding cam assembly converts a rotary motion to a linear motion of the respective slide.

14. The apparatus of claim 12, wherein:
the plurality of first locking members comprises four first locking members with two first locking members on each of a left side and a right side of the mounting member;
the set of rails comprises a left rail on a left side of the frame and a right rail on a right side of the frame;
the set of slides comprises a left slide coupled to the left rail and a right slide coupled to the right rail; and
the plurality of second locking members comprises four second locking members with two second locking members on each of the left rail and the right rail.

15. The apparatus of claim 1, wherein the dock further comprises:
a plurality of face reference members disposed at a front surface of the frame, wherein each of the plurality of face reference members comprises a suspension beyond an inner edge of the frame to abut the front surface of the instrument, thereby aligning the front surface of the frame with the front surface of the instrument.

16. The apparatus of claim 15, wherein each of the plurality of face reference members comprises a pin fastened to the frame, wherein the pin is elongated in a direction parallel or substantially parallel to the front surface of the frame.

17. The apparatus of claim 1, wherein the dock further comprises:
a base for holding the instrument; and
a plurality of upright members fixed on the base to support the frame such that the frame is disposed at a first angle with respect to the base.

18. The apparatus of claim 17, wherein the dock further comprises:
a plurality of stoppers fixed on the base, wherein each of the plurality of stoppers is adjustable and configured for abutting a wall of the instrument.

19. The apparatus of claim 1, wherein the dock further comprises:
a pump tube loading assembly connected to the frame and configured for placing at least a portion of a pump tube of the consumable kit into a peristaltic pump head of the instrument, wherein the pump tube loading assembly comprises:
a loading member comprising (i) a platform having a sector-shape or a substantial sector-shape and (ii) a finger disposed at or adjacent to a circumferential edge of the platform and extended toward the instrument beyond the platform; and
a driving unit configured to rotate the loading member, thereby causing the finger to press at least the portion of the pump tube of the consumable kit into a peristaltic pump head to get it seated on rollers of the peristaltic pump head of the instrument and using the platform to prevent at least the portion of the pump tube of the consumable kit from popping out of the peristaltic pump head.

20. The apparatus of claim 19, wherein the driving unit rotates the loading member around a rotational axis of the platform that is aligned with an axis of the peristaltic pump head of the instrument.

21. The apparatus of claim 19, wherein the driving unit comprises:
a plurality of shafts coupled to each other by a timing belt.

22. The apparatus of claim 1, further comprising:
a capsule releasing member configured for unlocking a centrifuge capsule of the consumable kit from a centrifuge chamber carrier of the instrument; and
a second interface member connected to or formed with the capsule releasing member, wherein the second interface member is robot-operable, thereby facilitating moving of the capsule releasing member relative to the instrument.

23. The apparatus of claim 22, wherein the capsule releasing member comprises:
a first jaw insertable through a first hole formed on the mounting member and configured to grip the centrifuge capsule of the consumable kit; and
a second jaw insertable through a second hole formed on the mounting member and configured to lift a lever in the centrifuge chamber carrier of the instrument, thereby unlocking the centrifuge capsule of the consumable kit from a centrifuge chamber carrier of the instrument.

24. An apparatus for facilitating automated loading of a consumable kit to an instrument, the apparatus comprising:
a cartridge for holding the consumable kit, wherein the cartridge is movable by a robot; and
a dock for securing the instrument, the dock comprising:
a base for holding the instrument;
a frame for surrounding at least a portion of a perimeter of the instrument at or adjacent to a front surface of the instrument;
a plurality of upright members fixed on the base to support the frame such that the frame is disposed at a first angle with respect to the base; and
a plurality of face reference members disposed at a front surface of the frame, wherein each of the plurality of face reference members comprises a suspension beyond an inner edge of the frame to abut the front surface of the instrument, thereby aligning the front surface of the frame with the front surface of the instrument.

25. The apparatus of claim 24, wherein each of the plurality of face reference members comprises a pin that is parallel or substantially parallel to the front surface of the frame and fastened to the frame.

26. The apparatus of claim 24, wherein the dock further comprises:
a plurality of stoppers fixed on the base, each adjustable and configured for abutting a wall of the instrument.

27. An apparatus for facilitating automated loading of a consumable kit to an instrument, the apparatus comprising:
a cartridge for holding the consumable kit, wherein the cartridge is movable by a robot; and
a dock for securing the instrument, the dock comprising:
a frame for surrounding at least a portion of a perimeter of the instrument at or adjacent to a front surface of the instrument; and
a pump tube loading assembly connected to the frame and configured for placing at least a portion of a pump tube of the consumable kit into a peristaltic pump head of the instrument, wherein the pump tube loading assembly comprises:
a loading member comprising (i) a platform having a sector-shape or a substantial sector-shape and comprising a retaining surface that faces the instrument, wherein the retaining surface is parallel or substantially parallel to the front surface of the instrument, and (ii) a finger disposed at or adjacent to a circumferential edge of the platform and extended toward the instrument beyond the retaining surface of the platform; and a driving unit configured to rotate the loading member, thereby causing the finger to press at least the portion of the pump tube of the consumable kit into a peristaltic pump head to seat on rollers of the peristaltic pump head of the instrument and causing the platform to confine at least the portion of the pump tube of the consumable kit to prevent the pump tube of the consumable kit from popping out of the peristaltic pump head.

28. The apparatus of claim 27, wherein the driving unit rotates the loading member around a rotational axis of the platform that is aligned with an axis of the peristaltic pump head of the instrument.

29. An apparatus for facilitating automated loading of a consumable kit to an instrument, the apparatus comprising:

a cartridge movable by a robot, the cartridge comprising:
a mounting member for holding the consumable kit at a back side of the mounting member;
a plurality of first locking members coupled to or formed with the mounting member; and
a plurality of tube retaining sets, wherein each respective tube retaining set in the plurality of tube retaining sets comprises one or more corresponding tube retaining members disposed at the back side of the mounting member and configured to retain a corresponding tube in a plurality of input and output tubes of the consumable kit; and a dock for securing the instrument, the dock comprising:
a frame for surrounding at least a portion of a perimeter of the instrument at or adjacent to a front surface of the instrument; and
a plurality of second locking members coupled to the frame, wherein each respective second locking member in the plurality of second locking members is configured to selectively engage with or disengage from a corresponding first locking member in the plurality of first locking members, and wherein the one or more corresponding tube retaining members of each respective tube retaining set are disposed respectively at one or more corresponding locations on the back side of the mounting member such that engagement of each respective second locking member in the plurality of second locking members with the corresponding first locking member in the plurality of first locking members pushes the corresponding tube in the plurality of input and output tubes of the consumable kit into a corresponding tubing track in a plurality of tubing tracks formed at the front surface of the instrument.

30. The apparatus of claim 29, wherein the dock further comprises:

a pump tube loading assembly connected to the frame and configured for placing at least a portion of a pump tube of the consumable kit around a peristaltic pump head of the instrument, wherein the pump tube loading assembly comprises:
a loading member comprising (i) a platform having a sector-shape or a substantial sector-shape and (ii) a finger disposed at or adjacent to a circumferential edge of the platform and extended toward the instrument beyond the platform; and
a driving unit configured to rotate the loading member, thereby causing the finger to press at least the portion of the pump tube of the consumable kit into a peristaltic pump head to get it seated on rollers of the peristaltic pump head of the instrument and using the platform to prevent at least the portion of the pump tube of the consumable kit from popping out of the peristaltic pump head.

\* \* \* \* \*